US008598342B2

(12) United States Patent
Kahne et al.

(10) Patent No.: US 8,598,342 B2
(45) Date of Patent: Dec. 3, 2013

(54) METHODS AND COMPOUNDS FOR ANTIMICROBIAL INTERVENTION

(75) Inventors: Suzanne Walker Kahne, Brookline, MA (US); Jonathan G. Swoboda, Oil City, PA (US); Timothy C. Meredith, Plymouth Meeting, PA (US); Kyungae Lee, Newton, MA (US); Jennifer Campbell, Brighton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 21 days.

(21) Appl. No.: 12/997,429

(22) PCT Filed: Jun. 5, 2009

(86) PCT No.: PCT/US2009/003424
§ 371 (c)(1),
(2), (4) Date: Mar. 11, 2011

(87) PCT Pub. No.: WO2009/151561
PCT Pub. Date: Dec. 17, 2009

(65) Prior Publication Data
US 2012/0046282 A1 Feb. 23, 2012

Related U.S. Application Data

(60) Provisional application No. 61/060,909, filed on Jun. 12, 2008.

(51) Int. Cl.
| C07D 491/00 | (2006.01) |
| C07D 471/00 | (2006.01) |
| C07D 413/00 | (2006.01) |
| A61K 31/519 | (2006.01) |

(52) U.S. Cl.
USPC ........ 544/251; 544/247; 544/115; 514/233.2; 514/257; 514/267

(58) Field of Classification Search
USPC ........ 544/251, 247, 115, 233.3; 514/257, 267
See application file for complete search history.

(56) References Cited

U.S. PATENT DOCUMENTS

| 3,854,480 A | 12/1974 | Zaffaroni |
| 4,452,775 A | 6/1984 | Kent |
| 4,675,189 A | 6/1987 | Kent et al. |
| 5,075,109 A | 12/1991 | Tice et al. |
| 5,133,974 A | 7/1992 | Paradissis et al. |
| 5,407,686 A | 4/1995 | Patel et al. |
| 5,736,152 A | 4/1998 | Dunn |

FOREIGN PATENT DOCUMENTS

| WO | WO 95/24929 | 9/1995 |
| WO | WO 2004/050846 A2 | 6/2004 |
| WO | WO 2007/081583 A2 | 7/2007 |
| WO | WO 2009/093934 A2 | 7/2009 |

OTHER PUBLICATIONS

International Search Report and Written Opinion for PCT/US2009/003424, mailed Mar. 2, 2010.
International Preliminary Report on Patentability for PCT/US2009/003424, mailed Dec. 23, 2010.
Alagarsamy et al., AntiHIV, antibacterial and antifungal activities of some novel 1, 4-disubstituted-1,2,4-triazolo[4,3-a] quinazolin-5(4h)-ones. Indian Journal of Pharmaceutical Sciences. 2006;68(4):532-5.
Andersson et al., The biological cost of antibiotic resistance. Curr Opin Microbiol. Oct. 1999;2(5):489-93.
Baba et al., Genome sequence of *Staphylococcus aureus* strain Newman and comparative analysis of staphylococcal genomes: polymorphism and evolution of two major pathogenicity islands. J Bacteriol. Jan. 2008;190(1):300-10. Epub Oct. 19, 2007.
Badurina et al., CTP:glycerol 3-phosphate cytidylyltransferase (TarD) from *Staphylococcus aureus* catalyzes the cytidylyl transfer via an ordered Bi-Bi reaction mechanism with micromolar K(m) values. Biochim Biophys Acta. Mar. 21, 2003;1646(1-2):196-206.
Bae et al., Allelic replacement in *Staphylococcus aureus* with inducible counter-selection. Plasmid. Jan. 2006;55(1):58-63. Epub Jul. 26, 2005.
Berge et al., Pharmaceutical salts. J Pharm Sci. Jan. 1977;66(1):1-19.
Berka et al., Microarray analysis of the *Bacillus subtilis* K-state: genome-wide expression changes dependent on ComK. Mol Microbiol. Mar. 2002;43(5):1331-45.
Bou, Minimum inhibitory concentration (MIC) analysis and susceptibility testing of MRSA. Methods Mol Biol. 2007;391:29-49.
Brown et al., A revised pathway proposed for *Staphylococcus aureus* wall teichoic acid biosynthesis based on in vitro reconstitution of the intracellular steps. Chem Biol. Jan. 2008;15(1):12-21.
Brown et al., *Staphylococcus aureus* and *Bacillus subtilis* W23 make polyribitol wall teichoic acids using different enzymatic pathways. Chem Biol. Oct. 29, 2010;17(10):1101-10.
Campbell et al., Synthetic lethal compound combinations reveal a fundamental connection between wall teichoic acid and peptidoglycan biosyntheses in *Staphylococcus aureus*. ACS Chem Biol. Jan. 21, 2011;6(1):106-16. Epub Nov. 4, 2010.
Clement et al., Evidence of an intracellular reservoir in the nasal mucosa of patients with recurrent *Staphylococcus aureus* rhinosinusitis. J Infect Dis. Sep. 15, 2005;192(6):1023-8. Epub Aug. 9, 2005.

(Continued)

*Primary Examiner* — Shirley V Gembeh
(74) *Attorney, Agent, or Firm* — Wolf, Greenfield & Sacks, P.C.; C. Hunter Baker

(57) ABSTRACT

The present invention provides Wall Teichoic Acid biosynthesis inhibitors such as compound 1835F03 (targocil) and related synthetic analogs. The invention also provides pharmaceutical compositions thereof and methods for treating bacterial infection and the suppression of growth of bacterial cells by administering a Wall Teichoic Acid biosynthesis inhibitor. The invention is particularly useful for the treatment of Methicillin-resistant *Staphylococcus aureus* (MRSA). The invention further provides procedures for the syntheses of Wall Teichoic Acid biosynthesis inhibitors. The invention also provides methods for the identification of antibacterial therapeutic agents.

20 Claims, 34 Drawing Sheets

(56) References Cited

OTHER PUBLICATIONS

D'Elia et al., Lesions in teichoic acid biosynthesis in *Staphylococcus aureus* lead to a lethal gain of function in the otherwise dispensable pathway. J Bacteriol. Jun. 2006;188(12):4183-9.

Davidson et al., Structure, function, and evolution of bacterial ATP-binding cassette systems. Microbiol Mol Biol Rev. Jun. 2008;72(2):317-64, table of contents.

Endl et al., Chemical composition and structure of cell wall teichoic acids of staphylococci. Arch Microbiol. Sep. 1983;135(3):215-23.

Gründling et al., Cross-linked peptidoglycan mediates lysostaphin binding to the cell wall envelope of *Staphylococcus aureus*. J Bacteriol. Apr. 2006;188(7):2463-72.

Hancock et al., Biosynthesis of the unit that links teichoic acid to the bacterial wall: inhibition by tunicamycin. FEBS Lett. Oct. 15, 1976;69(1):75-80.

Jantová et al., Antibacterial effect of some substituted tricyclic quinazolines and their synthetic precursors. Folia Microbiol (Praha). 1999;44(2):187-90.

Jantová et al., Antibacterial effects of trisubstituted quinazoline derivatives. Folia Microbiol (Praha). 2000;45(2):133-7.

Jantová et al., In vitro antibacterial activity of ten series of substituted quinazolines. Biologia, Bratislava. 2004. 59/6. 741-52.

Karamata et al., Expression of heterologous genes for wall teichoic acid in *Bacillus subtilis* 168. Mol Gen Genet. Apr. 1987;207(1):73-81.

Kreiswirth et al., The toxic shock syndrome exotoxin structural gene is not detectably transmitted by a prophage. Nature. Oct. 20-26, 1983;305(5936):709-12.

Lazarevic et al., Comparison of ribitol and glycerol teichoic acid genes in *Bacillus subtilis* W23 and 168: identical function, similar divergent organization, but different regulation. Microbiology. Mar. 2002;148(Pt 3):815-24.

Lazarevic et al., The tagGH operon of *Bacillus subtilis* 168 encodes a two-component ABC transporter involved in the metabolism of two wall teichoic acids. Mol Microbiol. Apr. 1995;16(2):345-55.

Lee et al., Construction of single-copy integration vectors for *Staphylococcus aureus*. Gene. Jul. 15, 1991;103(1):101-5.

Lee et al., Development of improved inhibitors of wall teichoic acid biosynthesis with potent activity against *Staphylococcus aureus*. Bioorg Med Chem Lett. Mar. 1, 2010;20(5):1767-70. Epub Jan. 20, 2010.

Mauel et al., The essential nature of teichoic acids in *Bacillus subtilis* as revealed by insertional mutagenesis. Mol Gen Genet. 1991;215:388-94.

Meredith et al., Late-stage polyribitol phosphate wall teichoic acid biosynthesis in *Staphylococcus aureus*. J Bacteriol. Apr. 2008;190(8):3046-56. Epub Feb. 15, 2008.

Neuhaus et al., A continuum of anionic charge: structures and functions of D-alanyl-teichoic acids in gram-positive bacteria. Microbiol Mol Biol Rev. Dec. 2003;67(4):686-723.

Newmark et al., Preparation and Properties of Adducts of Streptokinase and Streptokinase-Plasmin Complex with Polyethylene Glycol and Pluronic Polyol F38. J Appl Biochem. 1982;4:185-9.

Novick, Properties of a cryptic high-frequency transducing phage in *Staphylococcus aureus*. Virology. Sep. 1967;33(1):155-66.

Ohlsen et al., Novel targets for antibiotics in *Staphylococcus aureus*. Future Microbiol. Dec. 2007;2(6):655-66.

Pereira et al., Bifunctional catalysis by CDP-ribitol synthase: convergent recruitment of reductase and cytidylyltransferase activities in *Haemophilus influenzae* and *Staphylococcus aureus*. Biochemistry. Sep. 21, 2004;43(37):11802-12.

Pereira et al., Duplication of teichoic acid biosynthetic genes in *Staphylococcus aureus* leads to functionally redundant poly(ribitol phosphate) polymerases. J Bacteriol. Aug. 2008;190(16):5642-9. Epub Jun. 13, 2008.

Peters et al., The research agenda of the National Institute of Allergy and Infectious Diseases for antimicrobial resistance. J Infect Dis. Apr. 15, 2008;197(8):1087-93.

Sawhney et al., Bioerodible Hydrogels Based on Photopolymerized Poly(ethylene glycol-co-poly($\alpha$-hydroxyl acid) Diacrylate Macromers. Macromolecules. 1993;26:581-7.

Schenk et al., Improved method for electroporation of *Staphylococcus aureus*. FEMS Microbiol Lett. Jul. 1, 1992;73(1-2):133-8.

Sievert et al., Vancomycin-resistant *Staphylococcus aureus* in the United States, 2002-2006. Clin Infect Dis. Mar. 1, 2008;46(5):668-74.

Suzuki et al., In vitro antimicrobial activity of wall teichoic acid biosynthesis inhibitors against *Staphylococcus aureus* isolates. Antimicrob Agents Chemother. Feb. 2011;55(2):767-74. Epub Nov. 22, 2010.

Suzuki et al., Role of Wall Teichoic Acids in *Staphylococcus aureus* Endophthalmitis. Invest Ophthalmol Vis Sci. May 16, 2011;52(6):3187-92. Print 2011.

Swoboda et al., Discovery of a small molecule that blocks wall teichoic acid biosynthesis in *Staphylococcus aureus*. ACS Chem Biol. Oct. 16, 2009;4(10):875-83.

Swoboda et al., Wall teichoic acid function, biosynthesis, and inhibition. Chembiochem. Jan. 4, 2010;11(1):35-45.

Vinogradov et al., Structural elucidation of the extracellular and cell-wall teichoic acids of *Staphylococcus aureus* MN8m, a biotihn forming strain. Carbohydr Res. May 1, 2006;341(6):73843. Epub Feb. 3, 2006.

Ward, Teichoic and teichuronic acids: biosynthesis, assembly, and location. Microbiol Rev. Jun. 1981;45(2):211-43.

Weidenmaier et al., Differential roles of sortase-anchored surface proteins and wall teichoic acid in *Staphylococcus aureus* nasal colonization. Int J Med Microbiol. Jul. 2008;298(5-6):505-13 Epub Jan. 24, 2008.

Weidenmaier et al., Lack of wall teichoic acids in *Staphylococcus aureus* leads to reduced interactions with endothelial cells and to attenuated virulence in a rabbit model of endocarditis. J Infect Dis. May 15, 2005;191(10):1771-7. Epub Apr. 11, 2005. J Infect Dis. Jul. 15, 2005;192(2):355.

Weidenmaier et al., Role of teichoic acids in *Staphylococcus aureus* nasal colonization, a major risk factor in nosocomial infections. Nat Med. Mar. 2004;10(3):243-5. Epub Feb. 1, 2004.

Wilen et al., Tetrahedron Report No. 38. Strategies in Optical Resolutions. Tetrahedron. 1977;33:2725-36.

Witte et al., Emergence and spread of antibiotic-resistant Gram-positive bacterial pathogens. Int J Med Microbiol. Jul. 2008;298(5-6):365-77. Epub Mar. 5, 2008.

Yeh et al., Functional classification of drugs by properties of their pairwise interactions. Nat Genet. Apr. 2006;38(4):489-94. Epub Mar. 19, 2006.

Young et al., Pseudo-allelic relationship between non-homologous genes concerned with biosynthesis of polyglycerol phosphate and polyribitol phosphate teichoic acids in *Bacillus subtilis* strains 168 and W23. Mol Microbiol. Dec. 1989;3(12):1805-12.

Extended European Search Report for EP 09762857.2, mailed Feb. 1, 2012.

Regulated, ectopic TarL expression coupled with gene deletion of the wildtype allele —O— RN4220 [geh::(pCL25int-P$_{spac}$ tarL)Em$^T$ ]tarL::tetL Tc$^T$ —●— RN4220 ΔtarO[geh::(pCL25int-P$_{spac}$ tarL) Em$^T$]tarL::tetL Tc$^T$ 1835, F03
1835F03 (Targocil)

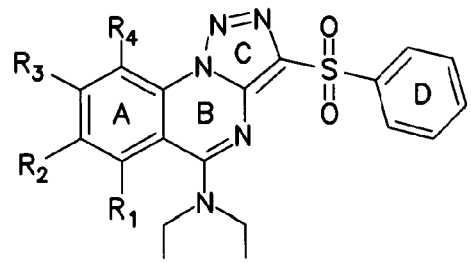

| Sample | R₁ | R₂ | R₃ | R₄ | WT MIC (μM) | ΔTarO MIC (μM) |
|---|---|---|---|---|---|---|
| Targocil | -H | -Cl | -H | -H | 3.13 | NA(78%) |
| 4-22-2 | -Cl | -H | -H | -H | NA(87%)ᵃ | NA(71%) |
| 4-22-3 | -H | -CH₃ | -H | -H | 25 | >100(78%)ᵇ |
| 4-22-5 | -H | -NO₂ | -H | -H | >100(31%) | >100(86%) |
| 4-22-1 | -H | -Cl | -H | -H | 3.25 | NA (98%) |
| 4-22-4 | -H | -H | -CH₃ | -H | NA (100%) | NA (106%) |
| 4-22-6 | -H | -H | -NO₂ | -H | 100 | 50 |
| 4-24 | -H | -H | -Cl | -H | NA (90%) | NA (102%) |
| 4-22-8 | -H | -H | -Br | -H | >100(35%) | 100 |
| 4-20 | -H | -H | -H | -Cl | NA (94%) | NA (109%) |
| 4-22-7 | -H | -OCH₃ | -OCH₃ | -H | 3.25 | NA (99%) |
| 4-21-1 | (structure) | | | | NA (67%) | NA (72%) |
| 4-18-2 | (structure) | | | | NA (61%) | >100(38%) |
| 4-12-3 | (structure) | | | | >100(13%) | 50 |

ᵃ Number in parentheses represents the percent survival at the highest concentration tested (100 μM).
ᵇ MIC reported as >100 μM if percent survival was <50% at 100 μM.

FIG. 15A

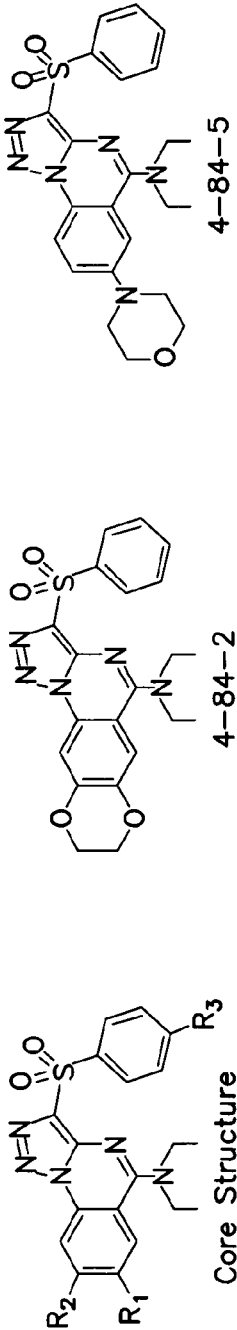

FIG. 15B

| Compound ID | R₁ | R₂ | R₃ | WT MIC (µM) | ΔTarO MIC (µM) |
|---|---|---|---|---|---|
| 4-84-1 | -H | -OCH₃ | -H | 100 [46%]* | 100[69.6%] |
| 4-84-2 | See above | | | >100[102.5%] | >100[100.5%] |
| 4-84-3 | -C≡N | -H | -H | >100[93.7%] | >100[94.8%] |
| 4-84-4 | -Br | -H | -H | 12.5[7.0%] | 100[13.5%] |
| 4-84-5 | See above | | | >100[90.0%] | >100[93.4%] |
| 4-88-1 | -F | -H | -H | 100[66.0%] | >100[95.0%] |
| 4-88-4 | -OCH₃ | -H | -CH₃ | >100[31.4%] | >100[90.1%] |
| 4-82 | -OCH₃ | -OCH₃ | -H | 3.125[13.2%] | >100[89.9%] |
| 4-89 | -OCH₃ | -OCH₃ | -Cl | ≤0.78[-0.5%] | 100[61.3%] |
| targocil | -Cl | -H | -H | 6.25[5.7%] | >100[97.0%] |
| 4-22-7 | -OCH₃ | -OCH₃ | -H | 1.56[17.7%] | >100[94.4%] |

*The value in brackets indicates percent survival at the given concentration based on positive and negative controls for each strain. This data was collected 3-29-09 in a 96-well format with RN4220 wt and ΔtarO. Plates were incubated at 30°C overnight for 18h with shaking.

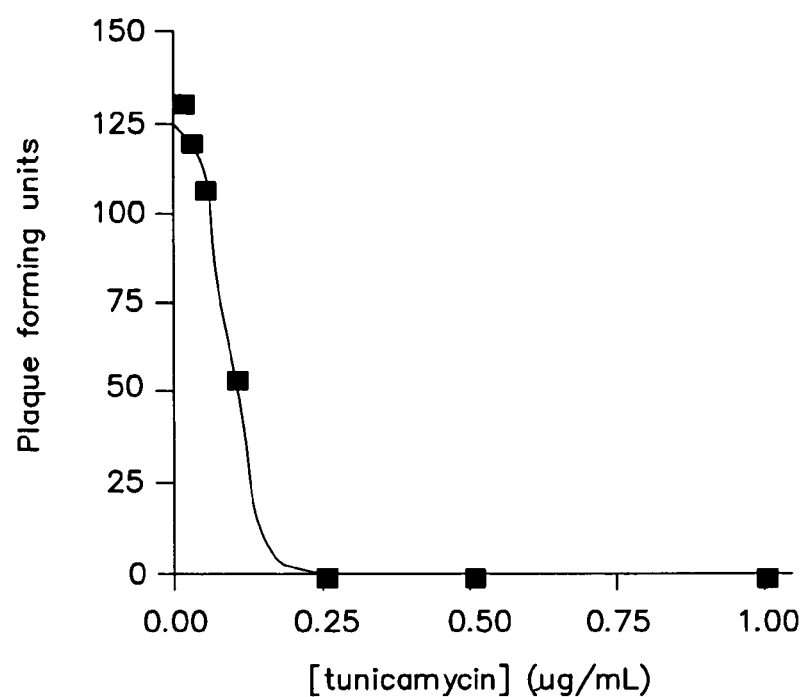
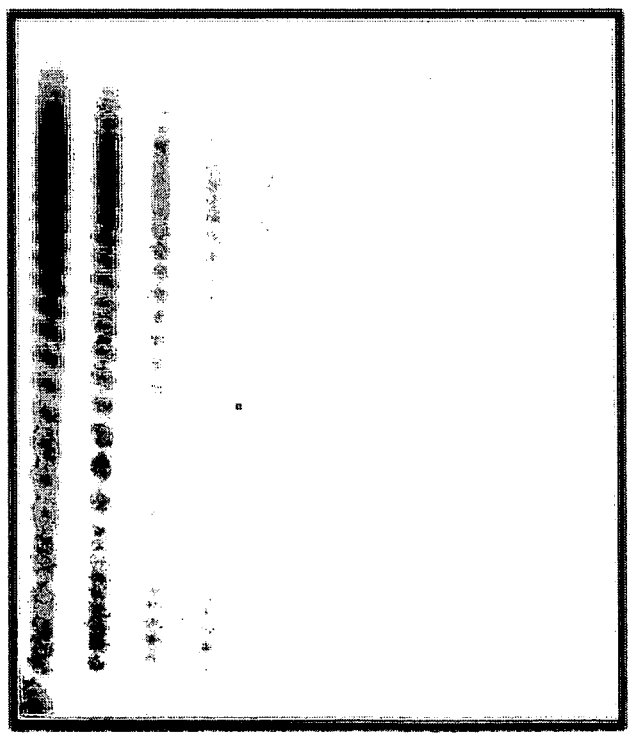
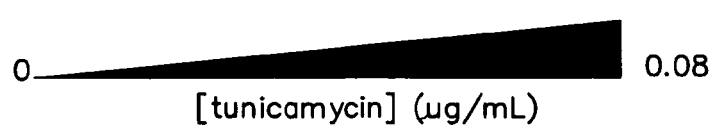
FIG. 19

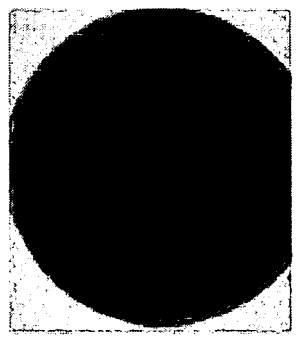
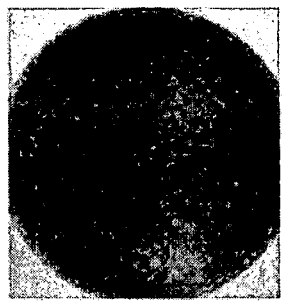
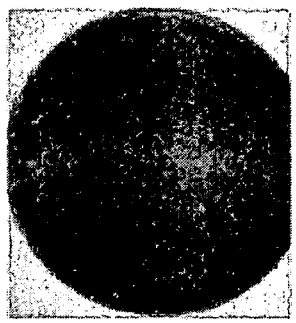
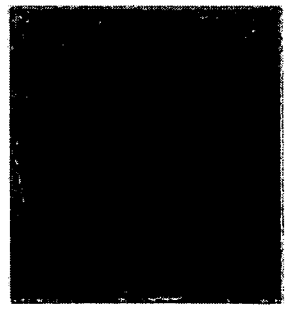
FIG. 22

| Strain | Genotype or Description | Source of Reference |
|---|---|---|
| S. aureus | | |
| RN450 | NCTC 8325-4, prophage cured, rsbU agr+ | (6) |
| RN4220 | RN450 r⁻m+, partial agr defect | (7) |
| ΔtarO | RN4220 ΔtarO | (8) |
| ΔtarA | RN4220 ΔtarA | This study |
| Newmann | Clinical isolate of S. aureus | (9) |
| MN8 | Clinical isolate of S. aureus | (10) |
| Wood 46 | strain of S. aureus used for MICs | ATCC 10832 |
| MRSA+ | clinical isolate of MRSA | This study |
| MRSA+B5271 | clinical isolate of MRSA | This study |
| MRSA+B5340 | clinical isolate of MRSA | This study |
| MRSA+1784A | clinical isolate of MRSA | This study |
| JT0025 | RN4220 ΔtarO [geh::(pCL25int-P$_{spac}$tarO)Kan$^r$] | This study |
| JT0409 | RN4220 targocil mutant 1 (phage resistant) | This study |
| JT0410 | RN4220 targocil mutant 2 (phage resistant) | This study |
| JT0411 | RN4220 targocil mutant 3 (phage resistant) | This study |
| JT0412 | RN4220 targocil mutant 4 (phage sensitive) | This study |
| JT0413 | RN4220 targocil mutant 5 (phage sensitive) | This study |
| JT399 | RN4220 [geh::(pCL25int-P$_{pen}$tarGH $^{SA}$)EM$^r$] | This study |
| JT400 | RN4220 [geh::(pCL25int-P$_{pen}$tarGH $^{BS}$)EM$^r$] | This study |
| JT0414 | RN4220 [tarG::tarG (mutant 4-F82L)] | This study |
| JT0415 | RN4220 [tarG::tarG (mutant 5-W73C)] | This study |
| S. pneumoniae | Gram-positive bacteria used as an MIC control | ATCC 43619 |
| B. subtilis | Strain 168, produces glycerol phosphate WTA | (11) |

(6) Novick R. (1967) Virology 33:155.
(7) Kreiswirth BN, Lofdahl S, Betley MJ, Oreilly M, Schlievert PM, Bergdoll MS, & Novick RP (1983) Nature 305:709-712
(8) Grundling A & Schneewind O (2006) Journal of Bacteriology 188:2463-2472
(9) Baba T, Bae T, Schneewind O, Takeuchi F, & Hiramatsu K (2008) Journal of Bacteriology 190:300-310
(10) Vinogradov E, Sadoyskaya I, Li JJ, & Jabbouri S (2006) Carbohydrate Research 341:738-743
(11) Berka RM, Hahn J, Albano M, Draskovic I, Persuh M, Sloma A, Widner W, & Dubnau D (2002) Molecular Microbiology 43:1331-1345

FIG. 25

| Plasmid/ Primer | Description[a] | Source or Reference |
|---|---|---|
| pL150 | E. coli/S. aureus shuttle vector Cm[r] | (12) |
| pMS182 | pL150 with P$_{pen}$Gfp – mut2 | This study |
| pMS183 | pL150 with P$_{pen}$Mcherry | This study |
| pDR201 | plasmid containing DNA encoding mCherry | D. Rudner |
| pKL147 | plasmid containing DNA encoding Gfp | D. Rudner |
| pL150P$_{pen}$ | E. coli/S. aureus shuttle vector containing the constitutive promoter P$_{pen}$ | This study |
| pCL25int | pCL25 with phage 54a integrase and ermC cassette replacing tetL Sec[r]Em[r] | (2) |
| pCL25intP$_{spac}$ | pCL25int with P$_{spac}$ IPTG inducible promoter P$_{pen}$ /lacI | (2) |
| pCL25intP$_{pen}$ | pCL25int with P$_{pen}$ constitutive promoter blaZ TT | (2) |
| pKOR1 | E. coli/S. aureus shuttle vector ori$^{Ts}$ inducible secY-antisense counterselection Ap[r] Cm[r] | (13) |
| Primers | | |
| P1tagGf | CCTATG*GTCGAC*G<u>AGGAGGAG</u>TAAAAGTATGAATGATTTGTTGCG _ | |
| P4tagGr | GACCGTC*GGCGCGCC*TTAAAGAAAGTCAACAAACTTG | |
| P1tagHf | CCTAT*GGCGCGCC*AG<u>AGGAGGAG</u>TAAAAGTATGAAACTAAAAGTT | |
| P4tagHr | GACCGTC*GGCGCGCC*TTATTTCAACATCAAAGTCAGTGTATG | |
| P1tarGf | CCTATG*GTCGAC*G<u>AGGAGGAG</u>TAAAAGTATGTCAGCAATAGG | |
| P4tarGr | GACCGTC*GGCGCGCC*TTACAAGAAGTCTGCAAATTG | |
| P1tarHf | CCTATG*GGCGCGCC*AG<u>AGGAGGAG</u>TAAAAGTATGAACGTTTCGG | |
| P4tarHr | GACCGTC*GGCGCGCC*TTATTTAATAACGAAGC | |
| Mcherrybluntf | AAGCTTACATA<u>AGGAGGAAC</u>TACT | |
| Mcherryr | GACCGTC*GGCGCGCC*TTATTTGTATAATTC | |
| Gfpbluntf | AAGCTTACATA<u>AGGAGGAAC</u>TACTATGAGTAAAGGAGAAG | |
| Gfpr | GACCGTC*GGCGCGCC*TTATTTGTATAGTTCATCCATGCC | |

[a]Restriction sites are italicized, synthetic ribosome binding sites are underlined, and gene coding sequences are indicated in bold type.

(2) Meredith TC, Swoboda JG, & Walker S (2008) Journal of Bacteriology 190: 3046–3056
(12) Bae T, & Schneewind O (2006) Plasmid 55: 58–63
(13) Lee CY, Buranen SL, & Ye ZH (1991) Gene 103: 101–105

FIG. 26

| | ERG | | | | | |
|---|---|---|---|---|---|---|
| | | 24h Bwave ratio | 48h Bwave ratio | average(24h) | SD(24h) | average(48h) | SD(48h) |
| 1 | Targocil mutant | 55.42530809 | 66.24614522 | 41.7502091 | 39.9159 | 50.77827324 | 48.8038 |
| 2 | Targocil mutant | 88.11188811 | 108.4084084 | | | | |
| 3 | Targocil mutant | 65.21384929 | 79.23681257 | | | | |
| 4 | Targocil mutant | 0 | 0 | | | | |
| 5 | Targocil mutant | 0 | 0 | | | | |
| 11 | RN6390 | 0 | 0 | 0 | 0 | 0 | 0 |
| 12 | RN6390 | 0 | 0 | | | | |
| 13 | RN6390 | 0 | 0 | | | | |
| 14 | RN6390 | 0 | 0 | | | | |
| 15 | RN6390 | 0 | 0 | | | | |

FIG. 27A

METHODS AND COMPOUNDS FOR ANTIMICROBIAL INTERVENTION

RELATED APPLICATIONS

The present application is a national stage filing under 35 U.S.C. §371 of international PCT application, PCT/US2009/003424, filed Jun. 5, 2009, which claims priority under 35 U.S.C. §119(e) to U.S. provisional patent application, U.S. Ser. No. 61/060,909, filed Jun. 12, 2008, each of which is incorporated herein by reference.

GOVERNMENT FUNDING

This invention was made with U.S. government support under grant numbers 5 RO1 GM078477-0 and 5 U54 AI057159-05 awarded by the National Institutes of Health. The U.S. Government has certain rights in the invention.

FIELD OF THE INVENTION

The invention provides methods for treating bacterial infection and the suppression of growth of bacterial cells by administering a Wall Teichoic Acid biosynthesis inhibitor. The invention also provides methods for the identification of antibacterial therapeutic agents.

BACKGROUND OF THE INVENTION

Wall Teichoic Acids (WTA) are found in many Gram-positive bacteria and consist of an anionic, phosphate rich polymer that is cross-linked to cell surface peptidoglycan. WTAs have many functions including maintaining the integrity of the cellular envelope. In *Bacillus subtilis* strain 168, the polymer portion of Wall Teichoic Acids contains glycerol phosphate, while in *B. subtilis* strain W23 and *Staphylococcus aureus* strains, the WTA polymer contains ribitol phosphate. Much of what is known about the *S. aureus* pathway is based on the *B. subtilis* strain W23 model. In *S. aureus*, WTAs play an essential role in adhesion to endothelial and epithelial tissues. WTAs have also been found to be critical for colonization in numerous infection models. A better understanding of the biosynthesis of WTAs will provide tools for making antimicrobials that target this pathway.

The development of antimicrobials effective against *S. aureus* is of particular importance. Invasive Methicillin-resistant *Staphylococcus aureus* (MRSA) infections have become a major public health problem, causing 94,000 life-threatening infections in 2005, of which almost 19,000 resulted in death. (N. K. Peters, D. M. Dixon, S. M. Holland, A. S. Fauci, (2008) *Journal of Infectious Diseases* 197, 1087) Recently, strains carrying genes encoding resistance to vancomycin, the "last resort" antibiotic for these infections, have begun to appear. (D. M. Sievert et al., (2008) *Clinical Infectious Diseases* 46, 668) New antibiotics to treat MRSA infections have been introduced recently, but as expected, clinical resistance has already been observed. (W. Witte et al., (2008) *International Journal of Medical Microbiology* 298, 365) It is imperative to continue discovering new targets and strategies to combat multi-drug resistant pathogens.

SUMMARY OF THE INVENTION

The invention provides methods for treating bacterial infection and the suppression of the growth of bacterial cells by administering a Wall Teichoic Acid biosynthesis inhibitor. The invention also provides antibacterial therapeutic agents as well as methods for the identification of antibacterial therapeutic agents.

Compounds of the present invention include Wall Teichoic Acid (WTA) biosynthesis inhibitors. According to one aspect of the invention, a compound is provided of the formula:

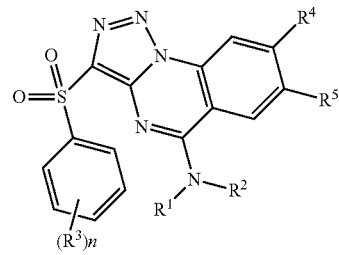

wherein:

$R^1$ and $R^2$ are independently selected from the group consisting of hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R^A$; $-CO_2R^A$; $-C(=O)N(R^A)_2$; or $-C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

wherein $R^1$ and $R^2$ may be taken together with the intervening N atom to form a heterocyclic moiety;

each occurrence of $R^3$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR^C$; $-C(=O)R^C$; $-CO_2R^C$; $-C(=O)N(R^C)_2$; $-CN$; $-SCN$; $-SR^C$; $-SOR^C$; $-SO_2R^C$; $-NO_2$; $-N(R^C)_2$; $-NHC(O)R^C$; or $-C(R^C)_3$; wherein each occurrence of $R^C$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

n is an integer between 0 and 5, inclusive;

$R^4$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR^D$; $-C(=O)R^D$; $-CO_2R^D$; $-C(=O)N(R^D)_2$; $-CN$; $-SCN$; $-SR^D$; $-SOR^D$; $-SO_2R^D$; $-NO_2$; $-N(R^D)_2$; $-NHC(O)R^D$; or $-C(R^D)_3$; wherein each occurrence of $R^D$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^5$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR^E$; —$C(=O)R^E$; —$CO_2R^E$; —$C(=O)N(R^E)_2$; —$CN$; —$SCN$; —$SR^E$; —$SOR^E$; —$SO_2R^E$; —$NO_2$; —$N(R^E)_2$; —$NHC(O)R^E$; or —$C(R^E)_3$; wherein each occurrence of $R^E$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; wherein $R^4$ and $R^5$ may be taken together with the intervening atoms to form a cyclic moiety; and pharmaceutically acceptable salts thereof;

with the provisos that $R^4$ and $R^5$ can not both be hydrogen; $R^4$ can not be hydrogen if $R^5$ is chloro; and the compound is not of the formula:

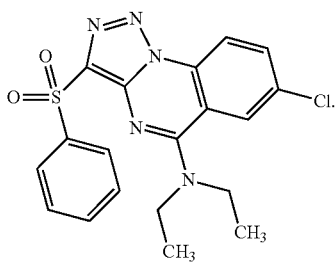

In further embodiments, the compound is selected from the group consisting of:

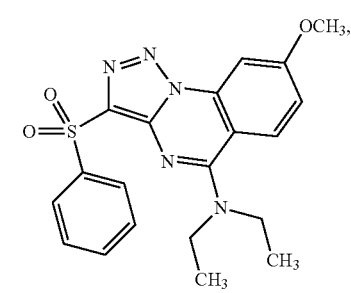

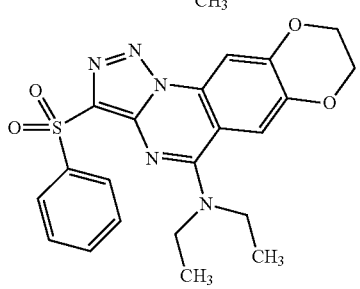

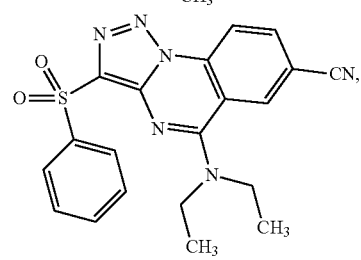

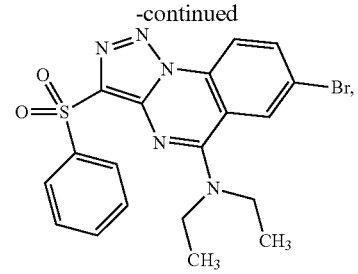

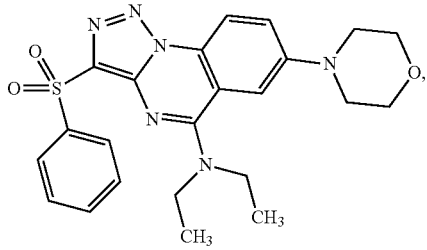

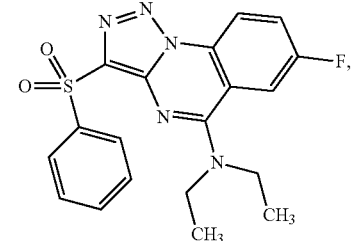

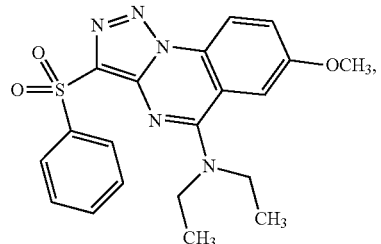

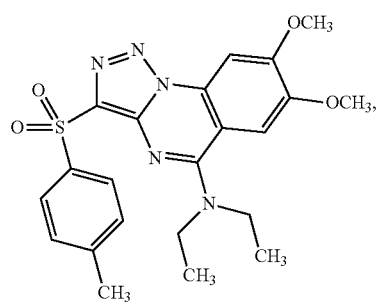

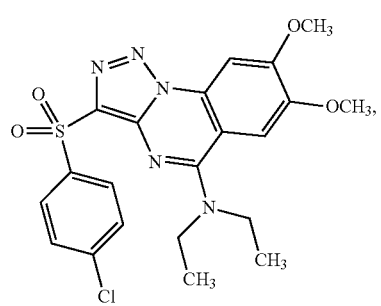

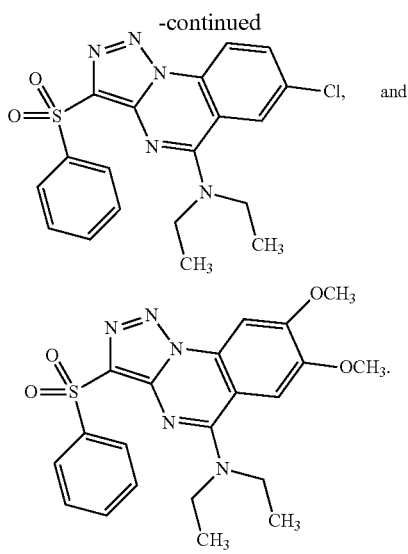

-continued

Another aspect of the invention includes a pharmaceutical composition comprising a therapeutically effective amount of compound 1835F03 (targocil) or an above-mentioned Wall Teichoic Acid (WTA) biosynthesis inhibitor; and a pharmaceutically acceptable excipient. Certain embodiments comprise a Wall Teichoic Acid (WTA) biosynthesis inhibitor and a pharmaceutically acceptable excipient. In further embodiments, the WTA biosynthesis inhibitor is a TarB, TarF, TarG, TarH, or TarL inhibitor. In certain embodiments, the WTA biosynthesis inhibitor is compound 1835F03 (targocil). In further embodiments, the WTA biosynthesis inhibitor is a TarG inhibitor.

Further aspects of the invention include a method of treating bacterial infection in a subject comprising administering to a subject in need of such a treatment a therapeutically effective amount of compound 1835F03 (targocil) or an above-mentioned Wall Teichoic Acid (WTA) biosynthesis inhibitor. In certain embodiments, the subject is human. In further embodiments, the bacterial infection comprises Gram-positive bacteria. In certain embodiments, the Gram-positive bacteria is a species of Staphylococcus. In further embodiments, the Staphylococcus is S. aureus. In certain embodiments, the S. aureus is Methicillin-resistant (MRSA).

According to another aspect of the invention, methods for suppressing Gram-positive bacterial cell growth are provided. The methods include contacting at least one Gram-positive bacterial cell with an effective amount of a Wall Teichoic Acid (WTA) biosynthesis inhibitor to suppress Gram-positive bacterial cell growth. In some embodiments, the at least one Gram-positive bacterial cell is a Staphylococcus aureus bacterial cell. In certain embodiments, the WTA biosynthesis inhibitor is a TarB, TarF, TarG, TarH, or TarL inhibitor. In some embodiments, the WTA biosynthesis inhibitor is a TarG inhibitor. In some embodiments, the WTA biosynthesis inhibitor is compound 1835F03 (targocil).

According to another aspect of the invention, kits for treating a Gram-positive bacterial infection in a subject are provided. The kits include a first container comprising a Wall Teichoic Acid (WTA) biosynthesis inhibitor or a pharmaceutical composition thereof and instructions for administration of the WTA biosynthesis inhibitor.

According to yet another aspect of the invention, methods for identifying an antibacterial therapeutic agent are provided. The methods include contacting a Gram-positive bacterial cell with a candidate agent, and determining whether the candidate agent inhibits TarG function, wherein if the candidate agent inhibits TarG function, the candidate agent is identified as an antibacterial therapeutic agent. In some embodiments, the Gram-positive bacterial cell is Staphylococcus aureus.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

FIGS. 15(A and B) shows structure activity relationships (SAR) of targocil and targocil analogs

FIG. 19 shows (Left panel) Phage infection requires WTA expression. Tunicamycin causes a dose-dependent decrease in phage infection (PFUs). (Right panel) PAGE analysis of WTAs isolated from *S. aureus* RN4220 grown in increasing but sub-lethal concentrations of a TarO inhibitor, tunicamycin, reveals a dose-dependent decrease in WTA biosynthesis.

FIG. 22 shows photographs of agar lawns of different *S. aureus* strains plated after exposure to *S. aureus* phage Φ11. Phage infection is dependent on WTA expression.

FIG. 25 shows the bacterial strains used in this work

FIG. 26 shows the plasmids and primers used in this work

DEFINITIONS

Figure 1:
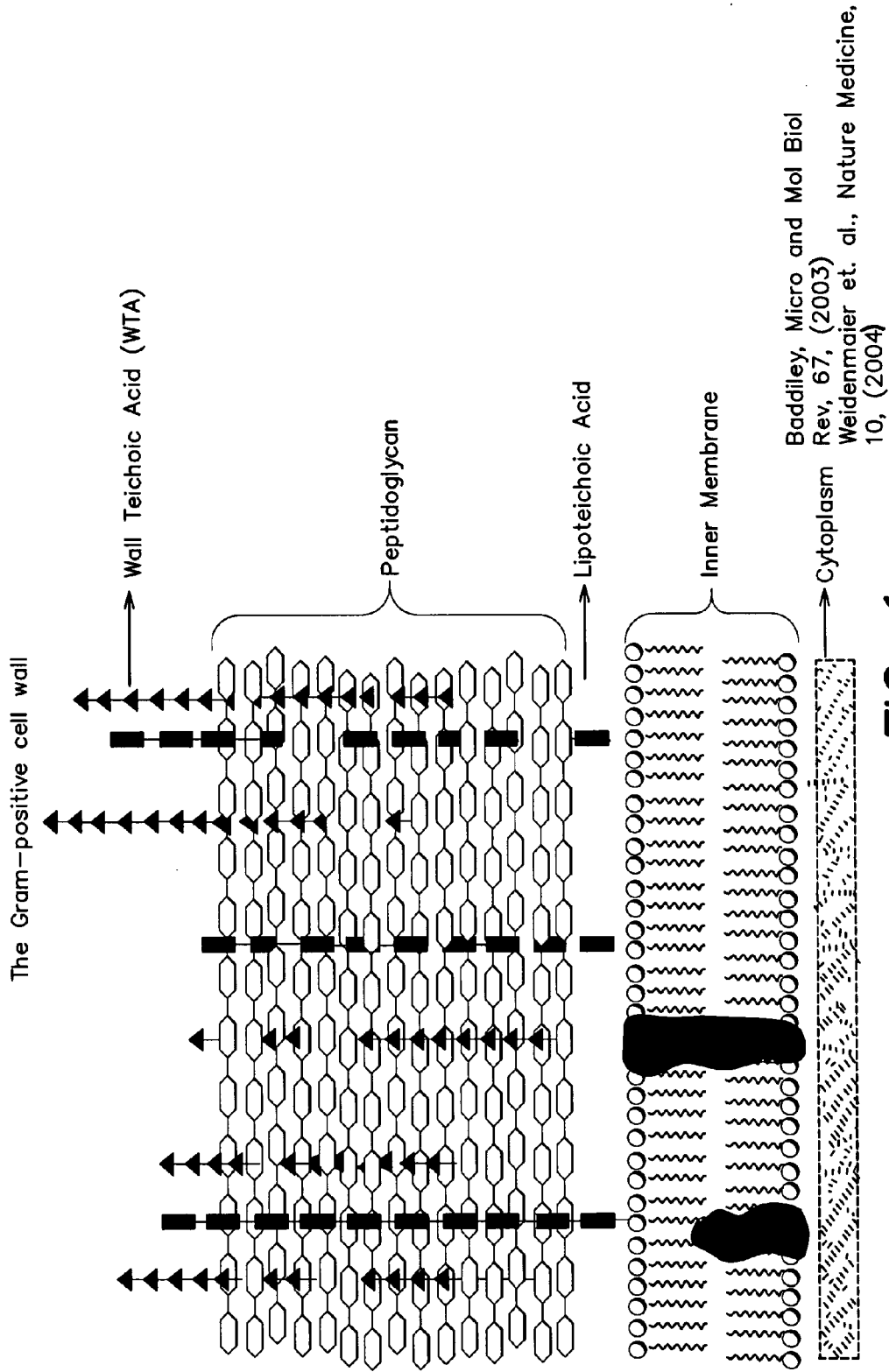
FIG. 1 is an illustration of the Gram-positive cell wall.
Figure 2:
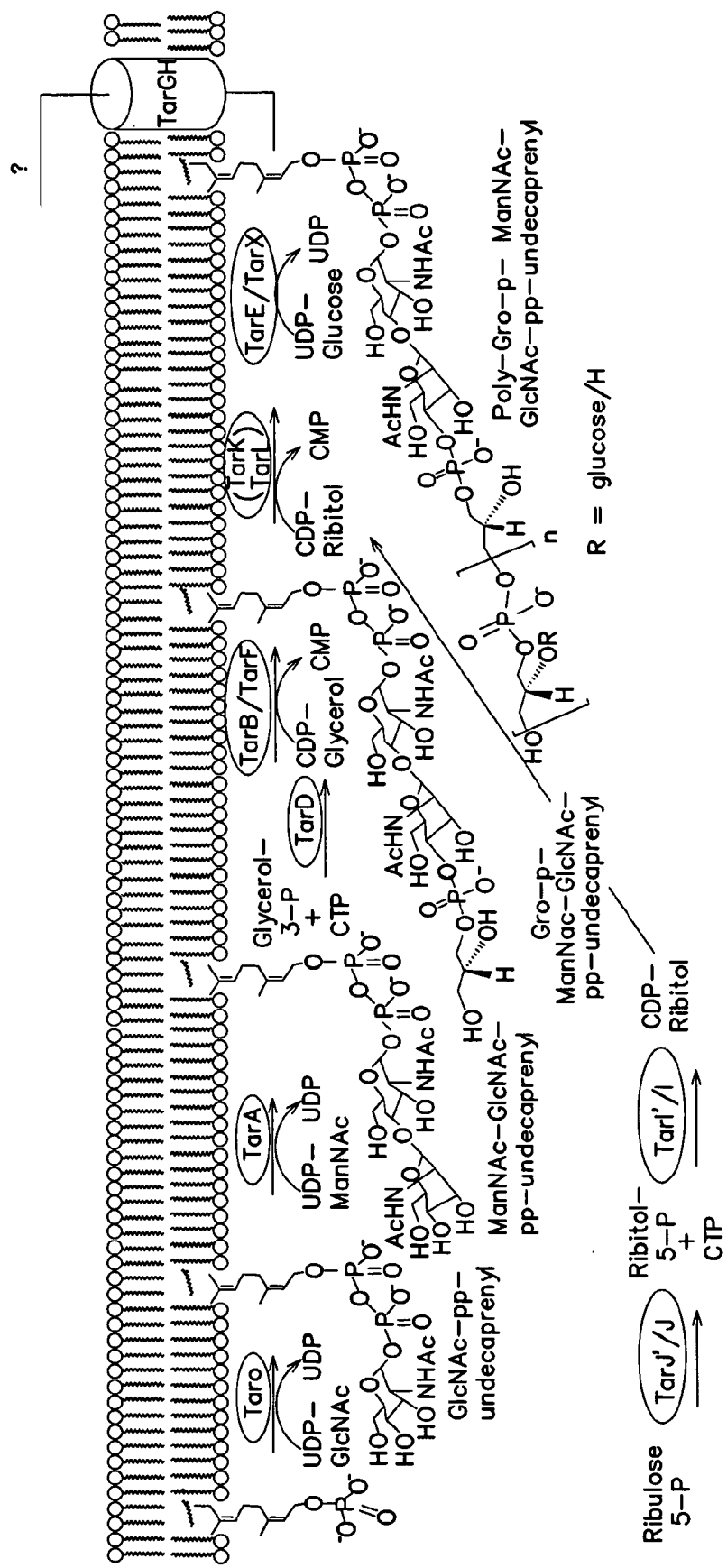
FIG. 2 shows a Wall Teichoic Acids (WTA) synthesis pathway.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substitutents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

The term "acyl," as used herein, refers to a group having the general formula $-C(=O)R^{X1}$, $-C(=O)OR^{X1}$, $-C(=O)-O-C(=O)R^{X1}$, $-C(=O)SR^{X1}$, $-C(=O)N(R^{X1})_2$, $-C(=S)R^{X1}$, $-C(=S)N(R^{X1})_2$, and $-C(=S)S(R^{X1})$, $-C(=NR^{X1})R^{X1}$, $-C(=NR^{X1})OR^{X1}$, $-C(=NR^{X1})SR^{X1}$, and $-C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes ($-CHO$), carboxylic acids ($-CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more sustitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula ($—NH_2$). A "substituted amino" refers either to a mono-substituted amine ($—NHR^h$) of a disubstituted amine ($—NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group ($—NR^h_2$) form a 5- to 6-membered hetereocyclic ring.

The term "alkoxy" refers to a "substituted hydroxyl" of the formula ($—OR^i$), wherein $R^i$ is an optionally substituted alkyl group, as defined herein, and the oxygen moiety is directly attached to the parent molecule.

The term "alkylamino" refers to a "substituted amino" of the formula ($—NR^h_2$), wherein $R^h$ is, independently, a hydrogen or an optionally substituted alkyl group, as defined herein, and the nitrogen moiety is directly attached to the parent molecule.

The term "dialkylamino" refers to a "substituted amino" of the formula ($—NR^h_2$), wherein each $R^h$ is an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "cyano," as used herein, refers to a group of the formula (—CN).

The term "nitro," as used herein, refers to a group of the formula (—$NO_2$).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—$NR^h_2$), wherein $R^h$ is, independently, a hydrogen or an optionally substituted heteroalkyl group, as defined herein, and the nitrogen moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "hydroxy," or "hydroxyl," as used herein, refers to a group of the formula (—OH). A "substituted hydroxyl" refers to a group of the formula (—$OR^i$), wherein $R^i$ can be any substitutent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "oxo," as used herein, refers to a group of the formula (=O).

The term "stable moiety," as used herein, preferably refers to a moiety which possess stability sufficient to allow manufacture, and which maintains its integrity for a sufficient period of time to be useful for the purposes detailed herein.

A "protecting group" as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

A "suitable amino protecting group," as used herein, is well known in the art and includes those described in detail in Greene (1999). Suitable amino protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylypethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group" as used herein, is well known in the art and include those described in detail in Greene (1999). Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate(levulinate), 4,4-(ethylenedithio)pentanoate(levulinoyldithioacetal), pivaloate, adamantoate, crotonate, 4-methoxycrotonate, benzoate, p-phenylbenzoate, 2,4,6-trimethylbenzoate(mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

As used herein, the term "pharmaceutically acceptable salt" refers to those salts which are, within the scope of sound medical judgment, suitable for use in contact with the tissues of humans and lower animals without undue toxicity, irritation, immunological response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The terms "administer," "administering," or "administration," as used herein refers to implanting, absorbing, ingesting, injecting, or inhaling the inventive compound.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of an individual's exposure to an infectious organism). Treatment may also be continued after symptoms have resolved, for example to prevent or delay their recurrence.

As used herein, the term "subject" means any animal, including mammals, reptiles, birds and fish. Mammals include but are not limited to: humans, non-human primates, cats, dogs, sheep, pigs, horses, cows, rodents such as mice, rats, etc. In some embodiments, a subject is a mammal that is in need of treatment with a WTA biosynthesis inhibitor. Some embodiments of the invention provide methods and compositions described here are useful for treating of Gram-positive bacterial infections in a subject, including human subjects and for veterinary treatment of other animals that are subject to Gram-positive bacterial infection. Cells treated by contacting with a WTA biosynthesis inhibitor of the invention may also include cells in culture. A cell or population of cells with a Gram-positive bacterial infection may be contacted with an WTA biosynthesis inhibitor compound of the invention outside of a subject as a treatment for a Gram-positive bacterial infection.

As used herein the term "inhibit" with reference to WTA biosynthesis or bacterial cell growth, means to reduce the amount of WTA biosynthesis or bacterial cell growth to a level or amount that is statistically significantly less than an control level. A control level may be the initial level of WTA biosynthesis or bacterial cell growth. As used herein, a control level may be a level in a cell, tissue, or subject not contacted with a WTA biosynthesis inhibitor. Thus, in some embodiments, a control level is a level of bacterial growth in a subject or preparation that is not contacted with a WTA biosynthesis inhibitor. In some cases, a decrease in the level of WTA biosynthesis or bacterial cell growth in a subject or preparation compared to a control level means that contact with the WTA biosynthesis inhibitor resulted in a reduction of the level of WTA biosynthesis or bacterial cell growth from an initial level to a level significantly lower than the initial level. In some cases, the reduced level may be zero.

An "effective amount" is that amount of a WTA biosynthesis inhibitor or a pharmaceutical composition comprising a WTA biosynthesis inhibitor that alone, or together with further doses, stimulates the desired response. In the case of treating a bacterial infection, the desired response is reducing the onset, stage or progression of the bacterial infection and associated effects. This may involve only slowing the progression of the infection temporarily, although more preferably, it involves halting the progression of the infection permanently. An effective amount for treating bacterial infection is that amount that alters (e.g., reduces) the amount or level of bacterial infection, when the cell or subject is a cell or subject with bacterial infection, with respect to that amount that would occur in the absence of the active compound.

The term "pharmaceutically acceptable" excipient means a non-toxic material that does not interfere with the effectiveness of the biological activity of the active ingredients. The characteristics of the excipient will depend on the route of administration.

The term "vital organ system" includes the circulatory system, digestive system, endocrine system, integumentary system, lymphatic system, muscular system, nervous system, reproductive system, respiratory system, skeletal system, and urinary system. Components of each of the above-mentioned systems are well known to those of skill in the art.

DETAILED DESCRIPTION OF THE INVENTION

The invention is based at least in part upon the surprising discovery by the inventors that the inhibition of wall WTA biosynthesis potentially disrupts critical virulence factors in Gram-positive bacteria. Further, the invention is based at least in part upon the development of a high throughput screening procedure of candidate agents that can act as inhibitors against the various enzymes of the WTA pathway. Such inhibitors demonstrated antibiotic activity against Gram-positive bacteria, such as *S. aureus*.

Determination that the WTA Biosynthetic Pathway is a Viable Target for the Development of Antimicrobials The Wall Teichoic Acid (WTA) biosynthesis pathway is found in the majority of Gram-positive bacteria, and studies with *Bacillus subtilis* have revealed that it is essential to cell viability (see e.g., C. Mauel, M. Young, P. Margot, D. Karamata, "The essential nature of teichoic acids in *Bacillus sub-*

*tilis* as revealed by insertional mutagenesis." *Mol Gen Genet* (1991) 215:388-394) The essential nature of Wall Teichoic Acid may be due to the covalent attachment that it forms with peptidoglycan. Wall Teichoic Acid, like peptidoglycan, is synthesized at the outer surface of the cell membrane using a nucleotide precursor (CDP-glycerol) as the building block. Teichoic acid is a polymer of polyglycerolphosphate that is covalently attached to the peptidoglycan of Gram-positive bacteria (see FIG. 1).

As depicted in FIG. 17A, the primary *S. aureus* WTAs are assembled on a excipient lipid (undecaprenyl pyrophosphate) embedded within the cytoplasmic membrane by the sequential addition of two sugars (mediated by TarO and TarA), two glycerol 3-phosphate units (mediated by TarB and TarF), and finally the polyribitolphosphate repeat (mediated by TarL). (Brown S, Zhang Y H, & Walker S (2008) *Chemistry & Biology* 15:12-21; Meredith T C, Swoboda J G, & Walker S (2008) *Journal Of Bacteriology* 190:3046-3056) They are then exported through an ABC transporter TarG/TarH complex to the external surface of the membrane where the polymer is attached to peptidoglycan by an unidentified ligase. (Endl J, Seidl H P, Fiedler F, & Schleifer K H (1983) *Archives of Microbiology* 135:215-223) The *S. aureus* WTA pathway is analogous to the WTA biosynthesis pathway found in *B. subtilis*, with proteins annotated TagA, TagB, etc.

It should be appreciated that the terms TarG and TarG/TarH complex may be used interchangeably herein. Thus, in some embodiments an inhibitor of TarG is an inhibitor of the TarG/TarH complex. It should also be appreciated that the two terms 1835F03 and targocil are used interchangeably herein to describe the same inhibitor compound.

Figure 3:
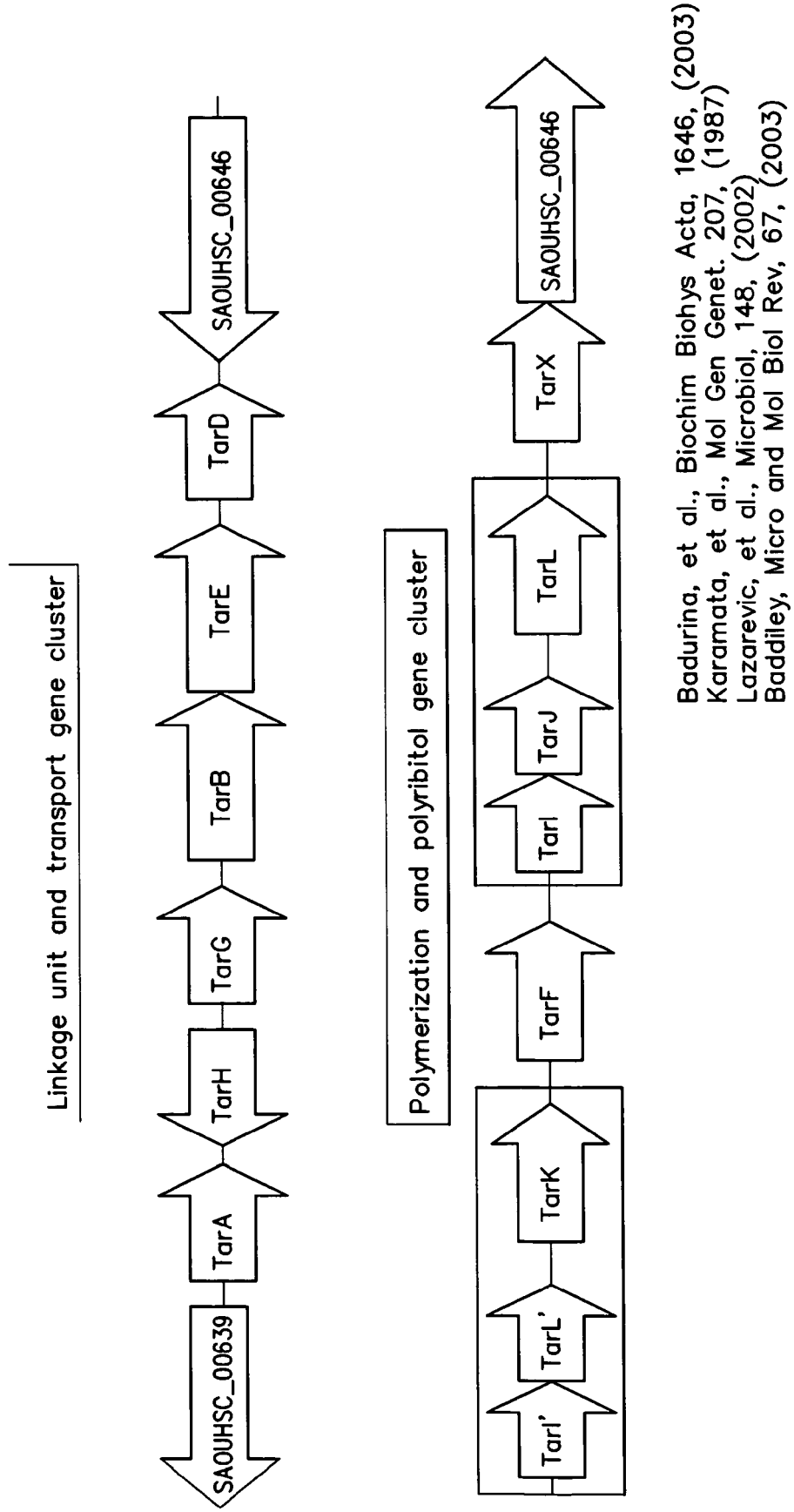
FIG. 3 shows the WTA gene cluster of S. aureus.
Figure 4:
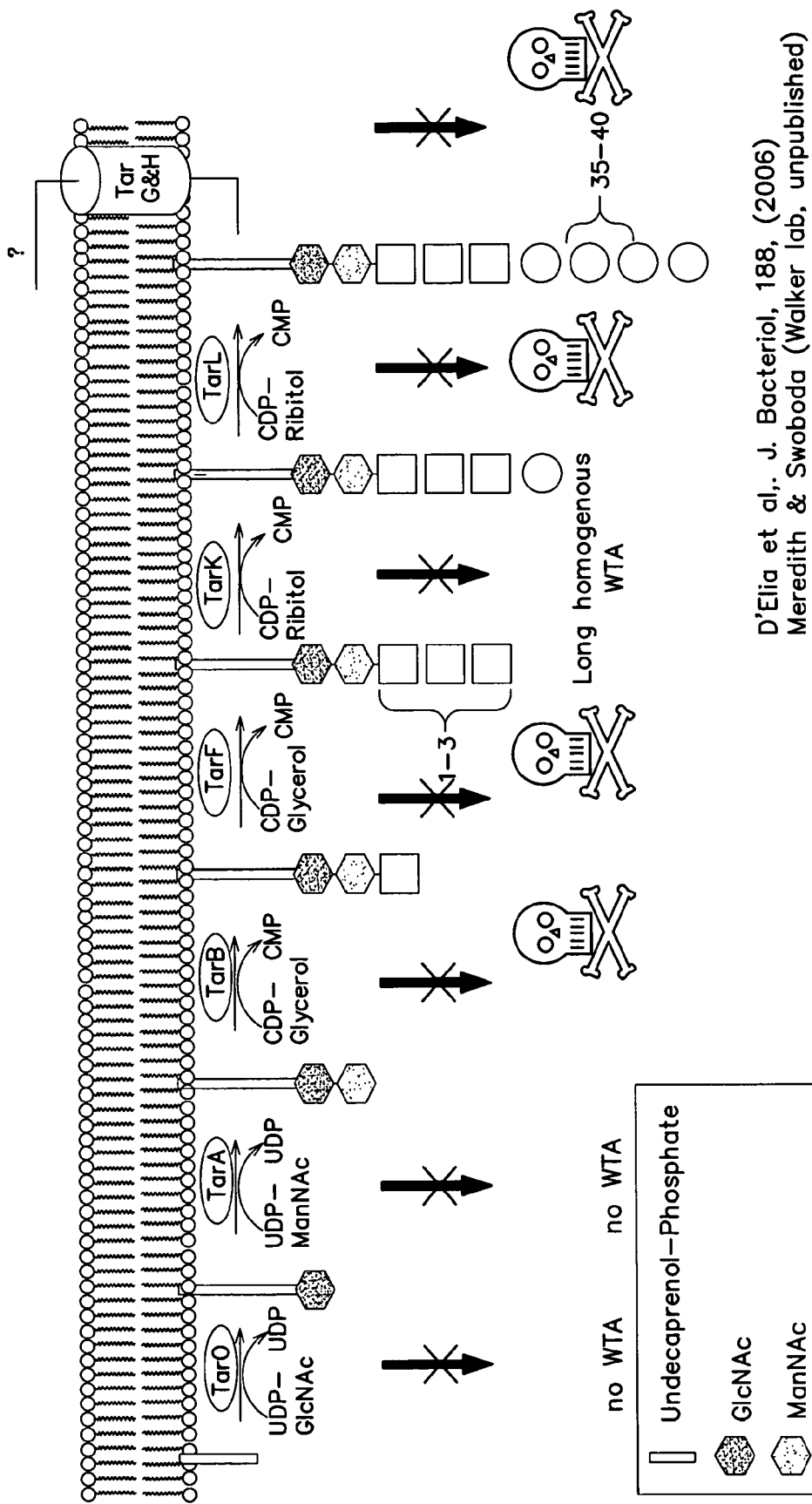
FIG. 4 shows selected phenotypes of gene deletion constructs in the WTA pathway.
Figure 5:
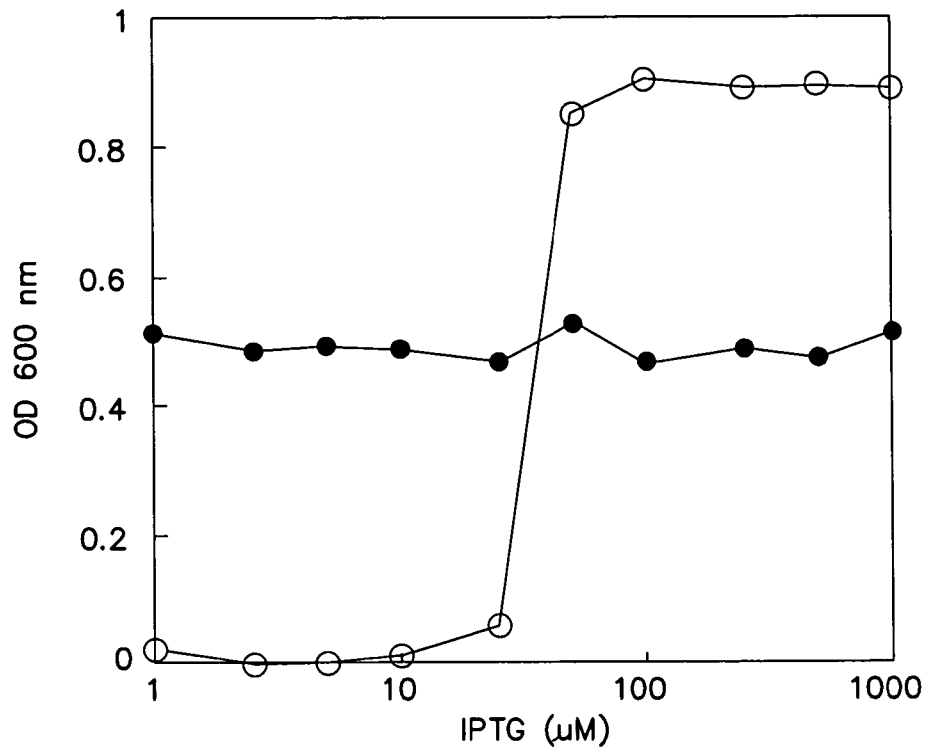
FIG. 5 shows the effect of ectopic tarL expression coupled with gene deletion of the wildtype allele.
Figure 6:
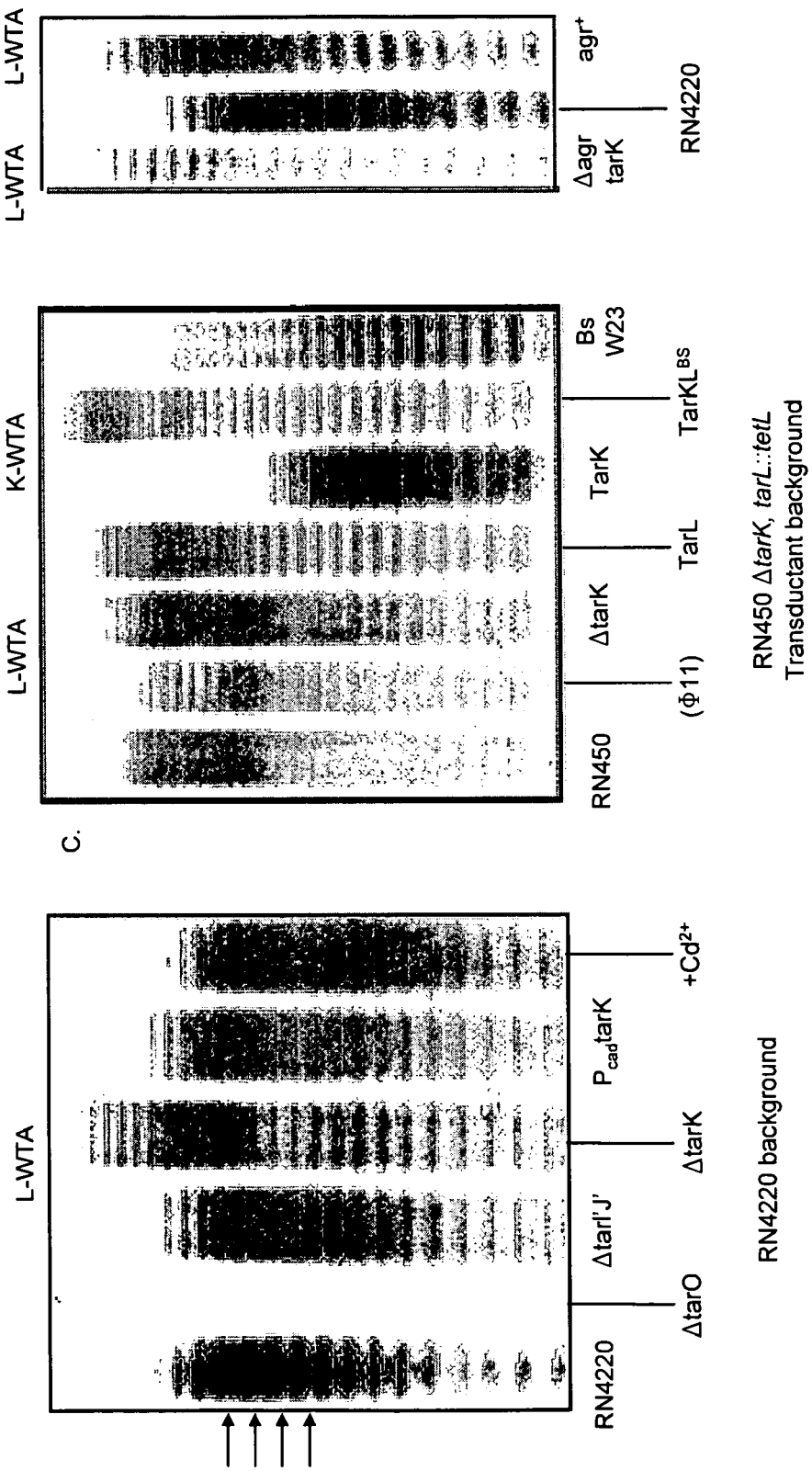
FIG. 6 shows the WTA analysis of gene deletion mutants.
Figure 7:
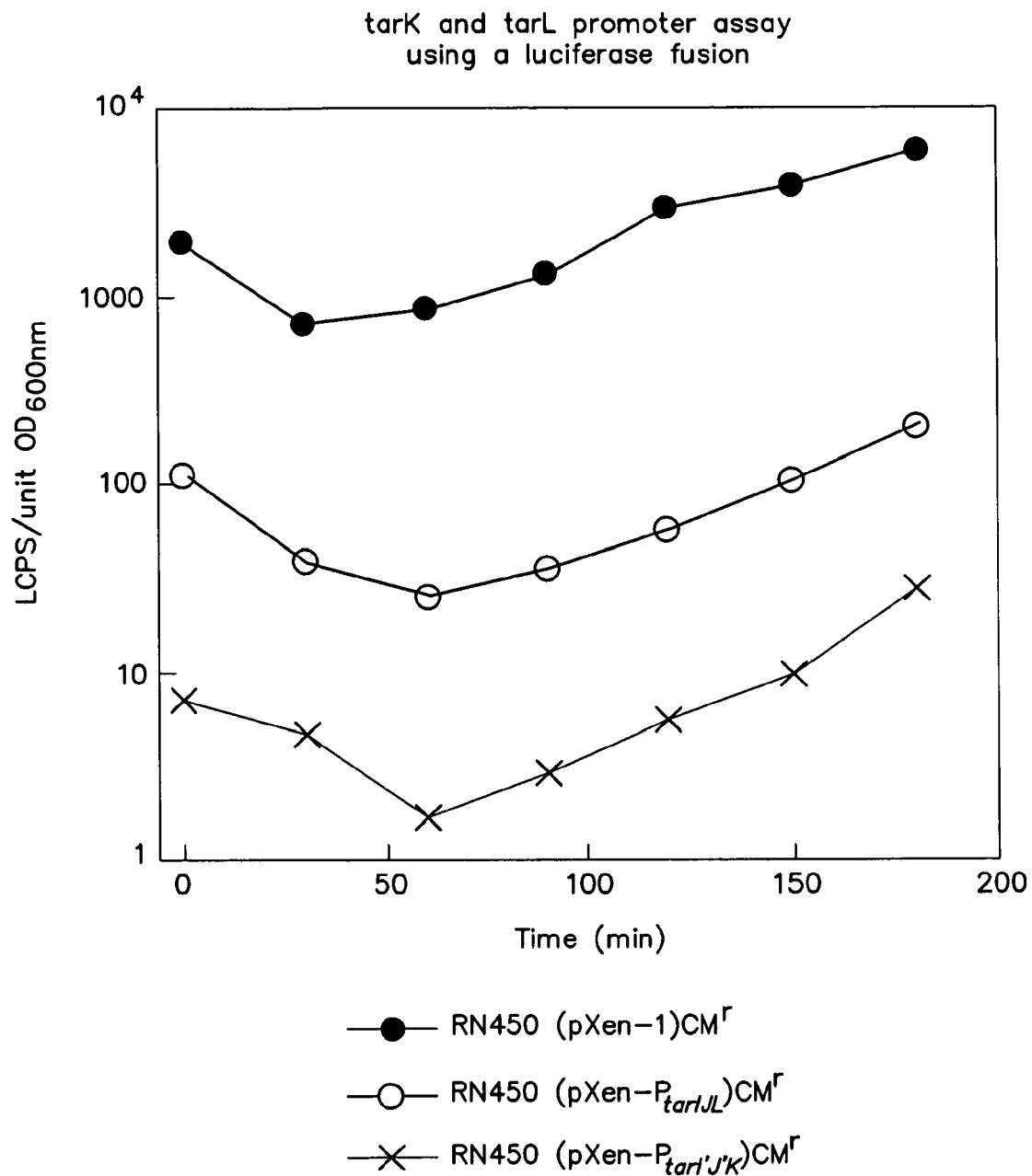
FIG. 7 shows the tarK and tarL promoter assay using a luciferase fusion.
Figure 8:
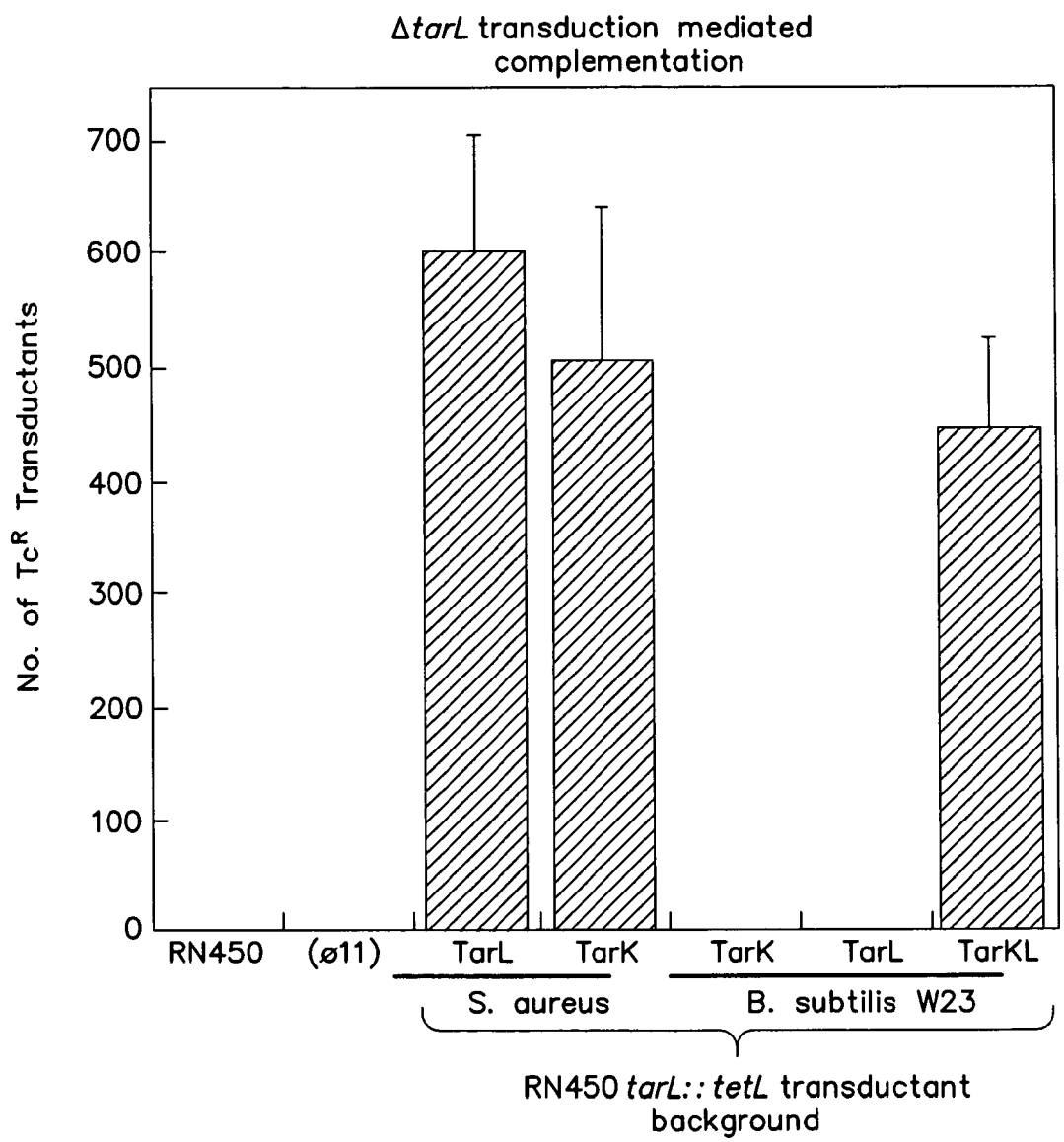
FIG. 8 shows ΔtarL transduction mediated complementation.
Figure 9:
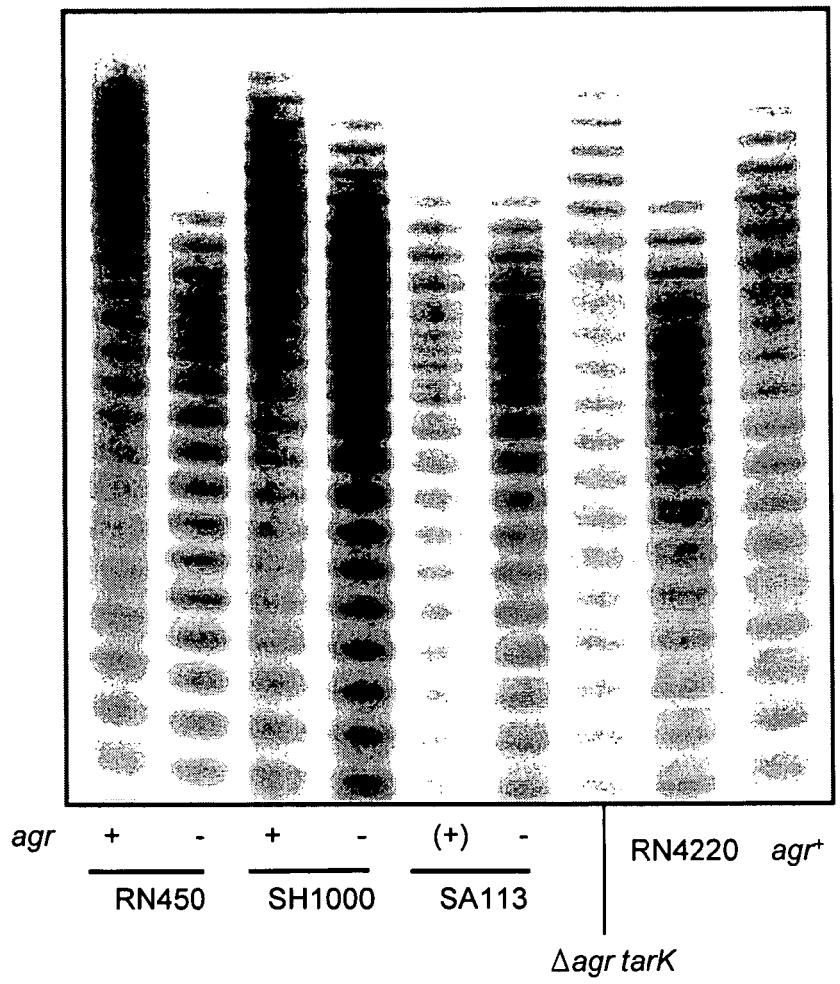
FIG. 9 shows that the quorum sensing agr system influences WTA length through TarK.
Figure 10:
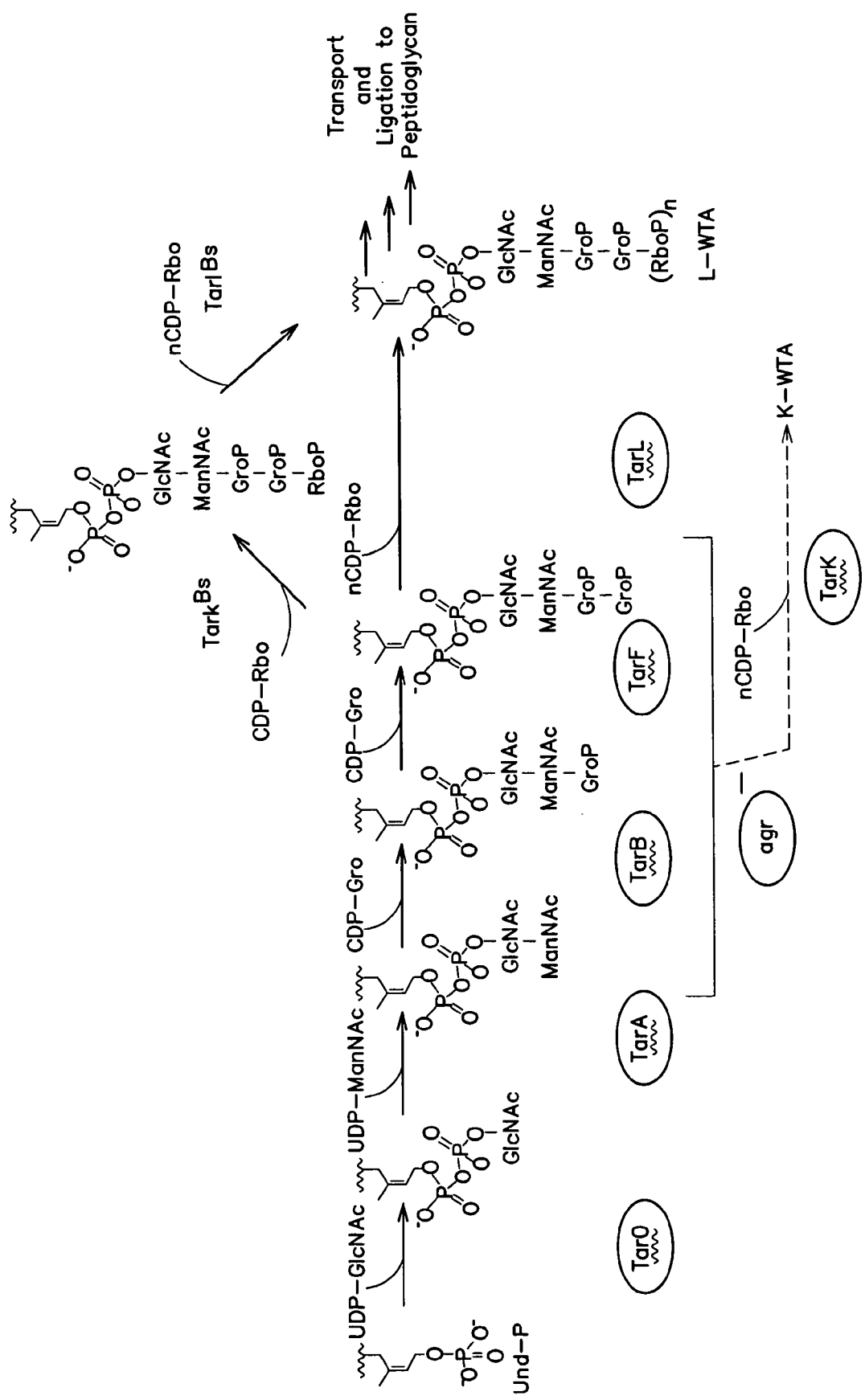
FIG. 10 shows a WTA biosynthetic pathway.
Figure 11:
FIG. 11 shows a screening process for WTA essential gene product inhibitors.

The enzymes involved in WTA biosynthesis in *S. aureus* have been identified. (see e.g., Brown et al., (2008) *Chem. & Biol.* 15, 12-21) The WTA biosynthesis pathway gene of *S. aureus* is defined by two ~3.4 kb gene clusters that have been found in all analyzed *S. aureus* strains. (Badurina et al., (2003) *Biochim Biohys Acta*, 1646; Karamata et al., (1987) *Mol Gen Genet.* 207; Lazarevic et al., (2002) *Microbiol.*, 148; Baddiley, (2003) *Micro and Mol Biol Rev*, 67; see also FIG. 3) Using a double crossover allelic replacement strategy with antisense secY counter-selection, in-frame deletions have been constructed in tarO, tarA, tarK, tarI'J', tarE, tarX, and tarEX. No viable constructs were attained in any of the other tar genes, suggesting that the accumulation of WTA precursors may perturb the integrity of the cell envelope. (Weidenmaier et. al., (2004) *Nature Medicine*, 10; D'Elia et al., (2006) *J. Bacteriol*, 188; see also FIG. 4) Inhibitors of TarB, TarF, TarG, TarH and TarL interfere with bacterial cell wall synthesis and are potential antibacterial therapeutic agents.

Figure 17:
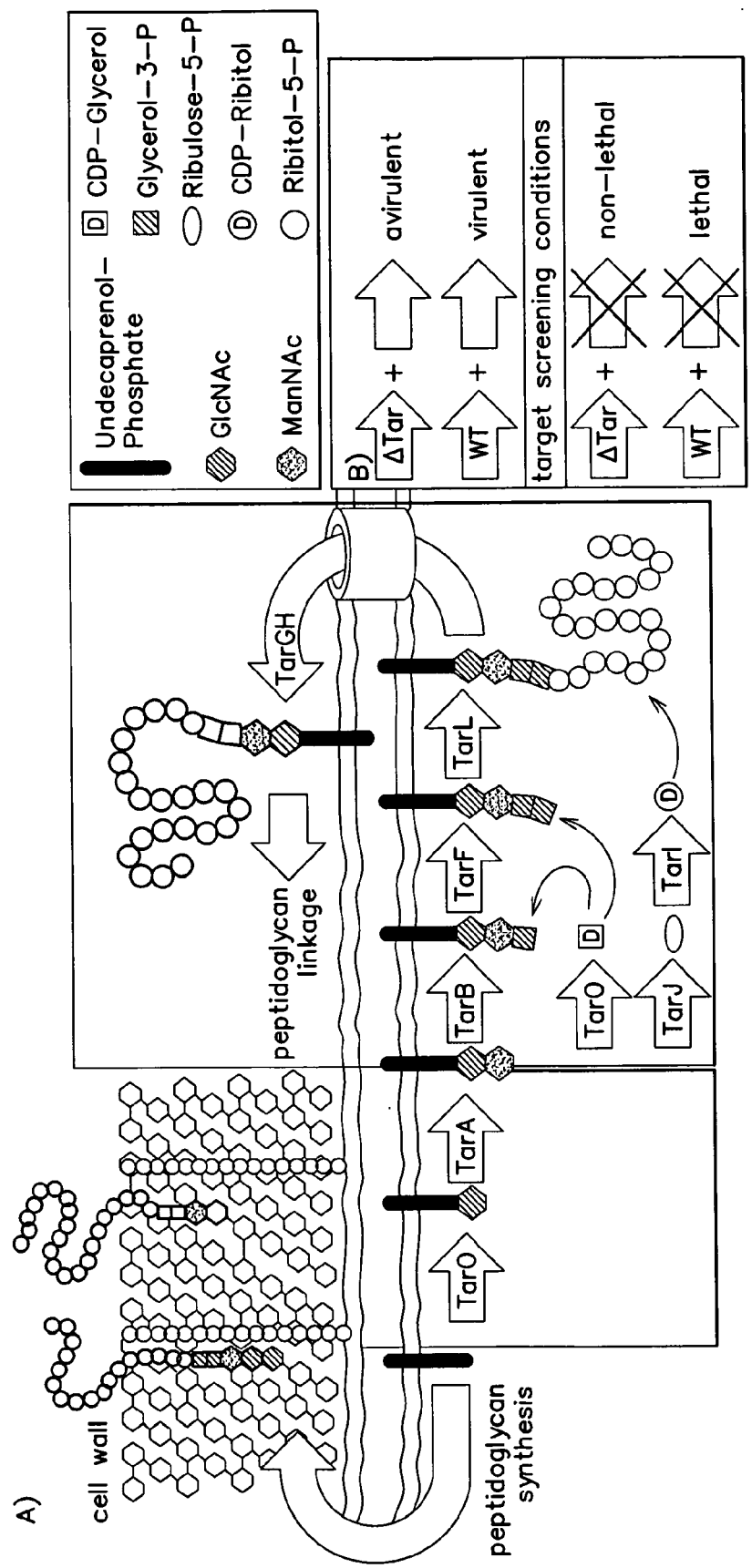
FIG. 17 shows a (A) schematic of the primary *Staphylococcus aureus* Wall Teichoic Acid biosynthetic pathway (Brown S, Zhang Y H, & Walker S (2008) *Chemistry & Biology* 15:12-21; Meredith T C, Swoboda J G, & Walker S (2008) *Journal Of Bacteriology* 190:3046-3056). Following intracellular assembly, the polyribitol-phosphate polymer is transported to the outside of the cell by a two component ABC transporter, TarGH, and is then covalently linked through a phosphodiester bond to the MurNAc sugars of peptidoglycan by an unidentified enzyme. (Neuhaus F C & Baddiley J (2003) *Microbiology and Molecular Biology Reviews* 67:686-+; Endl J, Seidl H P, Fiedler F, & Schleifer K H (1983) *Archives of Microbiology* 135:215-223; Ward J B (1981) *Microbiological Reviews* 45:211-243) Non-essential WTA pathway enzymes are TarO and TarA and their deletion leads to an avirulent phenotype. Conditionally essential enzymes are TarB, TarD, TarJ, TarI, TarF, TarL, and TarGH and their deletion is lethal in a wildtype background but permitted in a ΔtarO or ΔtarA background (Weidenmaier C, Kokai-Kun J F, Kristian S A, Chanturiya T, Kalbacher H, Gross M, Nicholson G, Neumeister B, Mond J J, & Peschel A (2004) *Nature Medicine* 10:243-245; D'Elia M A, Pereira M P, Chung Y S, Zhao W J, Chau A, Kenney T J, Sulavik M C, Black T A, & Brown E D (2006) *Journal Of Bacteriology* 188:4183-4189) (We presume that TarA's non-essentiality is due to the reversibility of TarO.) The tailoring enzymes that modify ribitol hydroxyls are omitted for clarity. (Neuhaus F C & Baddiley J (2003) *Microbiology and Molecular Biology Reviews* 67:686) In addition to TarI, J, and L, all *S. aureus* strains contain a homologous set of enzymes designated TarI', J' and K, that direct the synthesis of a distinct WTA polymer, whose cellular functions remain incompletely understood. (Meredith T C, Swoboda J G, & Walker S (2008) *Journal Of Bacteriology* 190:3046-3056; Pereira M P, D'Elia M A, Troczynska J, & Brown E D (2008) *Journal Of Bacteriology* 190:5642-5649) In *S. aureus* strain NCTC8325, the secondary WTA (K-WTA) is in part regulated by the accessory gene regulator (agr) quorum sensing system. (Meredith T C, Swoboda J G, & Walker S (2008) *Journal Of Bacteriology* 190: 3046-3056) (B) Conceptual basis for the pathway-specific, high-throughput screen. The screen identifies inhibitors of conditionally essential WTA enzymes because they inhibit the growth of the wildtype strain but not the ΔtarO strain.

The Conceptual Basis for a Cell-Based Pathway-Specific Screen for WTA Inhibitors The biosynthesis of Wall Teichoic Acids (WTA) in *S. aureus* and other Gram-positive organisms is a possible, but unvalidated antibiotic target. (Weidenmaier C, Kokai-Kun J F, Kulauzovic E, Kohler T, Thumm G, Stoll H, Gotz F, & Peschel A (2008) *International Journal of Medical Microbiology* 298:505-513; Ohlsen K & Lorenz U (2007) *Future Microbiology* 2:655-666) WTAs are deemed nonessential for survival because the first two genes in the pathway (tarO and tarA) can be deleted (Weidenmaier C, Peschel A, Xiong Y Q, Kristian S A, Dietz K, Yeaman M R, & Bayer A S (2005) *Journal of Infectious Diseases* 191:1771-1777) abolishing WTA expression. However, strains lacking WTAs are unable to colonize host tissue and exhibit a greatly diminished capacity to establish infections in vivo. (Weidenmaier C, Kokai-Kun J F, Kulauzovic E, Kohler T, Thumm G, Stoll H, Gotz F, & Peschel A (2008) *International Journal of Medical Microbiology* 298:505-513; Weidenmaier C, Peschel A, Xiong Y Q, Kristian S A, Dietz K, Yeaman M R, & Bayer A S (2005) *Journal of Infectious Diseases* 191:1771-1777; Weidenmaier C, Kokai-Kun J F, Kristian S A, Chanturiya T, Kalbacher H, Gross M, Nicholson G, Neumeister B, Mond J J, & Peschel A (2004) *Nature Medicine* 10:243-245) Although the pathway itself is non-essential, several of the downstream WTA biosynthetic genes (tarB, D, F, G, H, I, J, and L; FIG. 17) can only be deleted in a ΔtarO or ΔtarA background. (Meredith T C, Swoboda J G, & Walker S (2008) *Journal Of Bacteriology* 190:3046-3056; D'Elia et al., 2006 *J. Bacteriol*, 188) These results imply that initiating flux into the WTA biosynthetic pathway without completing it is detrimental to cell viability. Thus, small molecule inhibitors of the conditionally essential WTA enzymes should have antibiotic activity.

Development of a HTS Screening Protocol to Identify WTA Biosynthesis Inhibitors

A pathway-specific, high throughput screen (HTS) to identify inhibitors of the conditionally essential WTA enzymes has been devised. The screen exploits the differential susceptibility of a wildtype *S. aureus* strain, RN4220, and its isogenic ΔtarO mutant strain having a deletion mutation in the first enzyme of the Wall Teichoic Acid pathway, tarO: compounds that inhibit the growth of the WTA expressing strain (wildtype), but not the ΔtarO mutant, are expected to target the conditionally essential enzymes in the WTA pathway (FIG. 17B). In the wildtype background, deletions in tarB, F, L, G and H do not lead to viable mutants. However, it is possible to make these mutations in a ΔtarO background *S. aureus* strain. (D'Elia et al. (2006) *J. Bact.* 188, 4183-4189)

Figure 12:
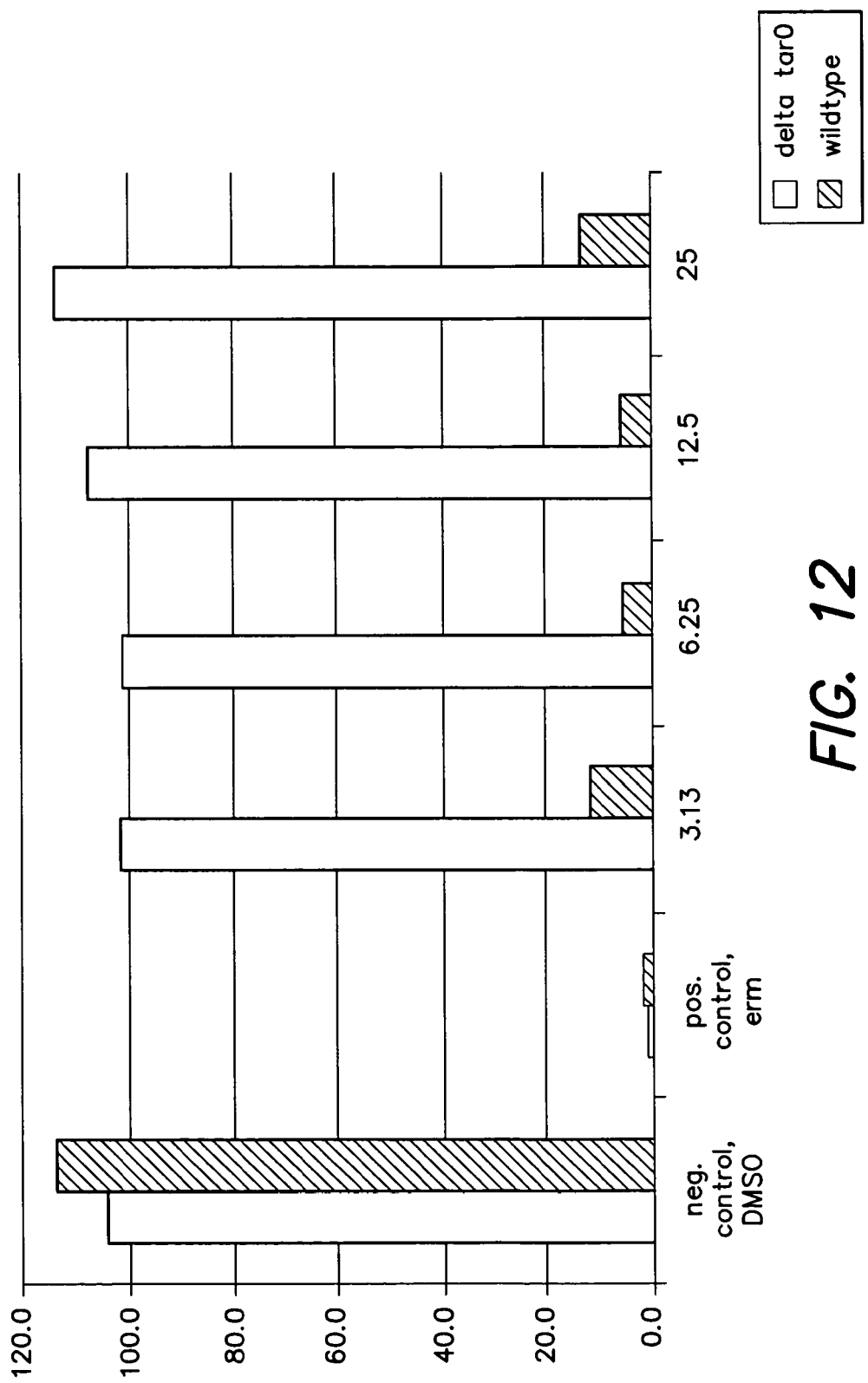
FIG. 12 shows the dose response data of a positive hit compound 1835F03 (targocil) for WTA essential gene product inhibitor. Compounds were screened in duplicate against wildtype RN4220 S. aureus and ΔtarO RN4220 S. aureus grown in separate plates. In the preliminary screen, a hit was defined as greater than 50% survival in ΔtarO and less than 10% survival in the wildtype stain % survival was normalized to the positive and negative controls on each plate.

The combination of these strains allows for high throughput screening of candidate agents that can act as inhibitors against the various enzymes of the WTA pathway, by identifying compounds that kill the wildtype, but have no lethal effect on a ΔtarO mutant. Screening the paired strains not only ensures pathway specificity, it also allows us to eliminate compounds that inhibit essential cellular processes or are toxic for other reasons. Compounds that have this effect are antibacterial therapeutic agents against enzymes of Wall Teichoic Acid biosynthesis. Once these antibacterial therapeutic agents were identified in a screen, the specific WTA target could be validated using either in vitro biochemical assays (e.g., TarB, F and L; see e.g., Brown et al., (2008) *Chemistry and Biology* 15, 12-21) or in vivo by assaying the effect of the compounds on WTA resistant mutant strains (e.g., tarG and H). An overview of this screening and validation process is presented in FIG. 12.

Figure 16A:
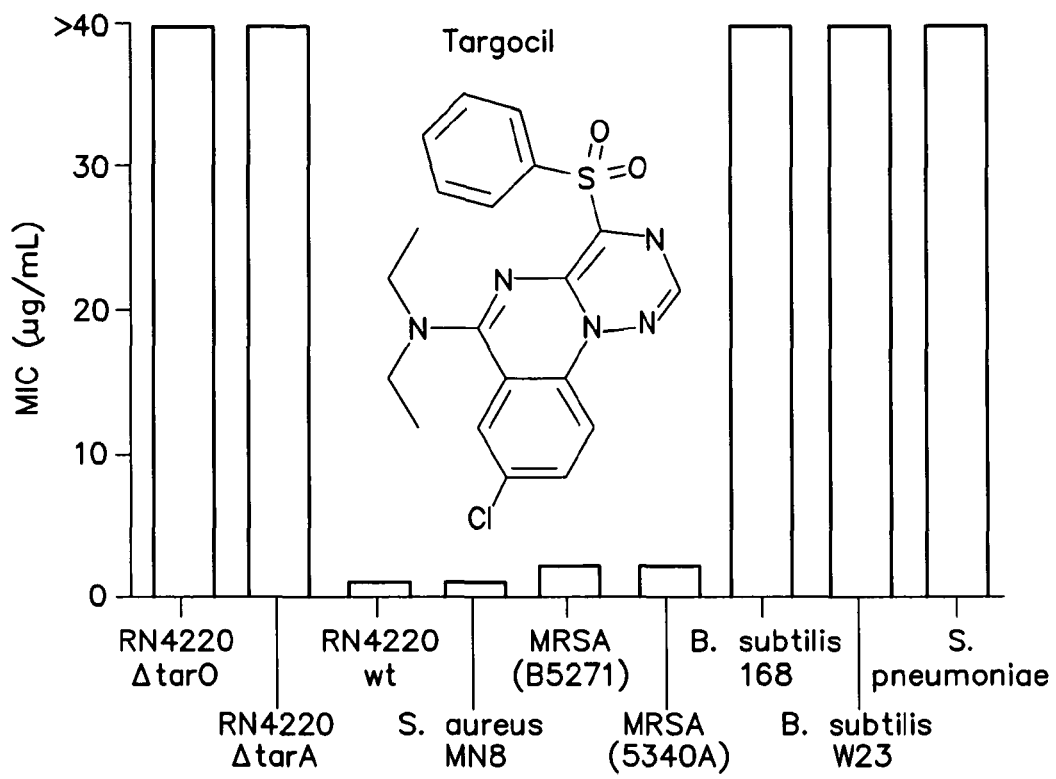
FIG. 16 shows the antibiotic activity of targocil. (A) Targocil MIC data for a panel of Gram-positive strains, including MRSA clinical isolates B5271 and 5340A. Growth was monitored in triplicate after 12 h at 28° C. using optical density. (B) Two dimensional drug interaction analysis between tunicamycin and targocil grown for 18 h at 30° C. At sub-lethal concentrations that fully inhibit TarO (10-2 μg/ml-101 μg/ml), tunicamycin antagonizes the lethal effect of targocil. At higher concentrations, tunicamycin is toxic because it inhibits cell wall biosynthesis. (C) Kill curve analysis of targocil shows a bacteriostatic mechanism. Varying concentrations of drug were added to 106 cfu/mL of *S. aureus* RN4220 after 5 h and cell count was monitored over time at 30° C. (D) Ectopic integration and overexpression of *B. subtilis* 168 tagGH, encoding a two component WTA transporter, in *S. aureus* RN4220 confers complete resistance to targocil. Similar overexpression of the *S. aureus* WTA transporter (tarGH) confers partial resistance. Cells were grown at 28° C. for 12 h and monitored for growth using optical density (OD600). Data were normalized to the DMSO controls for each strain. (E) Two classes of mutants were examined: phage resistant (m1 3) and phage sensitive (m4-5). WTA PAGE analysis of the mutants show that phage infectivity correlates with WTA expression. Strains m1, m2, and m3 were found to have null mutations (m1 has a point mutation in tarA, m2 contains a frameshift that led to a premature stop codon in tarA and m3 contains a rearrangement in tarO producing a truncated form of the protein). Strains m4 and m5 were found to contain point mutations in targocil's target, tarG. (F) RN4220 ΔtarO mutants and resistant mutants that arise after prolonged incubation in targocil (8×MIC) show attenuated virulence in a corneal epithelial internalization model. * Student t-test shows that targocil mutants are statistically different from the wildtype control; P<0.0002 (n=6).
Figure 18:
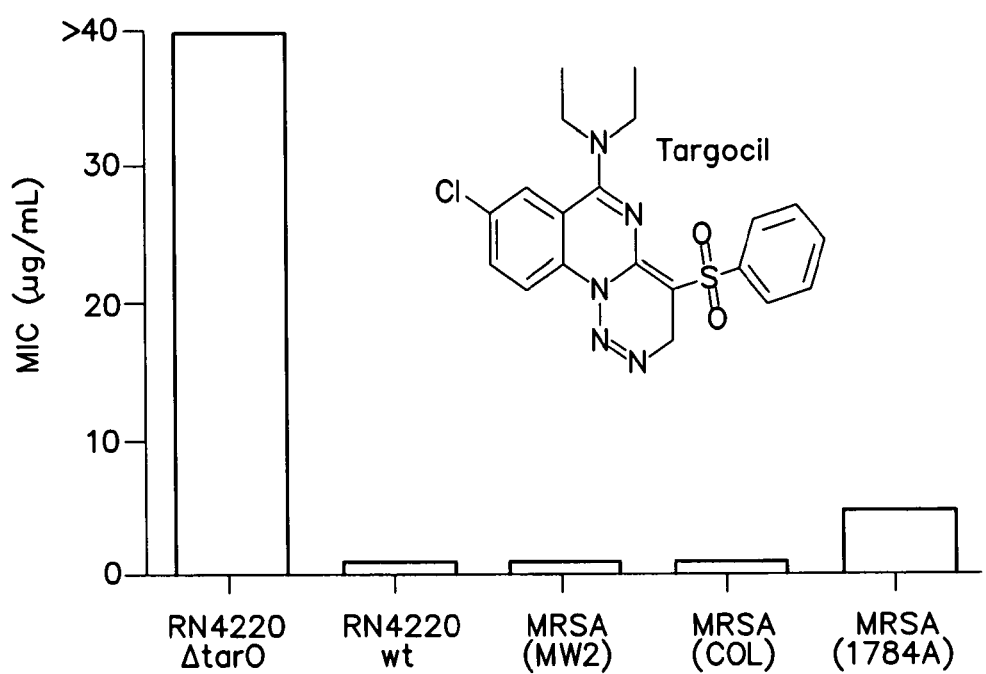
FIG. 18 shows antibiotic activity of targocil against both community- and hospital-acquired MRSA strains compared to the wildtype and ΔtarO strain. (G. Bou, (2007) *Methods Mol Biol* 391, 29)

A library of 55,000 small molecules was screened in duplicate at a concentration of ~40 μM against *S. aureus* RN4220 and the corresponding ΔtarO strain using optical density to monitor growth. We obtained 45 initial hits and confirmed three lead compounds that inhibited the growth of the wildtype strain but had no activity against the ΔtarO strain. The most potent compound, which we named targocil, had a minimum inhibitory concentration (MIC) of 1.3 μg/mL (3 μM) against wildtype *S. aureus* RN4220. The in vitro MIC values for targocil against all tested *S. aureus* strains, including five MRSA strains, were in the low μg/mL range. (FIG. 16A and FIG. 18) (Lazarevic V, Abellan F X, Moller S B, Karamata D, & Mauel C (2002) *Microbiology-Sgm* 148:815-824)

Determination of a Biological Target of WTA Biosynthesis Inhibitors

Figure 16B:
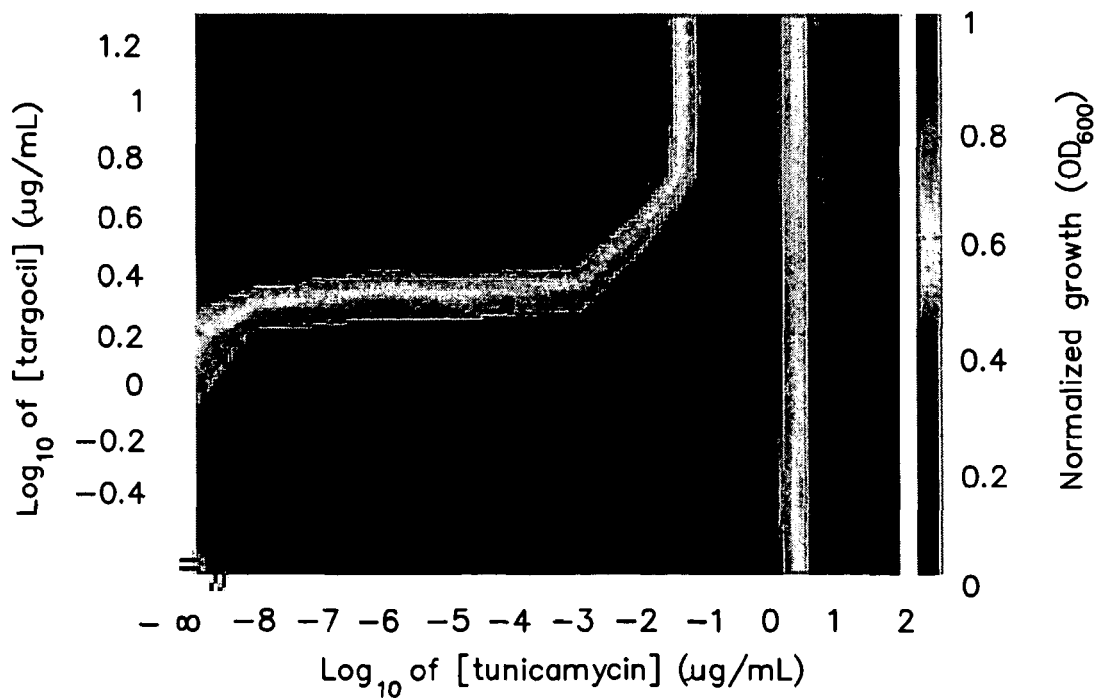
Figure 16C:
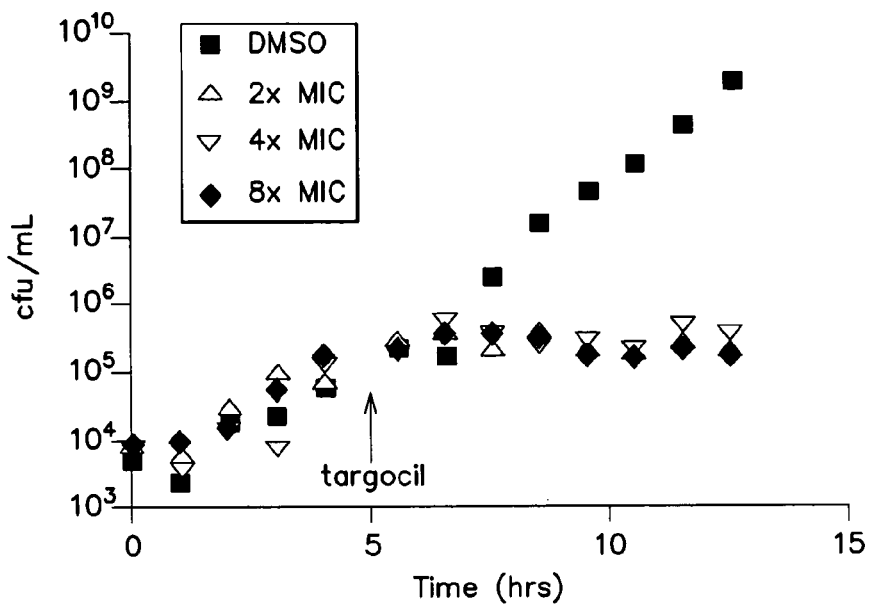
Figure 20:
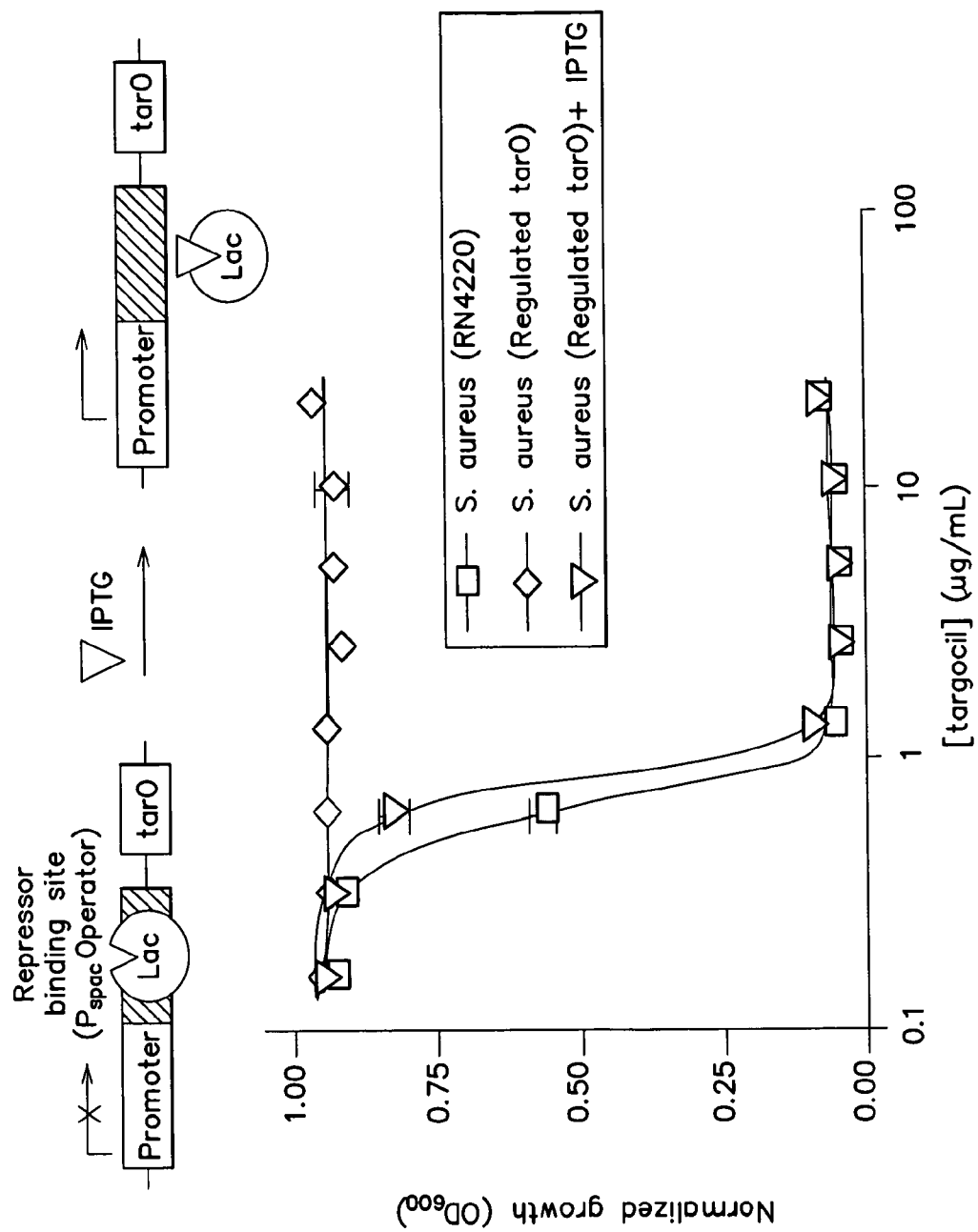
FIG. 20 shows a constructed strain of *S. aureus* that expresses taro under the control of an isopropyl β-D-1-thiogalactopyranoside (IPTG)-inducible promoter. (T. C. Meredith, J. G. Swoboda, S. Walker, (2008) *Journal Of Bacteriology* 190, 3046) In the presence of IPTG-induced WTA biosynthesis, targocil inhibited cell growth; in its absence, targocil had no effect. These results show that the antibiotic activity of targocil requires flux into the WTA biosynthetic pathway and imply that the compound inhibits one of the conditionally essential WTA enzymes. (Top) Schematic of the IPTG-inducible tarO operon. (Bottom) Growth as a function of targocil concentration for wildtype *S. aureus* RN4220 (■) and the IPTG-inducible tarO strain in the absence (♦) and presence (▼) of IPTG shows that antibiotic activity depends on taro expression. Data were normalized to the DMSO controls for each strain.
Figure 21A:
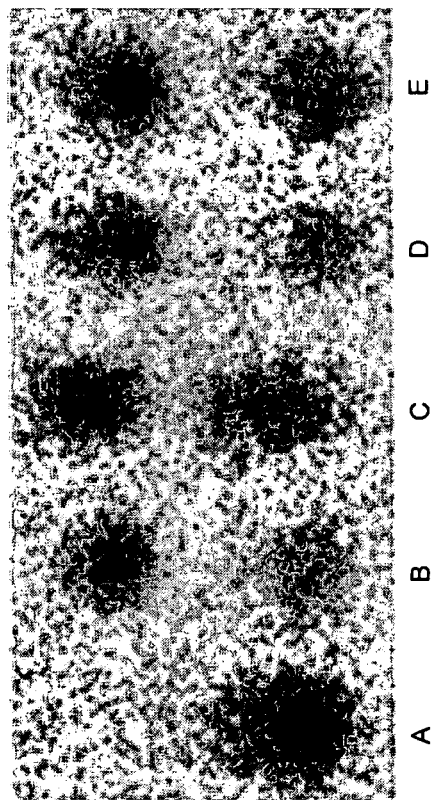
FIG. 21a shows (A-E) autoradiogram of a polyacrylamide gel for TarD reactions. (A) TarD reaction with heat-treated enzyme; (B) TarD reaction with active enzyme; (C) TarD reaction with 5 μM targocil; (D) TarD reaction with 50 μM targocil; (E) TarD reaction with 100 μM targocil.
Figure 21B:
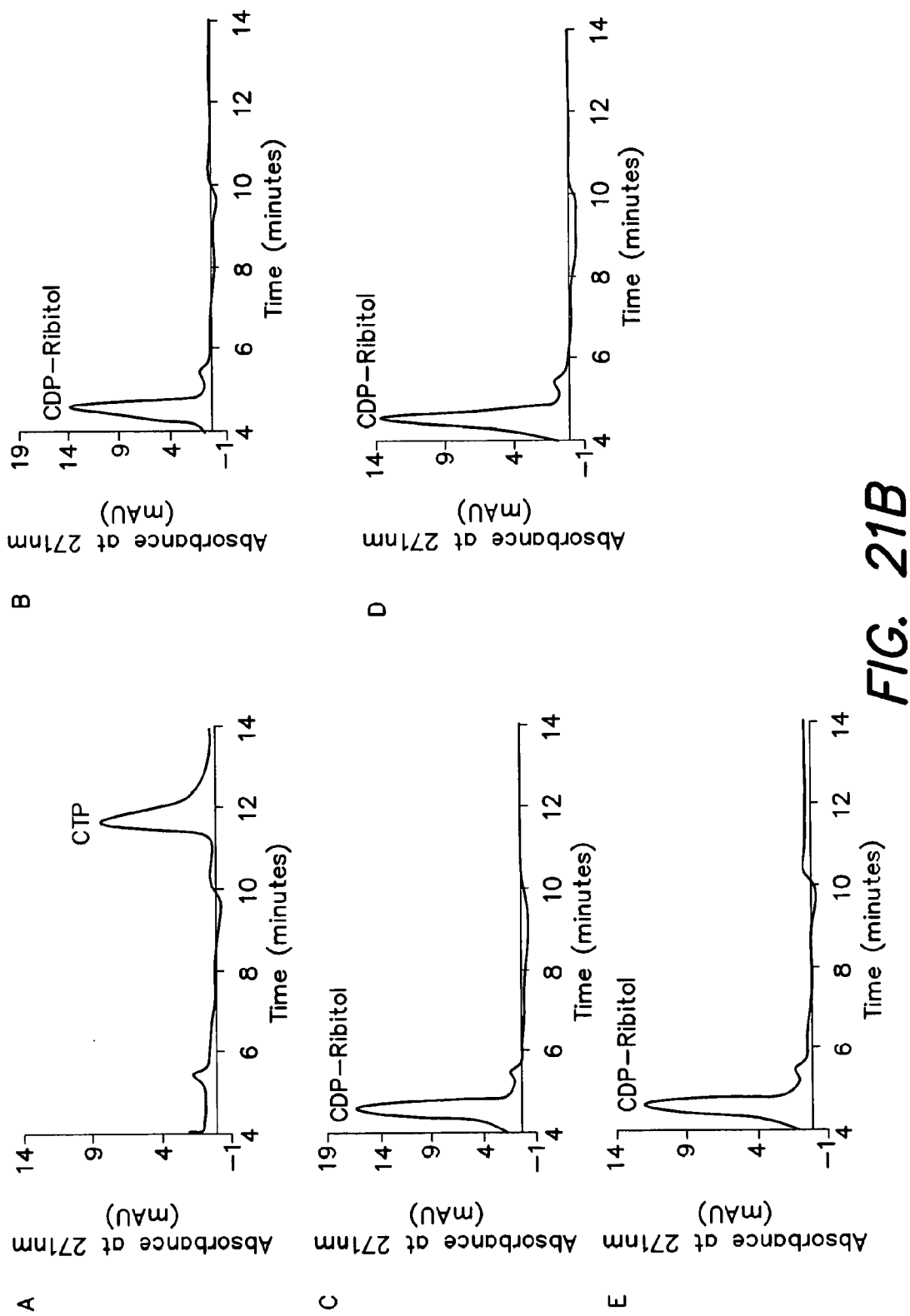
FIG. 21b shows (A-E) HPLC chromatograms for TarI reactions. (A) TarI reaction with heat-treated enzyme; (B) TarI reaction with active enzyme; (C) TarI reaction with 5 μM targocil; (D) TarI reaction with 50 μM targocil; (E) TarI reaction with 100 μM targocil.
Figure 21C:
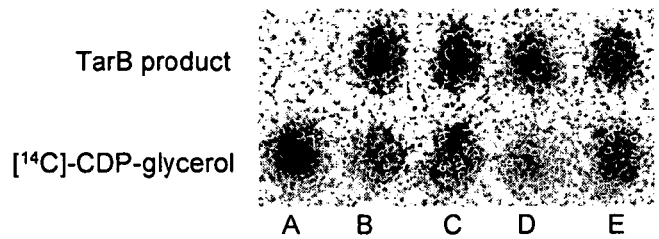
FIG. 21c shows (A-E) an autoradiogram of a polyacrylamide gel for TarB reactions. (A) TarB reaction with heat-treated enzyme; (B) TarB reaction with active enzyme; (C) TarB reaction with 5 μM targocil; (D) TarB reaction with 50 μM targocil; (E) TarB reaction with 100 μM targocil.
Figure 21D:
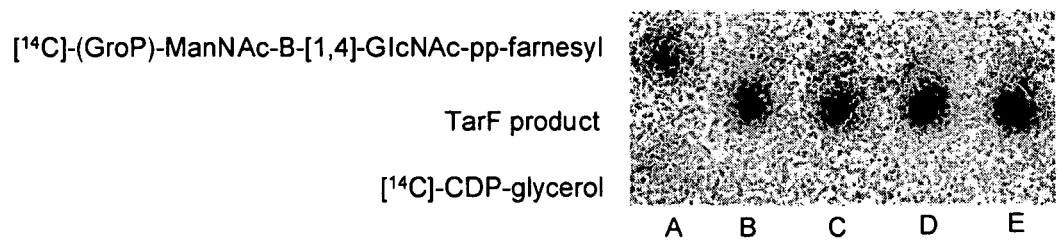
FIG. 21d shows (A-E) an autoradiogram of a polyacrylamide gel for TarF reactions. (A) TarF reaction with heat-treated enzyme; (B) TarF reaction with active enzyme; (C) TarF reaction with 5 μM targocil; (D) TarF reaction with 50 μM targocil; (E) TarF reaction with 100 μM targocil.
Figure 21E:
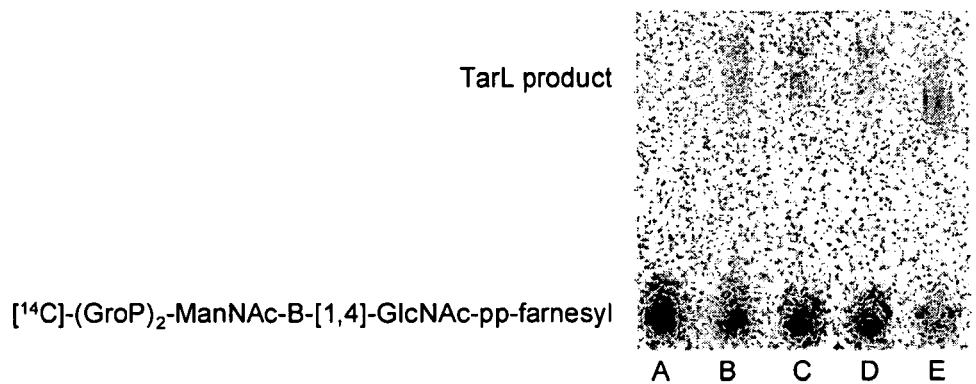
FIG. 21e shows (A-E) an autoradiogram of a polyacrylamide gel for TarL reactions. (A) TarL reaction with heat-treated enzyme; (B) TarL reaction with active enzyme; (C) TarL reaction with 5 μM targocil; (D) TarL reaction with 50 μM targocil; (E) TarL reaction with 100 μM targocil.

Having discovered targocil, the next challenge was to identify its target in *S. aureus*. We first used the natural product tunicamycin to verify that targocil requires the presence of a functional WTA pathway. Although toxic at high concentrations, tunicamycin is a selective TarO inhibitor that abolishes WTA expression at sublethal concentrations. (Hancock I C, Wiseman G, & Baddiley J (1976) *Febs Letters* 69:75-80) We predicted that tunicamycin should antagonize targocil by preventing flux into the WTA biosynthetic pathway. The growth of *S. aureus* was monitored in a two dimensional matrix of concentrations of tunicamycin and targocil (Yeh P, Tschumi A I, & Kishony R (2006) *Nature Genetics* 38:489-494.), and as expected, tunicamycin provided complete protection against normally inhibitory concentrations of targocil (FIG. 16b). We have confirmed that targocil activity requires a functional WTA pathway, genetically, using an IPTG-inducible tarO strain (FIG. 20). With targocil in hand, we were then able to probe the effects of blocking the WTA biosynthetic pathway. Kill curve analysis shows that targocil is bacteriostatic (FIG. 16c) rather than bactericidal. This finding suggests an explanation for the conditional essentiality of the downstream enzymes: flux into the WTA biosynthetic pathway leads to depletion of undecaprenyl pyrophosphate, the excipient lipid used for peptidoglycan biosynthesis, and this stops bacterial growth. An alternative hypothesis, that blocking WTA biosynthesis leads to the accumulation of toxic intermediates, is less likely since the cells cease growing but do not die.

We next tested targocil for inhibition of *S. aureus* TarB, D, F, I, J, and L, enzymes for which we have biochemical assays (Brown S, Zhang Y H, & Walker S (2008) *Chemistry & Biology* 15:12-21; Pereira M P & Brown E D (2004) *Biochemistry* 43:11802-11812.) None of these enzymes was inhibited at targocil concentrations of 50 μg/mL (FIGS. 21a-e) (Brown S, Zhang Y H, & Walker S (2008) *Chemistry & Biology* 15:12-21). These results suggested that targocil acts on either the two component ABC (ATP Binding Cassette) transporter that exports WTAs to the bacterial cell surface (TarGH) or the unidentified transferase that couples exported WTAs to peptidoglycan. Because TarGH transport activity has not been reconstituted in vitro, we used a genetic approach to determine whether this transporter is the target of targocil.

Figure 16D:
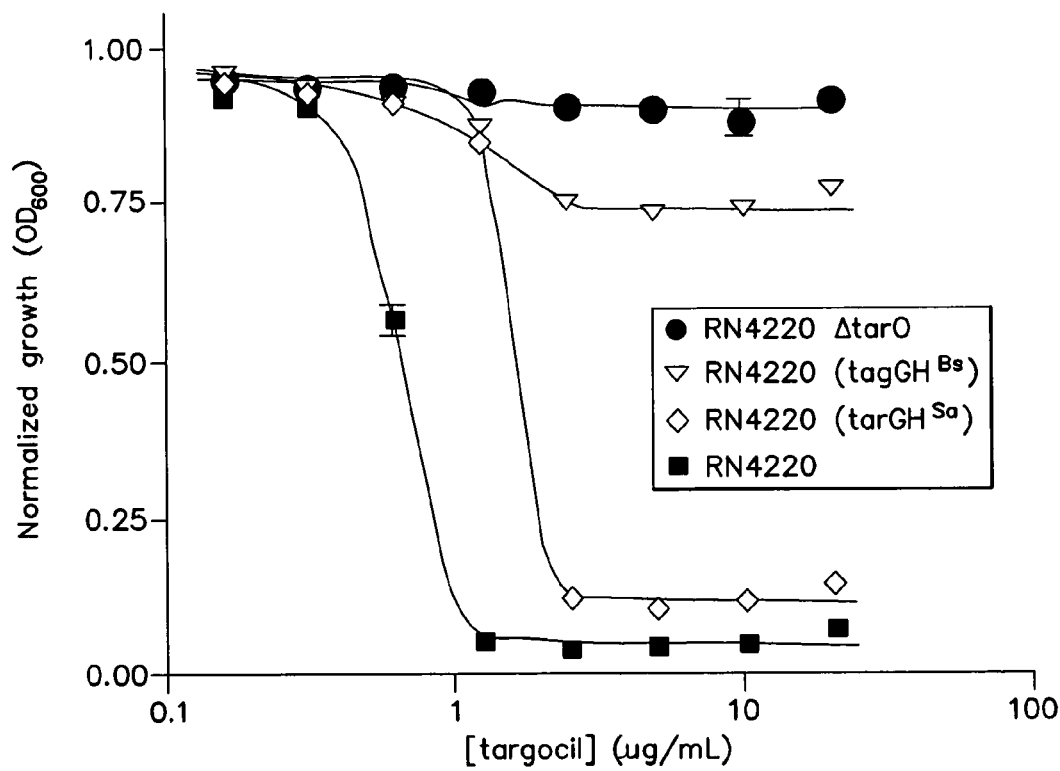

The *B. subtilis* 168 WTA transporter, TagGH, does not have stringent substrate specificity and is capable of transporting both polyglycerol-phosphate WTAs and other structurally distinct polymers (Karamata D, Pooley H M, & Monod M (1987) *Molecular & General Genetics* 207:73-81; Young M, Mauel C, Margot P, & Karamata D (1989) *Molecular Microbiology* 3:1805-1812.) We reasoned that if the observed targocil resistance in *B. subtilis* 168 is due to an intrinsically targocil-resistant ABC transporter (TagGH), then the functional expression of this transporter in *S. aureus* should confer targocil resistance. Consistent with this hypothesis, a *S. aureus* strain expressing *B. subtilis* 168 TagGH was found to be fully resistant to targocil. Furthermore, a strain overexpressing *S. aureus* TarGH was found to be partially resistant (FIG. 16d). Both results suggested that targocil's target is the two component transporter TarGH.

Figure 16E:
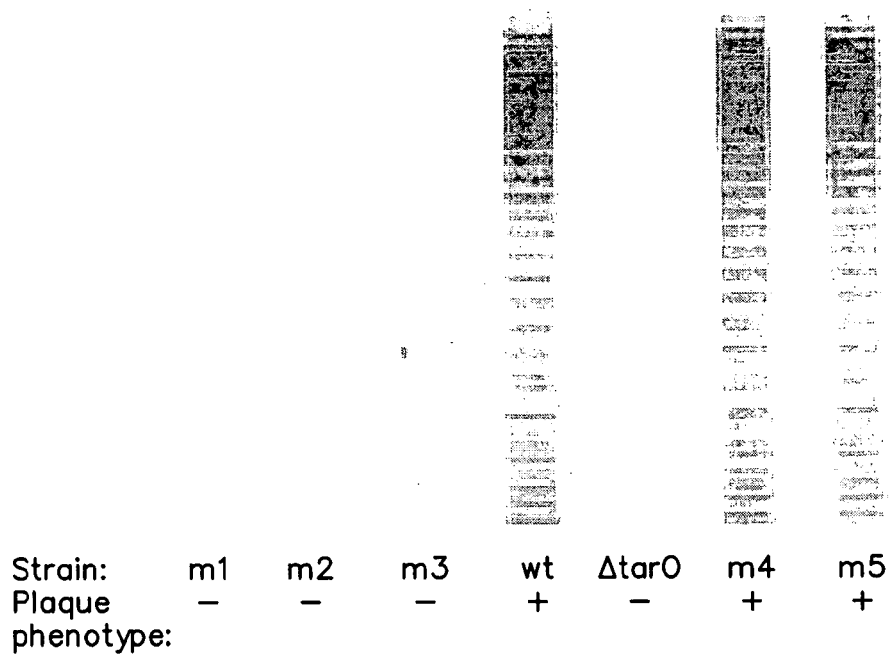
Figure 23A:
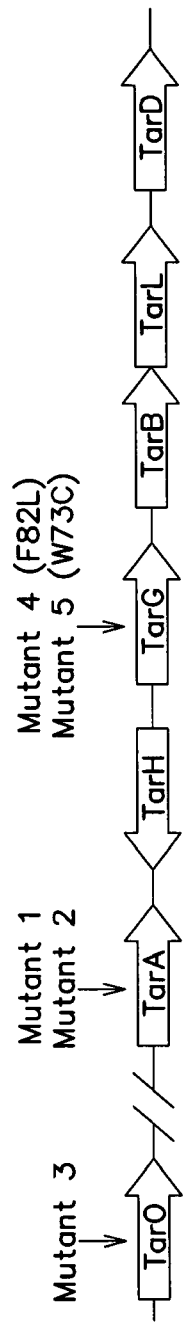
FIG. 23 shows (A) a summary of targeted sequencing results for targocil resistant mutants. (B) Predicted membrane topology of TarG showing the location of the point mutations that confer resistance to targocil. PredictProtein was used to generate the predicted membrane spanning regions of TarG (www.predictprotein.org/).
Figure 23B:
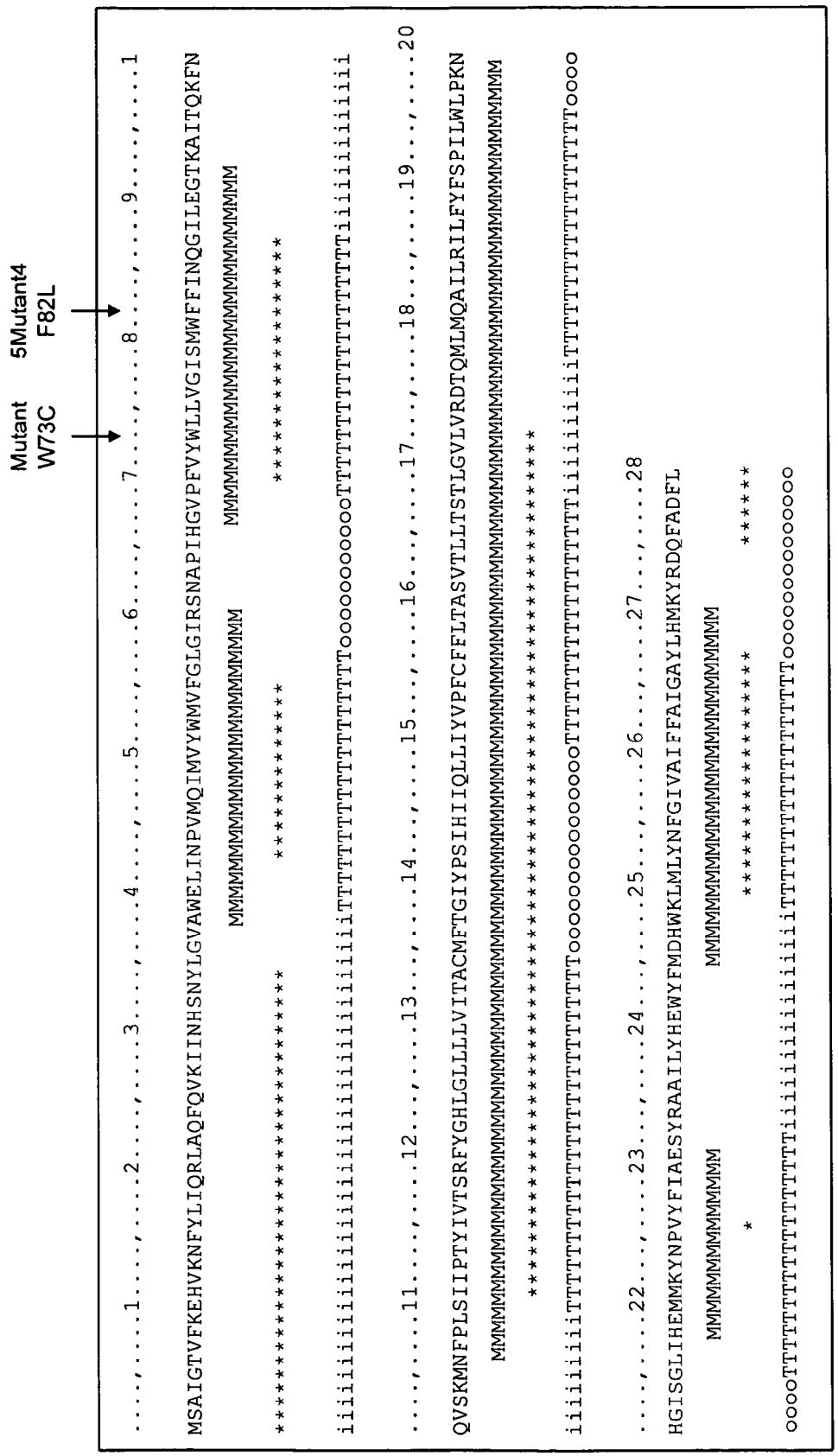

To determine whether targocil interacts with the transmembrane component (TarG) or the ATPase component (TarH) of the ABC transporter (Lazarevic V & Karamata D (1995) *Molecular Microbiology* 16:345-3), we selected for stable targocil resistant mutants. We envisioned that two classes of mutations would arise: (a) mutations in TarO or TarA that inactivate the WTA pathway and abolish WTA production, and (b) mutations within the target that allow WTA expression. To differentiate these two classes of mutants, we exploited the fact that *S. aureus* bacteriophage use WTAs as a receptor (FIGS. 19 and 22), and grouped the mutants into the two classes based on their susceptibility to phage infection. We selected three phage-resistant and two phage-sensitive mutants for further analysis. As expected, the phage-resistant mutants did not contain extractable WTAs (FIG. 16e) (Meredith T C, Swoboda J G, & Walker S (2008) *Journal Of Bacteriology* 190:3046-3056). Targeted sequencing of tar genes from these mutants showed that all three strains contained null mutations in tarO or tarA. The two phage-sensitive mutants, in contrast, contained extractable WTAs, and sequencing revealed that each contained a unique point mutation in tarG. The mutant tarG alleles each encode a different amino acid change on the same face of a predicted membrane spanning helix (FIG. 23).

Figure 24:
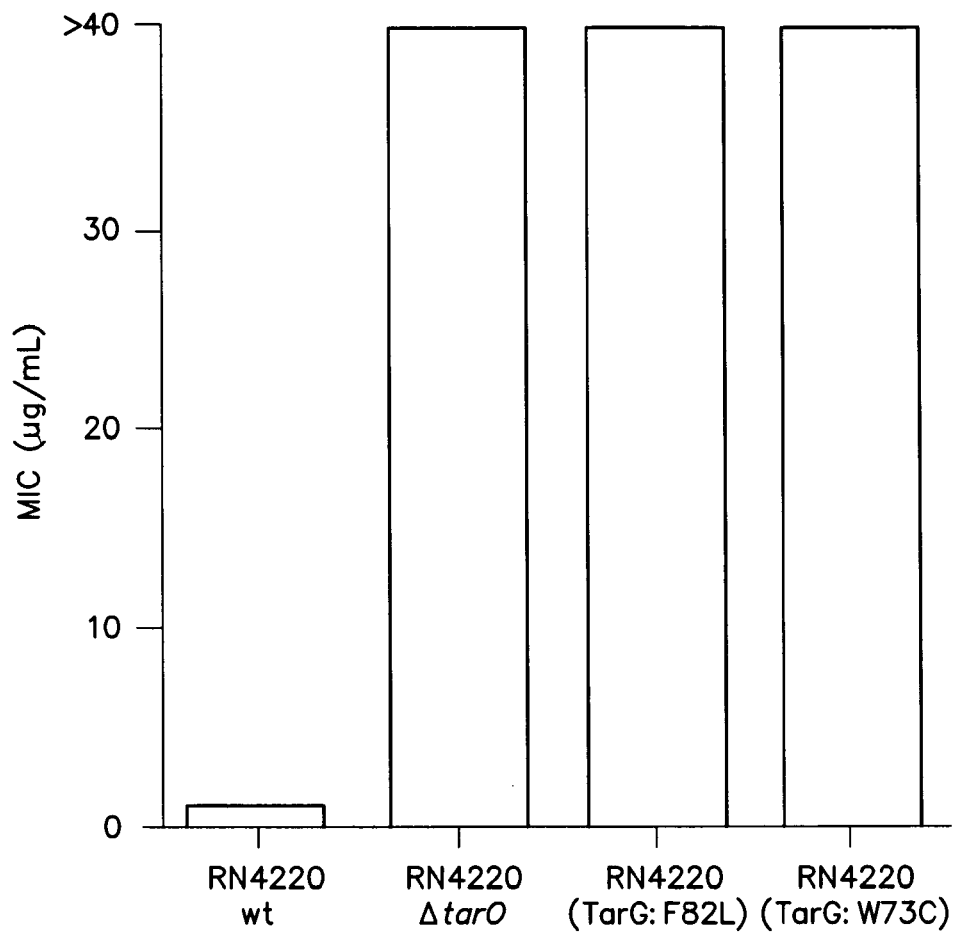
FIG. 24 shows a MIC analysis shows that mutant alleles encoding TarG:F82L (m4) and TarG:W73C (m5) confer resistance to targocil as compared to the wildtype and ΔtarO strain.

We verified that the observed mutations in TarG confer targocil resistance by exchanging the wildtype tarG gene in the targocil-sensitive RN4220 strain with each of the mutant tarG alleles, TarG:F82L and TarG:W73C (Bae T & Schneewind O (2006) *Plasmid* 55:58-63.) Both mutant strains were fully resistant to targocil, confirming that these point mutations are sufficient to bestow targocil resistance in an otherwise wildtype background (FIG. 24). Therefore, we conclude that TarG is a target of targocil. This compound is the first identified inhibitor of a class III ABC transporter involved in polymer export and its discovery suggests that it should be possible to identify selective inhibitors of other such polymer export systems, including lipoprotein and lipopolysaccharide transporters. (Davidson A L, Dassa E, Orelle C, & Chen J (2008) *Microbiology and Molecular Biology Reviews* 72:317-364) In addition to functioning as antibiotics, inhibitors such as targocil, and derivatives thereof, could be valuable tools for mechanistic and structural analyses of ABC transporters.

Virulence of Targocil Escape Mutants

Figure 16F:
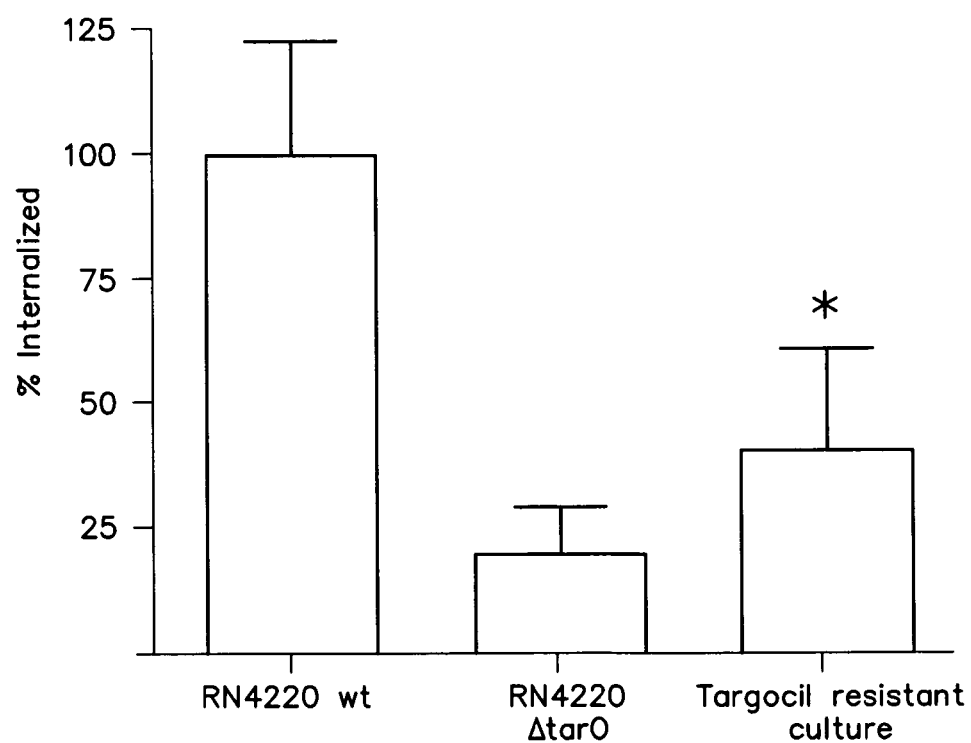

We have shown that mutations that prevent flux into the WTA pathway suppress the inhibitory effects of targocil. It has been reported that WTA-null mutants are impaired in their ability to adhere to epithelial and endothelial tissues and cannot colonize host tissue. (Weidenmaier C, Peschel A, Xiong Y Q, Kristian S A, Dietz K, Yeaman M R, & Bayer A S (2005) *Journal of Infectious Diseases* 191:1771-1777; Weidenmaier C, Kokai-Kun J F, Kristian S A, Chanturiya T, Kalbacher H, Gross M, Nicholson G, Neumeister B, Mond J J, & Peschel A (2004) *Nature Medicine* 10:243-245) *S. aureus* invades epithelial cells in order to evade the immune system during the course of infection, and invasion requires adhesion. We therefore utilized a human corneal epithelial cell (HCEC) invasion model to examine whether targocil escape mutants are defective at internalization. We found that a *S. aureus* ΔtarO mutant is greatly attenuated in its ability to invade HCECs compared to the wildtype control. (FIG. 16f) (Clement S, Vaudaux P, Francois P, Schrenzel J, Huggler E, Kampf S, Chaponnier C, Lew D, & Lacroix J S (2005) *Journal of Infectious Diseases* 192:1023-1028) We next treated wildtype *S. aureus* with targocil to select for resistant bacteria and repeated the internalization assay. The targocil-treated bacteria behaved similarly to the ΔtarO strain in the HCEC invasion assay, consistent with our earlier findings that targocil elicits WTA-null mutants. The WTA pathway has been speculated to be an antibiotic target for many years, but due to the complexity of the pathway, strategies for finding WTA inhibitors have been unsuccessful.

Here, we have reported the discovery of targocil, the first antibiotic to target WTA biosynthesis. We have demonstrated that two distinct classes of targocil escape mutants arise in vitro. Similar to most clinical antibiotics, mutations in the target (TarG) are able to confer resistance to targocil. (Andersson D I & Levin B R (1999) *Current Opinion in Microbiology* 2:489-493) The other class of mutants contains null mutations in the genes encoding TarO or TarA. Moreover, WTA-null mutants are more likely to occur than target mutations that confer resistance but retain activity; this is supported by the fact that a population of targocil escape mutants is unable to efficiently invade HCECs in vitro. Previous studies have shown that even though WTA-null mutants do not have growth rate defects in vitro, they are non-pathogenic due to defective colonization (and perhaps other growth defects) in vivo. If WTA-null mutants cannot easily adapt to survive in a host, then inhibiting conditionally essential genes within the WTA biosynthetic pathway is a viable strategy for battling the pervasive problem of MRSA. Although targocil itself is selective for *S. aureus*, there is no reason to think that to broader spectrum WTA-active antibiotics cannot be found (i.e., by targeting more highly conserved regions of the ABC transporter or other WTA enzymes). The work reported here demonstrates for the first time that WTA biosynthesis is a "druggable" antimicrobial target and that escape mutants are attenuated in their virulence.

Structure Activity Relationships Among Targocil Analogs

Based on the discovery of targocil as an inhibitor of WTA biosynthesis, further studies of the antibiotic were undertaken to elucidate the basis of its activity and to discover other antibiotics based on the structure of targocil. The goal for the initial SAR of targocil was to alter only the A ring to determine modifications that would improved potency as measured by MIC. We developed synthetic chemistry schemes to modify the targocil scaffold and, initially, nineteen different derivatives of targocil were made. (The first round of SAR structures and resulting MICs are reported in FIG. 15A) Based on these results, position $R_1$ of ring A contributes to biological activity. It is also seen that having the two methoxy groups at positions $R_1$ and $R_2$ make targocil more potent. In vitro data also suggest that the mutation frequency for this compound (4-22-7, FIG. 15A) is better as well. Based on these results, we made other derivatives using compound 4-22-7 as the lead structure. Modifications to the D ring appear particularly promising. Finally, the optimized compounds from this second round of SAR could then be used to discover modifications to the amine group that could be tolerated.

Synthesis of WTA Biosynthesis Inhibitors

The compounds of the invention can be prepared according to Scheme 1 below. Appropriately substituted anthranilic acids/esters (1) were readily converted into the corresponding 2-azidobenzoic acids/esters (2) by diazotization and displacement by sodium azide. Treatment of 2 with the substituted arylsulfonylactetonitriles in the presence of base led to the desired triazoloquinazolinone core (3) which was chlorinated using $POCl_3$ in the presence of equivalent amounts of tetrabutylammonium chloride. The imino chlorides (4) were then converted to the desired final products (5) by treatment with various amines.

Scheme 1

-continued

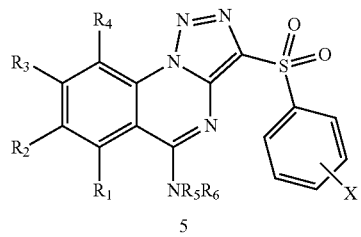

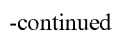

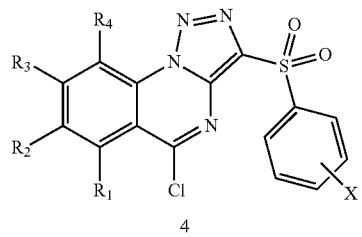

Wall Teichoic Acid Biosynthesis Inhibitors

In one aspect, the invention provides methods, compositions and kits for treating bacterial infection in a subject. In some embodiments the bacterial infection is treated by administering a Wall Teichoic Acid biosynthesis inhibitor. In some embodiments the Wall Teichoic Acid biosynthesis inhibitor is a TarB, TarF, TarG, TarH, or TarL inhibitor. An exemplary Wall Teichoic Acid biosynthesis inhibitor is a TarG inhibitor. In some embodiments the Wall Teichoic Acid biosynthesis inhibitor is compound 1835F03 (targocil). In some embodiments, compound 1835F03 (targocil) is administered to treat a Gram-positive bacterial infection.

Compounds of the present invention include Wall Teichoic Acid (WTA) biosynthesis inhibitors. According to one aspect of the invention, a compound is provided of the formula:

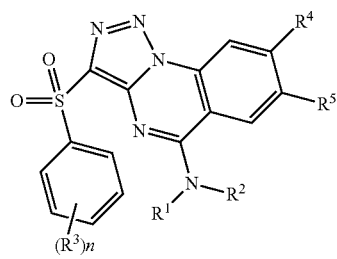

wherein:

$R^1$ and $R^2$ are independently selected from the group consisting of hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R^A$; $-CO_2R^A$; $-C(=O)N(R^A)_2$; or $-C(R^A)_3$; wherein each occurrence of $R^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

wherein $R^1$ and $R^2$ may be taken together with the intervening N atom to form a heterocyclic moiety;

each occurrence of $R^3$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR^C$; $-C(=O)R^C$; $-CO_2R^C$; $-C(=O)N(R^C)_2$; $-CN$; $-SCN$; $-SR^C$; $-SOR^C$; $-SO_2R^C$; $-NO_2$; $-N(R^C)_2$; $-NHC(O)R^C$; or $-C(R^C)_3$; wherein each occurrence of $R^C$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

n is an integer between 0 and 5, inclusive;

$R^4$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR^D$; $-C(=O)R^D$; $-CO_2R^D$; $-C(=O)N(R^D)_2$; $-CN$; $-SCN$; $-SR^D$; $-SOR^D$; $-SO_2R^D$; $-NO_2$; $-N(R^D)_2$; $-NHC(O)R^D$; or $-C(R^D)_3$; wherein each occurrence of $R^D$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

$R^5$ is selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-OR^E$; $-C(=O)R^E$; $-CO_2R^E$; $-C(=O)N(R^E)_2$; $-CN$; $-SCN$; $-SR^E$; $-SOR^E$; $-SO_2R^E$; $-NO_2$; $-N(R^E)_2$; $-NHC(O)R^E$; or $-C(R^E)_3$; wherein each occurrence of $R^E$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; wherein $R^4$ and $R^5$ may be taken together with the intervening atoms to form a cyclic moiety; and pharmaceutically acceptable salts thereof;

with the provisos that $R^4$ and $R^5$ can not both be hydrogen; $R^4$ can not be hydrogen if $R^5$ is chloro; and the compound is not of the formula:

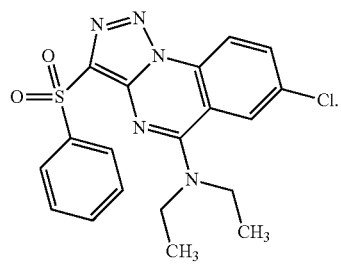

In certain embodiments, $R^1$ is hydrogen, $C_{1-6}$ aliphatic, or a nitrogen protecting group. In further embodiments, $R^1$ is hydrogen or $C_{1-6}$ alkyl. In certain embodiments, $R^1$ is $C_{1-6}$ alkyl. In certain embodiments, $R^1$ is methyl, ethyl, propyl, or butyl. In further embodiments, $R^1$ is ethyl. In certain embodiments, $R^2$ is hydrogen, $C_{1-6}$ aliphatic, or a nitrogen protecting group. In certain embodiments, $R^2$ is hydrogen or $C_{1-6}$ alkyl. In further embodiments, $R^2$ is $C_{1-6}$ alkyl. In certain embodiments, $R^2$ is methyl, ethyl, propyl, or butyl. In certain embodiments, $R^2$ is ethyl. In further embodiments, both $R^1$ and $R^2$ are independently $C_{1-6}$ alkyl. In certain embodiments, both $R^1$ and $R^2$ are independently methyl, ethyl, propyl, or butyl. In further embodiments, both $R^1$ and $R^2$ are ethyl. In certain embodiments, n is 0. In further embodiments, n is 1. In certain embodiments, the compound is of the formula:

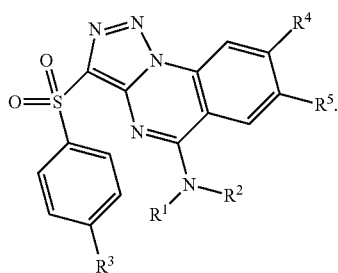

In certain embodiments, $R^3$ is selected from the group consisting of halogen and cyclic or acyclic, substituted or unsubstituted, branched or unbranched aliphatic. In further embodiments, n is 2. In certain embodiments, $R^3$ is cyclic or acyclic, substituted or unsubstituted, branched or unbranched aliphatic. In further embodiments, $R^3$ is $C_{1-6}$ alkyl. In certain embodiments, $R^3$ is methyl. In further embodiments, $R^3$ is halogen. In certain embodiments, $R^3$ is chlorine. In further embodiments, $R^3$ is —$OR^C$. In certain embodiments, $R^3$ is —$N(R^C)_2$. In further embodiments, $R^4$ is hydrogen. In certain embodiments, $R^4$ is cyclic or acyclic, substituted or unsubstituted, branched or unbranched aliphatic. In further embodiments, $R^4$ is $C_{1-6}$ alkyl. In certain embodiments, $R^4$ is methyl. In further embodiments, $R^4$ is halogen. In certain embodiments, $R^4$ is fluorine. In further embodiments, $R^4$ is chlorine. In certain embodiments, $R^4$ is bromine. In further embodiments, $R^4$ is —CN. In certain embodiments, $R^4$ is —$OR^D$. In further embodiments, $R^4$ is —$OCH_3$. In certain embodiments, $R^4$ is hydrogen or —$OCH_3$. In further embodiments, $R^4$ is —$N(R^C)_2$. In certain embodiments, $R^4$ is cyclic, substituted or unsubstituted aliphatic. In further embodiments, $R^4$ is cyclic, substituted or unsubstituted heteroaliphatic. In certain embodiments, $R^4$ is morpholino. In further embodiments, $R^4$ is substituted or unsubstituted aryl. In certain embodiments, $R^4$ is substituted or unsubstituted heteroaryl. In further embodiments, $R^5$ is hydrogen. In certain embodiments, $R^5$ is cyclic or acyclic, substituted or unsubstituted, branched or unbranched aliphatic. In further embodiments, $R^5$ is $C_{1-6}$ alkyl. In certain embodiments, $R^5$ is methyl. In further embodiments, $R^5$ is halogen. In certain embodiments, $R^5$ is fluorine. In further embodiments, $R^5$ is chlorine. In certain embodiments, $R^5$ is not chlorine. In further embodiments, $R^5$ is bromine. In certain embodiments, $R^5$ is —CN. In further embodiments, $R^5$ is —$OR^E$. In certain embodiments, $R^5$ is —$OCH_3$. In further embodiments, $R^5$ is —$N(R^D)_2$. In certain embodiments, $R^5$ is cyclic, substituted or unsubstituted aliphatic. In further embodiments, $R^5$ is cyclic, substituted or unsubstituted heteroaliphatic. In certain embodiments, $R^5$ is morpholino. In further embodiments, $R^5$ is substituted or unsubsituted aryl. In certain embodiments, $R^5$ is substituted or unsubstituted heteroaryl. In further embodiments, at least one of $R^4$ and $R^5$ is hydrogen. In certain embodiments, at least one of $R^4$ and $R^5$ is not hydrogen. In further embodiments, at least one of $R^4$ and $R^5$ is halogen or —$OCH_3$. In certain embodiments, at least one of $R^4$ and $R^5$ is halogen. In further embodiments, when $R^4$ is hydrogen, $R^5$ is not hydrogen or chlorine. In certain embodiments, at least one of $R^4$ and $R^5$ is —$OCH_3$. In further embodiments, both $R^4$ and $R^5$ are —$OCH_3$. In certain embodiments, $R^4$ and $R^5$ are taken together with the intervening atoms to form a cyclic moiety. In further embodiments, $R^4$ and $R^5$ are taken together with the intervening atoms to form a five-membered cyclic moiety. In certain embodiments, $R^4$ and $R^5$ are taken together with the intervening atoms to form a six-membered cyclic moiety. In further embodiments, $R^4$ and $R^5$ are taken together with the intervening atoms to form a heterocyclic moiety. In certain embodiments, the cyclic moiety is aromatic. In further embodiments, the cyclic moiety is not aromatic. In certain embodiments, the cyclic moiety is morpholino. In further embodiments, both $R^1$ and $R^2$ are $C_{1-6}$ alkyl; n is 0 or 1; $R^3$ is selected from the group consisting of halogen and $C_{1-6}$ alkyl; $R^4$ and $R^5$ are independently selected from the list consisting of hydrogen, halogen, —CN, —$OR^D$, and heterocyclic; or $R^4$ and $R^5$ may be taken together with the intervening atoms to form a heterocyclic moiety. In certain embodiments, both $R^1$ and $R^2$ are ethyl; n is 0 or 1; $R^3$ is selected from the group consisting of chloro and methyl; $R^4$ and $R^5$ are independently selected from the group consisting of hydrogen, fluoro, chloro, bromo, —CN, methoxy, and morpholino; or $R^4$ and $R^5$ may be taken together with the intervening atoms to form a 1,4-dioxanyl moiety. In further embodiments, the compound is selected from the group consisting of:

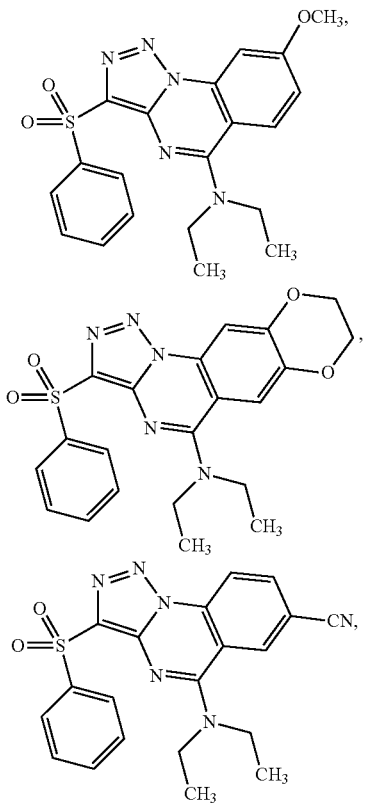

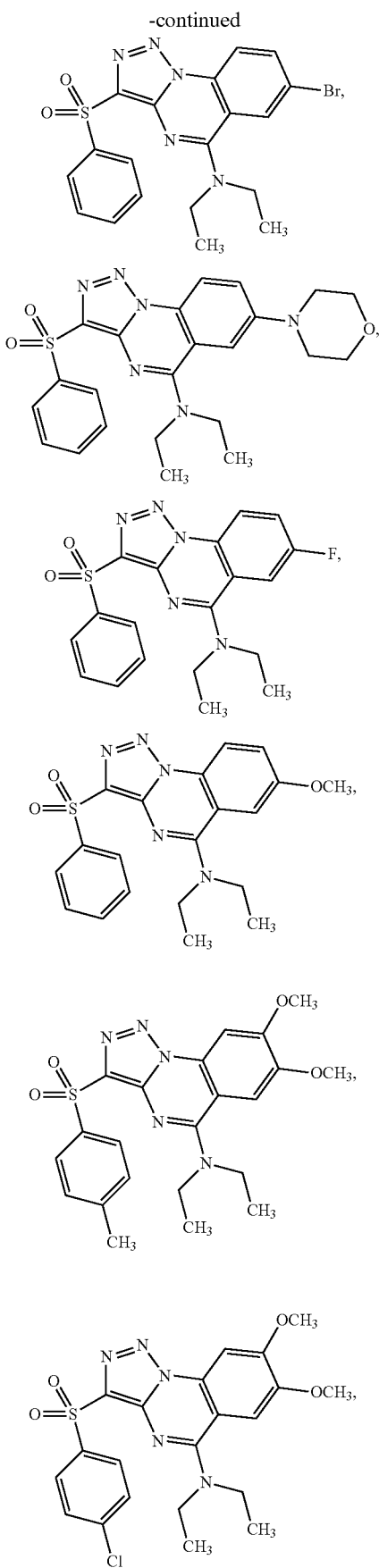

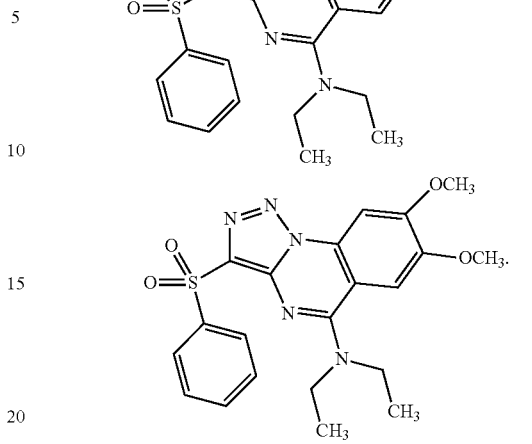

Another aspect of the invention includes a pharmaceutical composition comprising a therapeutically effective amount of compound 1835F03 (targocil) or an above-mentioned Wall Teichoic Acid (WTA) biosynthesis inhibitor; and a pharmaceutically acceptable excipient. Certain embodiments comprise a Wall Teichoic Acid (WTA) biosynthesis inhibitor and a pharmaceutically acceptable excipient. In further embodiments, the WTA biosynthesis inhibitor is a TarB, TarF, TarG, TarH, or TarL inhibitor. In certain embodiments, the WTA biosynthesis inhibitor is compound 1835F03 (targocil). In further embodiments, the WTA biosynthesis inhibitor is a TarG inhibitor.

Further aspects of the invention include a method of treating bacterial infection in a subject comprising administering to a subject in need of such a treatment a therapeutically effective amount of compound 1835F03 (targocil) or an above-mentioned Wall Teichoic Acid (WTA) biosynthesis inhibitor. In certain embodiments, the subject is human. In further embodiments, the subject is a mouse. In certain embodiments, the compound or composition is administered in combination with an additional drug for treating bacterial infection. In further embodiments, the bacterial infection occurs, at least partially, in the eye of the subject. In certain embodiments, the bacterial infection occurs, at least partially, in a lung of the subject. In further embodiments, the bacterial infection occurs, at least partially, in the skin of the subject. In certain embodiments, the bacterial infection occurs, at least partially, in the nostrils of the subject. In further embodiments, the bacterial infection occurs, at least partially, in the respiratory tract of to the subject. In certain embodiments, the bacterial infection occurs, at least partially, in the blood of the subject. In further embodiments, the bacterial infection occurs, at least partially, in the vital organ system of the subject. In certain embodiments, the bacterial infection occurs, at least partially, in the urinary tract of the subject. In further embodiments, the bacterial infection comprises Gram-positive bacteria. In certain embodiments, the Gram-positive bacteria is a species of *Staphylococcus*. In further embodiments, the *Staphylococcus* is *S. aureus*. In certain embodiments, the *S. aureus* is Methicillin-resistant (MRSA). In further embodiments, the Gram-positive bacteria is a species of *Bacillus*. In certain embodiments, the *Bacillus* is *B. subtilis*. In further embodiments, the Gram-positive bacteria is a species of *Streptococcus*. In certain embodiments, the

*Streptococcus* is *S. pneumoniae*. In further embodiments, the Gram-positive bacteria is a species of *Listeria*. In certain embodiments, the Gram-positive bacteria is a species of *Enterococcus*. In further embodiments, the Gram-positive bacteria is a species of *Clostridium*. In certain embodiments, the Gram-positive bacteria is a species of *Corynebacterium*. In further embodiments, the Gram-positive bacteria produce Wall Teichoic Acids.

According to one aspect of the invention, methods for treating a Gram-positive bacterial infection in a subject are provided. The methods include administering to the subject an effective amount of a Wall Teichoic Acid (WTA) biosynthesis inhibitor to treat the Gram-positive bacterial infection. In some embodiments, the Gram-positive bacterial infection is caused by *Staphylococcus aureus*. In some embodiments, the WTA biosynthesis inhibitor is a TarB, TarF, TarG, TarH, or TarL inhibitor. In certain embodiments, the WTA biosynthesis inhibitor is a TarG inhibitor. In some embodiments, the WTA biosynthesis inhibitor is compound 1835F03 (targocil). In some embodiments, the WTA biosynthesis inhibitor is a compound as described herein. In some embodiments, the subject is human.

Gram-positive bacteria to which the methods and compositions of the present invention can be applied encompass without limitation those of the generi *Micrococcus, Staphylococcus, Streptococcus, Peptococcus, Peptostreptococcus, Enterococcus, Methanobacterium, Bacillus, Clostridium, Lactobacillus, Listeria, Erysipelothrix, Corynebacterium, Propionibacterium, Eubacterium, Actinomyces, Arachnia, Bifidobacterium, Bacterionema, Rothia, Mycobacterium, Nocardia, Streptomyces*, and *Micropolyspora* (Classification according to Joklik et al., Zinsser Microbiology, 16th Edition, Appleton, N.Y., 1976). Pathological conditions in humans caused by Gram-positive bacteria include, for example, pneumococcal pneumonia, local and systemic staphylococcal infections, toxic shock syndrome, osteomyelitis, scarlet fever, pyoderma, and cellulitis (Petersdorf et al., Harrison's Principles of Internal Medicine, 10th Edition, McGraw-Hill, 1984).

According to another aspect of the invention, methods for suppressing Gram-positive bacterial cell growth are provided. The methods include contacting at least one Gram-positive bacterial cell with an effective amount of a Wall Teichoic Acid (WTA) biosynthesis inhibitor to suppress Gram-positive bacterial cell growth. In some embodiments, the at least one Gram-positive bacterial cell is a *Staphylococcus aureus* bacterial cell. In certain embodiments, the WTA biosynthesis inhibitor is a TarB, TarF, TarG, TarH, or TarL inhibitor. In some embodiments, the WTA biosynthesis inhibitor is a TarG inhibitor. In some embodiments, the WTA biosynthesis inhibitor is compound 1835F03 (targocil). In some embodiments, the WTA biosynthesis inhibitor is a compound as described herein. In some embodiments, the at least one Gram-positive bacterial cell is in a subject. In certain embodiments, the subject is human.

According to yet another aspect of the invention, pharmaceutical compositions that include a Wall Teichoic Acid (WTA) biosynthesis inhibitor and a pharmaceutically acceptable excipient are provided. In some embodiments, the WTA biosynthesis inhibitor is a TarB, TarF, TarG, TarH, or TarL inhibitor. In some embodiments, the WTA biosynthesis inhibitor is a TarG inhibitor. In certain embodiments, the WTA biosynthesis inhibitor is compound 1835F03 (targocil).

According to another aspect of the invention, kits for treating a Gram-positive bacterial infection in a subject are provided. The kits include a first container comprising a Wall Teichoic Acid (WTA) biosynthesis inhibitor or a pharmaceutical composition thereof and instructions for administration of the WTA biosynthesis inhibitor.

According to yet another aspect of the invention, methods for identifying an antibacterial therapeutic agent are provided. The methods include contacting a Gram-positive bacterial cell with a candidate agent, and determining whether the candidate agent inhibits TarG function, wherein if the candidate agent inhibits TarG function, the candidate agent is identified as an antibacterial therapeutic agent. In some embodiments, the Gram-positive bacterial cell is *Staphylococcus aureus*.

According to another aspect of the invention, methods for identifying an antibacterial therapeutic agent are provided. The methods include (a) contacting a first Gram-positive bacterial cell with a candidate agent, wherein the first bacterial cell contains a functional tarO gene; (b) determining if the candidate agent suppresses growth of the first Gram-positive bacterial cell; (c) contacting a second Gram-positive bacterial cell with the candidate agent, wherein the second Gram-positive bacterial cell does not contain a functional tarO gene; and (d) determining if the candidate agent suppresses growth of the second Gram-positive bacterial cell; wherein if the candidate agent suppresses growth of the first Gram-positive bacterial cell, but not the second Gram-positive bacterial cell, the candidate agent is identified as an antibacterial therapeutic agent. In some embodiments, the first and second bacterial cells are *Staphylococcus aureus* bacterial cells.

According to another aspect of the invention, methods for identifying a tarG inhibitor agent are provided. The methods include (a) contacting a first Gram-positive bacterial cell with a candidate agent, wherein the first Gram-positive bacterial cell contains a functional tarO gene; (b) determining if the candidate agent suppresses growth of the first Gram-positive bacterial cell; (c) contacting a second Gram-positive bacterial cell with the candidate agent, wherein the second Gram-positive bacterial cell does not contain a functional tarO gene; (d) determining if the candidate agent suppresses growth of the second bacterial cell, and (e) validating that tarG is the target of the compound; wherein if the candidate agent suppresses growth of the first bacterial cell, but does not suppress the growth of the second bacterial cell, and tarG is validated as the target, the candidate agent is identified as a tarG inhibitor. In some embodiments, steps of validating include (e) contacting a third Gram-positive bacterial cell with the candidate agent wherein the third bacterial cell contains a resistant Wall Teichoic Acid gene, and (f) determining if the third bacterial cell produces WTA and/or if growth of the third bacterial cell is suppressed; wherein if the candidate agent suppresses growth of the first bacterial cell, but not the second bacterial cell, and the third bacterial cell produces WTA and/or the growth of the third bacterial cell is not suppressed, the candidate agent is identified as a tarG inhibitor. In certain embodiments, the resistant Wall Teichoic Acid gene is a mutant TarB, TarF, TarG, TarH, or TarL gene. In some embodiments, the resistant Wall Teichoic Acid gene is a mutant TarG gene. In some embodiments, the first bacterial cell, the second bacterial, and the third bacterial cell are *Staphylococcus aureus* bacterial cells. In certain embodiments, the resistant Wall Teichoic Acid gene is a *B. subtilis* tagG or tagH gene. In some embodiments, the first bacterial cell and the second bacterial cell are *Staphylococcus aureus* bacterial cells.

In one aspect, the invention provides methods for treating a bacterial infection in a subject by administering an antibacterial therapeutic agent of the invention to the subject. In some embodiments the antibacterial therapeutic agents of the invention are WTA biosynthesis inhibitors. As used herein, the term "WTA biosynthesis inhibitor" means a compound that reduces or eliminates production of WTA in a cell when the cell is contacted with the compound. A "WTA biosynthesis inhibitor" or "WTA pathway inhibitor" is any agent that inhibits one or more enzymes of the WTA pathway. Non-limiting examples of WTA biosynthesis inhibitors are inhibitors for TarA, TarB, TarD, TarE, TarG, TarH, TarI, TarI', TarJ', TarK, TarL, and/or TarX. A "WTA biosynthesis inhibitor" or "WTA pathway inhibitor" may be bacteriocidal or bacteriostatic.

In some embodiments of the invention, a bacterial infection is treated by administering an antibacterial therapeutic agent of the invention that inhibits bacterial cell wall synthesis. In some embodiments, the bacterial infection is treated by administering an antibacterial therapeutic agent that inhibits bacterial cell wall synthesis. A bacterial infection may be treated by administering an antibacterial therapeutic agent of the invention that inhibits one or more enzymes involved with the biosynthesis of the bacterial cell wall. A bacterial infection may be treated by administering a WTA biosynthesis inhibitor. In some embodiments the bacterial infection is treated by administering a TarB, TarF, TarG, TarH or TarL inhibitor. In some embodiments, a bacterial infection may be treated by administering a TarG inhibitor. Compound 1835F03 (targocil) is an exemplary TarG inhibitor that may be administered to treat a Gram-positive bacterial infection.

By bacterial infection is meant the invasion of a subject by pathogenic bacteria. For example, the infection may include the excessive growth of bacteria that are normally present in or on the body of the subject or growth of bacteria that are not normally present in or on the animal. More generally, a bacterial infection is any situation in which the presence of a bacterial population(s) is damaging to a host subject. Thus, a subject is "suffering" from a bacterial infection when an excessive amount of a bacterial population is present in or on the animal's body, or when the presence of a bacterial population(s) is damaging, may damage, or may produce an unwanted effect in cells or tissues of the subject.

In some embodiments of the invention, methods and compounds of the invention are used to suppress bacterial cell growth or treat bacterial infections. In some embodiments, the bacteria are Gram-positive bacteria or the infections are infections with Gram-positive bacteria. Non-limiting examples of Gram-positive bacteria are *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium*, and *Corynebacterium*. In some embodiments the Gram-positive bacteria is *Staphylococcus aureus* (*S. aureus*). Non-limiting examples of pathogenic Gram-positive bacterial strains that make WTAs include *Staphylococcus aureus, Streptococcus pneumoniae, Listeria monocytogenes, Enterococcus faecalis*, and *Enterococcus faecium*. Strains that make WTAs may be treated with a WTA synthesis inhibitor of the invention.

*Staphylococcus aureus* is the most frequent cause of skin, wound, and blood infections and the second most frequent cause of lower respiratory tract infections, and the microorganism tends to prey on immunocompromised and institutionalized patients. *S. aureus* is a significant clinical target because it is refractive to most systemic antibiotic treatments. One of the key contributors to the increase in mortality and morbidity due to bacterial infections is the increasing prevalence of drug-resistant bacteria. Examples of the seriousness of antibiotic resistance are Methicillin-resistant staphylococci (MRSA), and the emergence of vancomycin-resistant *S. aureus* which have become resistant to virtually all currently used antibiotics. Thus, Methicillin-resistant *S. aureus* may also be used as an antibiotic-resistant model organism for identifying antibacterial therapeutic compounds.

In some embodiments, the invention provides methods for suppressing bacterial cell growth. Methods of the invention may include contacting a bacterial cell with an effective amount of a WTA biosynthesis inhibitor to suppress bacterial cell growth. In some embodiments the bacterial cell is in a subject. As used herein, the term "in a subject" means inside a subject and/or on the surface of a subject. Examples of surfaces of a subject, include but are not limited to on the subject's skin, eye, or other body membrane or external surface. In some embodiments the subject is human. By "suppressing bacterial cell growth" is meant a decrease in the rate of proliferation of the bacterial cell. In some embodiments the suppression of bacterial cell growth results in inhibition of bacterial cell growth. In some embodiments the suppression of bacterial cell growth results in the death of the bacteria or death in a population of bacteria.

Suppression of bacterial cell growth or a decrease in the rate of proliferation of the bacterial cell or population of bacterial cells can be determined by assessing the cell or population of cells that has been contacted with the WTA biosynthesis inhibitor, to a cell or population of cells that has not been contacted with a WTA biosynthesis inhibitor and comparing differences in viability and/or proliferation. In some embodiments contacting of the cell or population of cells with the WTA biosynthesis inhibitor results in at least 1%, at least a 10%, at least a 20%, at least a 30%, at least a 40%, at least a 50%, at least a 60%, at least a 70%, at least a 80%, at least a 90%, or up to a 100% suppression of growth. A 100% suppression of growth equals the death of the bacterial cell or population of bacterial cells.

In some embodiments a control level of WTA biosynthesis and/or bacterial cell growth is the level that represents the normal level of WTA biosynthesis or bacterial cell growth. The control level may be in an infected subject, cell, tissue, or cell preparation such as a cell or cell population in culture. In some embodiments a control level of WTA biosynthesis or bacterial cell growth will be the level in a cell, tissue, or subject with a bacterial infection. These and other types of control levels are useful in assays to assess the efficacy of a WTA biosynthesis inhibitor.

It will be understood by one of ordinary skill in the art that a control level of WTA biosynthesis or bacterial cell growth may be a predetermined value, which can take a variety of forms. It can be a single value, such as a median or mean. It can be established based upon comparative groups, such as bacterial cells that have not been contacted with a WTA biosynthesis inhibitor. Other comparative groups may be groups of subjects with a bacterial infection. It will be understood that disease-free cells and/or subject tissues may be used as comparative groups for cells or tissues that have a bacterial infection.

In some embodiments, a compound that inhibits and thereby reduces the level of WTA biosynthesis or bacterial cell growth is a compound that reduces the likelihood or risk of having a bacterial infection. A level of WTA biosynthesis or bacterial cell growth in a cell, tissue, and/or subject may be one that is below the WTA biosynthesis or bacterial cell growth level in cells, tissues, and/or subjects with a bacterial infection, e.g., a level that is clinically asymptomatic, but may still be treated and further reduced by to administration of a WTA biosynthesis inhibitor. The invention relates in part to the administration of a WTA biosynthesis inhibitor to a cell, tissue, and/or subject in an amount effective to reduce WTA biosynthesis or bacterial cell growth in cells, tissues, and/or subjects with a bacterial infection.

In some embodiments, the invention provides methods of treatment by administering a WTA biosynthesis inhibitor. As used herein, the term "treat" includes active treatment of a subject that has a bacterial infection (e.g., a subject diagnosed with such a condition) and also includes prophylactic treatment of a subject who has not yet been diagnosed. Subjects that have not yet been diagnosed include subjects that are at high risk for bacterial infection. Non-limiting examples of subjects at high risk for infection, include subjects undergoing surgery, subjects that are immunocompromised, such as AIDS patients, and subjects being treated with immunosuppressants. WTA biosynthesis inhibitors may be administered prophylactically to a subject at risk of bacterial infection. Determination of a subject at risk for bacterial infection, and/or the determination of a diagnosis of bacterial infection in a subject, may be done by one of ordinary skill in the art using routine methods.

In some embodiments, the invention provides methods for treating a bacterial infection in a subject by administering an effective amount of a WTA biosynthesis inhibitor to treat the bacterial infection. The invention, in part, provides methods for suppressing bacterial cell growth by contacting a cell with an effective amount of a WTA biosynthesis inhibitor to suppress cell growth.

The invention involves, in part, the administration of an effective amount of a WTA biosynthesis inhibitor. Typically effective amounts of a WTA biosynthesis inhibitor will be determined in clinical trials, establishing an effective dose for a test population versus a control population in a blind study. In some embodiments an effective amount will be that amount that diminishes or eliminates a bacterial infection and its effects in a cell, tissue, and/or subject. Thus, an effective amount may be the amount that when administered reduces the amount of cell and or tissue damage and/or cell death from the amount that would occur in the subject or tissue without the administration of a WTA biosynthesis inhibitor.

The pharmaceutical composition dosage may be adjusted by the individual physician or veterinarian, particularly in the event of any complication. A therapeutically effective amount typically varies from 0.001 mg/kg to about 1000 mg/kg, 0.01 mg/kg to about 1000 mg/kg, 0.01 mg/kg to about 100 mg/kg, 0.01 mg/kg to about 10 mg/kg, 0.01 mg/kg to about 1 mg/kg, 0.1 mg/kg to about 100 mg/kg, 0.1 mg/kg to about 10 mg/kg, 0.1 mg/kg to about 1 mg/kg, 0.5 mg/kg to about 1000 mg/kg, 0.5 mg/kg to about 100 mg/kg, 0.5 mg/kg to about 10 mg/kg, 0.5 mg/kg to about 1 mg/kg, 1 mg/kg to about 100 mg/kg, 1 mg/kg to about 10 mg/kg, 10 mg/kg to about 200 mg/kg, 10 mg/kg to about 20 mg/kg, preferably from about 0.1 mg/kg to about 200 mg/kg, and most preferably from about 0.2 mg/kg to about 20 mg/kg, in one or more dose administrations daily, for one or more days. It will be recognized by those of skill in the art that some of the WTA biosynthesis inhibitors may have detrimental effects at high amounts. Thus, an effective amount for use in the methods of the invention may be optimized such that the amount administered results in minimal negative side effects and maximum treatment of bacterial infection.

The absolute amount of an inhibitor compound of the invention to be administered will depend upon a variety of factors, including the material selected for administration, whether the administration is in single or multiple doses, and individual subject parameters including age, physical condition, size, weight, and the stage of the bacterial infection. These factors are well known to those of ordinary skill in the art and can be addressed with no more than routine experimentation.

When administered, the WTA biosynthesis inhibitors (also referred to herein as therapeutic compounds and/or pharmaceutical compounds) are administered in pharmaceutically acceptable compositions. Such compositions may routinely contain one or more pharmaceutically acceptable excipients such as e.g., salt, buffering agents, preservatives, compatible excipients, and optionally other therapeutic agents.

The pharmaceutical compositions of the invention contain an effective amount of one or more WTA biosynthesis inhibitors and optionally additional therapeutic agents included in a pharmaceutically-acceptable excipient. The term pharmaceutically-acceptable excipient means one or more compatible solid or liquid filler, diluents or encapsulating substances which are suitable for administration to a human or other vertebrate animal. The term excipient denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

For oral administration, the WTA biosynthesis inhibitors can be formulated readily by combining the active compound(s) with pharmaceutically acceptable excipients well known in the art. Such excipients enable the compounds of the invention to be formulated as tablets, pills, dragees, capsules, liquids, sprays, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any excipients.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, Soluble Polymer-Enzyme Adducts In: Enzymes as Drugs, Hocenberg and Roberts, eds., Wiley-Interscience, New York, N.Y., pp. 367-383; Newmark, et al., 1982, *J. Appl. Biochem.* 4:185-189. Other polymers that could be used are poly-1,3-dioxolane and poly-1,3,6-tioxocane.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the WTA biosynthesis inhibitor or by release of the biologically active material beyond the stomach environment, such as in the intestine.

In some embodiments, a coating impermeable to at least pH 5.0 may be used to ensure full gastric resistance. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic e.g., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the WTA biosynthesis inhibitors may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the LNR-FID domain or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The therapeutics of the invention can be administered by any conventional route, including injection or by gradual infusion over time. The administration may for example, be oral, intravenous, intraperitoneal, intrathecal, intramuscular, intranasal, intracavity, subcutaneous, intradermal, mucosal, transdermal, or transdermal.

The therapeutic compositions may conveniently be presented in unit dosage form and may be prepared by any of the methods well known in the art of pharmacy. Methods of preparation may include the step of bringing the compounds into association with a excipient which constitutes one or more accessory ingredients. In general, the compositions are prepared by uniformly and intimately bringing the therapeutic agent into association with a liquid excipient, a finely divided solid excipient, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Excipient formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion.

In some embodiments of the invention, a WTA biosynthesis inhibitor may be delivered in the form of a delivery complex. The delivery complex may deliver the WTA biosynthesis inhibitor into any cell type, or may be associated with a molecule for targeting a specific cell type. Examples of delivery complexes include a WTA biosynthesis inhibitor associated with: a sterol (e.g., cholesterol), a lipid (e.g., a cationic lipid, virosome or liposome), or a target cell specific binding agent (e.g., an antibody, including but not limited to monoclonal antibodies, or a ligand recognized by target cell specific receptor). Some complexes may be sufficiently stable in vivo to prevent significant uncoupling prior to internalization by the target cell. However, the complex can be cleavable under appropriate conditions within the cell so that the WTA biosynthesis inhibitor is released in a functional form.

An example of a targeting method, although not intended to be limiting, is the use of liposomes to deliver a WTA biosynthesis inhibitor into a cell. Liposomes may be targeted to a particular tissue, such particular cell types that are infected, by coupling the liposome to a specific ligand such as a monoclonal antibody, sugar, glycolipid, or protein that targets the cell type of the infected cells. Such proteins include proteins or fragments thereof specific for a particular cell type, antibodies for proteins that undergo internalization in cycling, proteins that target intracellular localization and enhance intracellular half life, and the like.

For certain uses, it may be desirable to target the compound to particular tissues or cells, for example tissues or cells infected by Gram-positive bacteria. In such instances, a vehicle (e.g., a liposome) used for delivering a WTA biosynthesis inhibitor to a cell type (e.g., an infected cell) may have a targeting molecule attached thereto that is an antibody specific for a surface membrane polypeptide of the cell type or may have attached thereto a ligand for a receptor on the cell type. Such a targeting molecule can be bound to or incorporated within the WTA biosynthesis inhibitor delivery vehicle.

Where liposomes are employed to deliver a WTA biosynthesis inhibitor, proteins that bind to a surface membrane protein associated with endocytosis may be incorporated into the liposome formulation for targeting and/or to facilitate uptake.

Liposomes are commercially available from Invitrogen, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include, but are not limited to, polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one particular embodiment, the preferred vehicle is a biocompatible microparticle or implant that is suitable for implantation into the mammalian recipient. Exemplary bioerodible implants that are useful in accordance with this method are described in PCT International application no. WO 95/24929, entitled "Polymeric Gene Delivery System". describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in WO 95/24929. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used. The polymeric matrix composition can be selected to have both favorable degradation rates and also to be formed of a material which is bioadhesive, to further increase the effectiveness of transfer when the device is administered to a vascular surface. The matrix composition also can be selected not to degrade, but rather, to release by diffusion over an extended period of time.

Both non-biodegradable and biodegradable polymeric matrices can be used to deliver agents and compounds of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents and/or compounds of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Use of a long-term sustained release implant may be particularly suitable for treatment of subjects with a systemic bacterial infections or ongoing medical issues that benefit from long-term antibacterial treatment. A non-limiting example may be a subject at risk of developing a Gram-positive bacterial infection who would benefit from long-term prophylactic treatment with a antibacterial compound of the invention.

"Long-term" release, as used herein, means that the implant is constructed and arranged to deliver therapeutic levels of the active ingredient for at least 7 days, and preferably 30-60 days, and most preferably months or years. The implant may be positioned at or near the site of the infection if it is localized in a tissue or region of the subject. It will be understood by those of ordinary skill in the art that long-term release implants may be used in or near tissues and organs to allow regional administration of a WTA biosynthesis inhibitor. Long-term sustained release implants are well known to those of ordinary skill in the art and include some of the release systems described above.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous excipients include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, additional antimicrobials, anti-oxidants, chelating agents, and inert gases and the like.

The WTA biosynthesis inhibitors may be administered alone, and/or in combination with other drug therapies. In some embodiments the WTA biosynthesis inhibitors are administered in conjunction with a second therapeutical compound. In some embodiments the second therapeutical compound is a antibiotic therapeutic compound. Non-limiting examples of antibiotic therapeutic compounds are amoxillin, erythromycin, azithromycin, clarithromycin, gentamicin, tobramycin, ciprofloxaxin, norfloxacin, gatifloxacin, ofloxacin, levofloxacin, moxifloxacin, metronidazole, lomefloxacin, ciprofloxacin, natamycin, neomycin, polymyxin B, gentamycin, bacitracin, trovafloxacin, grepafloxacin, sulfacetamide, tetracycline, gramicidin, chloramphenicol, or gramicidin.

In some embodiments the WTA biosynthesis inhibitors are administered in conjunction with antibodies directed to bacterial infections. Antibodies protect against bacterial attack by recognizing and binding to antigens on the bacteria to thereby facilitate the removal or "clearance" of the bacteria by a process called phagocytosis, wherein phagocytic cells (predominantly neutrophils and macrophages) identify, engulf, and subsequently destroy the invading bacteria. Even though bacteria have developed mechanisms to avoid phagocytosis, such as the production of a "capsule" to which phagocytes cannot adhere or the production of toxins that actually poison the encroaching phagocytes, antibodies can overcome these defenses by, for example, binding to the toxins to thereby neutralize them. More significantly, antibodies may themselves bind to the capsule to coat it, in a process called opsonization, to make the bacteria extremely attractive to phagocytes and to enhance their rate of clearance from the bloodstream.

In some embodiments the invention provides methods for treating a bacterial infection in a subject by administering an effective amount of compound disclosed herein, including 1835F03 (targocil).

In some embodiments the invention provides methods for suppressing bacterial growth by contacting a bacterial cell with an effective amount of compound disclosed herein, including compound1835F03 (targocil).

In one aspect, the invention provides a pharmaceutical kit comprising one or more containers comprising one or more WTA biosynthesis inhibitors and/or formulations or compositions of the invention. The kit may also include instructions for the use of the one or more WTA biosynthesis inhibitors or formulations of the invention for the treatment of a bacterial infection. The kits of the invention may also comprise one or more containers containing additional drugs for treating a bacterial infection. The invention also includes in some aspects, kits for testing candidate compounds to assess their ability to treat a bacterial infection. In some embodiments of the invention the WTA biosynthesis inhibitor of a kit is the compound 1835F03 (targocil). The kit may include enough for 7, 10, 14, or a 30 day course of antibiotics.

In one aspect, the invention provides methods for identifying antibacterial therapeutic agents. In some embodiments the invention provides methods for identifying a WTA biosynthesis inhibitor. In some embodiments the invention provides methods for identifying an antibacterial TarG inhibitor.

In one embodiment the invention provides an in vivo screen that allows for the selection of antibacterial therapeutic agents that inhibit enzymes involved in WTA biosynthesis. Any essential WTA gene can be deleted in a ΔtarO S. aureus background (D'Elia et al., J. Bacteriol, 188, (2006)). An in vivo based screen has now been established that includes comparing the difference in growth suppression between a wildtype strain (RN4220), with a functional TarO gene, and ΔtarO S. aureus strain, when both strains are contacted with the same candidate agent. A candidate agent is identified as an antibacterial therapeutic agent if the candidate agent can suppress the growth of the wildtype strain, but does not suppress the growth of the ΔtarO S. strain. Inactivation of TarB, TarF, TarG, TarH and TarL suppresses growth in a wildtype strain but not the ΔtarO strain, and the identified antibacterial therapeutic agent is acting as an inhibitor of TarB, TarF, TarG, TarH or TarL. The antibacterial therapeutic agent can acts as an inhibitor through a variety of mechanisms. For instance, the antibacterial therapeutic agent can directly bind one or more of TarB, TarF, TarG, TarH or TarL, and thereby inactivating it, or the antibacterial therapeutic agent can act with upstream or downstream genetic modulators of the gene function of TarB, TarF, TarG, TarH or TarL.

In some embodiments a validation step is performed to validate which Tar gene or gene product is targeted by the antibacterial therapeutic agent.

The term "validate" as used herein, means both the confirmation of a first experiment identifying a set or class of targets or proteins, and/or the further identification of a specific target or protein within the initially identified set of proteins or targets. For instance, if an initial screening experiment identifies a set of four Tar proteins, than the validation of that screening experiment may include confirmation of that set of four Tar proteins, and/or the identification of a unique Tar protein within that set.

In some embodiments the target is validated by contacting a bacterial cell comprising a resistant WTA gene with the antibacterial therapeutic agent. A "bacterial cell comprising a resistant WTA gene" is a bacterial cell that has a mutation in a specific Tar gene, rendering the bacterial cell resistant to the an inhibitor for that specific Tar gene. For instance, a bacterial strain with a mutation in tarG can be used to identify an antibacterial therapeutic agent that acts on TarG, as this strain will be resistant to such an antibacterial therapeutic agent. In some embodiments the bacterial cell comprising a resistant WTA gene is a S. aureus strain. In some embodiments the bacterial cell comprising a resistant WTA gene is a B. subtilis or other strain. In some embodiments the bacterial cell comprising a resistant WTA gene is B. subtilis strain tagG or tagH.

In some embodiments a validation step is performed to validate which Tar gene or gene product is targeted by the antibacterial therapeutic agent by monitoring WTA synthesis. In some embodiments a validation step is performed to identify if TarG is targeted by a antibacterial therapeutic agent by monitoring WTA synthesis, as it was found that mutant strains that were still capable of producing WTAs, have mutations in the tarG gene.

Candidate agents that can be screened to identify an antibacterial therapeutic agent according to the methods of the invention encompass numerous chemical classes, although typically they are organic compounds. Preferably, the candidate agents are small organic compounds, e.g., those having a molecular weight of more than 50 yet less than about 2500, preferably less than about 1000 and, more preferably, less than about 500. Candidate agents comprise functional chemical groups necessary for structural interactions with proteins and/or nucleic acid molecules. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the compound is a nucleic acid molecule, the agent typically is a DNA or RNA molecule, although modified nucleic acid molecules are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological compounds may be subjected to directed or random chemical modifications such as acylation, alkylation, esterification, amidification, etc. to produce structural analogs of the compounds. Candidate agents also include analogs, derivatives, and/or variants of the antibacterial therapeutic agents and WTA synthesis inhibitors described herein.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Strains and Growth Conditions

All S. aureus strains used are derivatives of the sequenced NCTC8325 reference strain (31). Plasmids were constructed in *Escherichia coli* Novablue (Novagen) cells, and introduced into the restriction negative *S. aureus* strain RN4220 by electroporation (32). *S. aureus* was grown in tryptic soy broth (TSB) and antibiotic markers were selected with erythromycin (Em; 10 µg/mL), tetracycline (Tc; 2.5 µg/mL), and chloramphenicol (Cm; single copy integrated into genome 5 µg/mL, plasmid 10 µg/mL). Bacterial strains used are listed in FIG. 25. All cloning materials are listed in FIG. 26.

WTA Inhibitor Screen and Hit Follow-Up

Prior to screening, a wildtype strain of RN4220 was freshly transformed with the plasmid pMS 182 encoding constitutively expressed GFP and a ΔtarO strain of RN4220 was transformed with the plasmid pMS 183 encoding constitutively expressed Mcherry. Both of these plasmids were made by cloning the respective fluorescent protein from the plasmids pDR201 (mCherry) and pKL 147 (Gfp) to incorporate the DNA restriction enzyme sites SalI and AscI. These cloned PCR fragments were then cut and ligated into similarly cut pLI50P$_{pen}$. Following tranformation, both plasmids were maintained with chloramphenicol with Cm at a concentration of 10 µg/mL. Cultures were grown in Tryptic Soy Broth (TSB) that was sterile filtered.

On the night before screening, a single colony of each strain was grown in TSB (Cm 10). On the day of screening, 384 well plates (Corning® 3710) were filled with 40 mL of TSB (Cm 10). Small molecules (dissolved in DMSO) were transferred from library plates to these culture plates using a 300 nL pin transfer. Final culture volume was 80 µL and the final concentration of compound in each plate was 38 µM. For each compound plate there were four daughter plates, wildtype (Gfp) and ΔtarO (MCherry) were done in duplicate in separate plates. Following transfer of the small molecules, each well was inoculated with 40 µL of TSB (Cm 10) containing equal number of cells. To equilibrate the number of cells, the overnight cultures were diluted to an $OD_{600}=2$ and then diluted 1000× into TSB (Cm 10). This diluted culture was used to inoculate the plates containing the small molecules. After inoculation each plate was covered (Corning® 3009), stacked five plates high and incubated at 30° C. for 18 hr. For each plate a positive control (Em at 10 µg/mL) and a negative control (media only) were included in columns 23 and 24.

The following day the plates were read using a Perkin Elmer Envision plate reader for both $OD_{600}$ and fluorescence at the appropriate wavelength for Gfp ($\lambda_{ex}$ 485 nM/$\lambda_{em}$ 532 nM) and Mcherry ($\lambda_{ex}$ 580 nM/$\lambda_{em}$ 640 nM). Data were collected and analyzed to identify compounds that killed the wildtype strain but not the ΔtanO mutant. Although each strain was marked with a unique fluorescence marker to provide an alternative readout of bacterial growth, optical density proved to be a more robust method of growth and was used for hit determination. Data work-up included normalizing the OD data to the positive and negative controls to determine a normalized percent survival for each plate. A hit was defined as greater than 50% survival for the ΔtarO mutant and less than 10% survival for the wildtype strain based on the OD data.

For a secondary screen, hits from the primary screen were evaluated against wildtype and the ΔtarO mutant as described above, but the compound was investigated using a four point dose-response curve starting at a concentration of 50 µM and doing two-fold serial dilutions. Three compounds were validated. One such compound was targocil.

Results of WTA Inhibitor Screen

Figure 13:
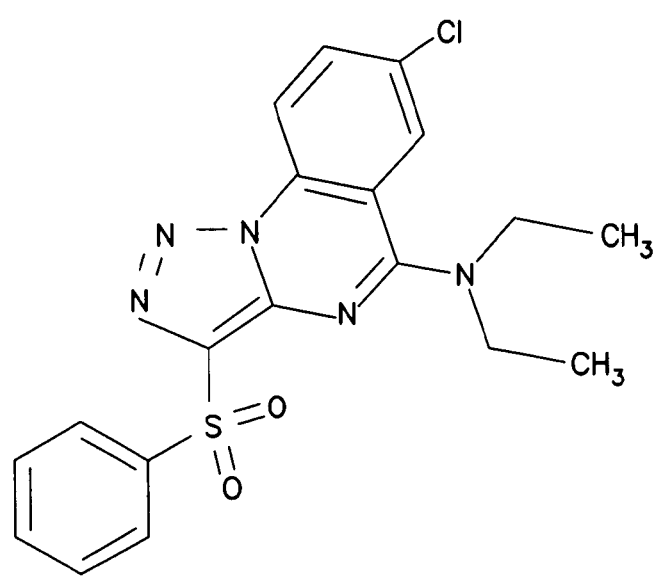
FIG. 13 shows the structure of compound 1835F03 (targocil).
Figure 14:
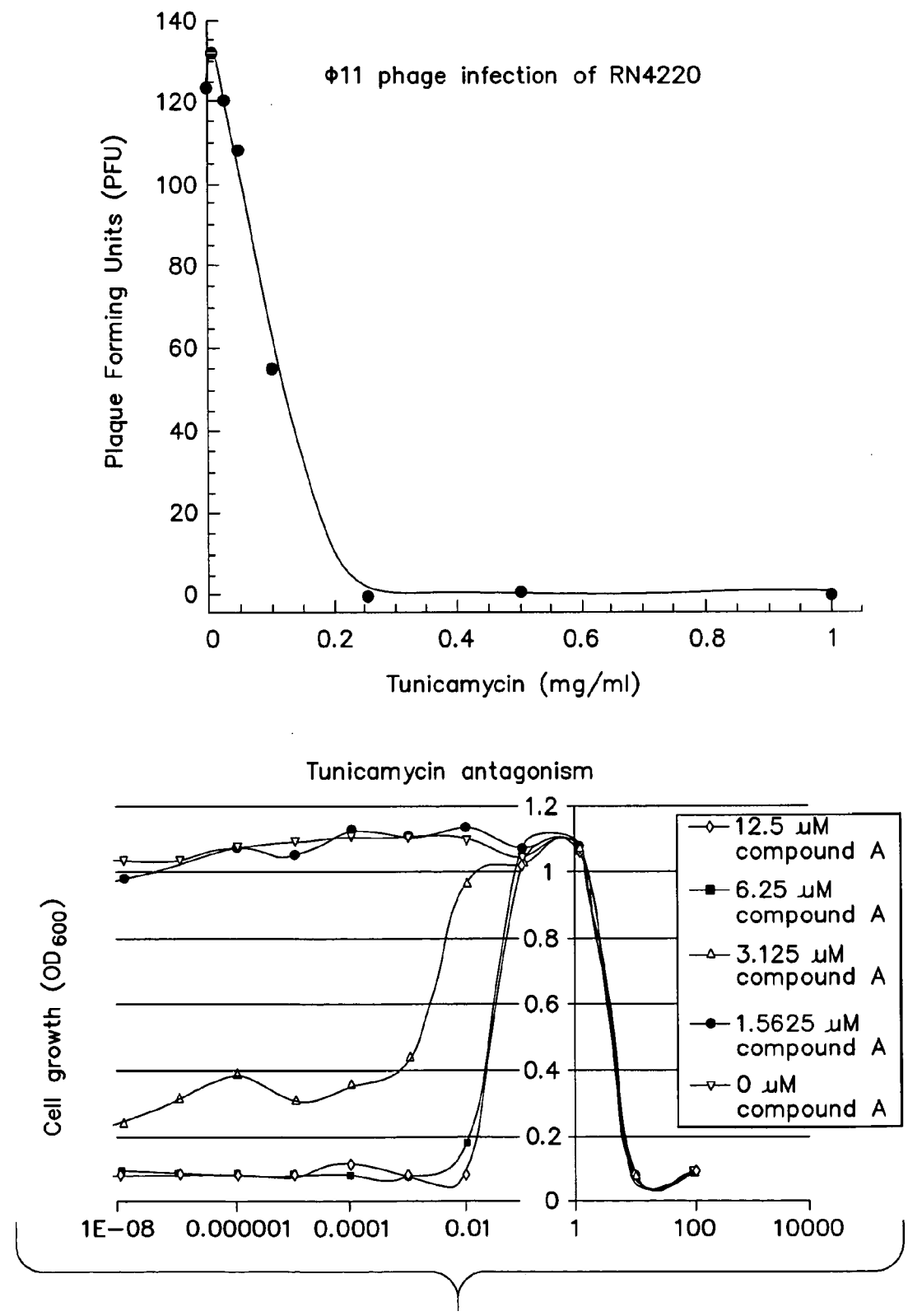
FIG. 14 shows that tunicamycin antagonizes the effect of compound 1835F03 (targocil).

Compound 1835F03 (targocil) was one of the compounds identified by the above screen. The minimum inhibitory concentration for compound 1835F03 (targocil) (FIG. 13) is about 3 uM. Compound 1835F03 (targocil) was effective against numerous strains of *S. aureus* (RN4220, RN450, Newman strain, and Wood strain). TagG as the target of compound 1835F03 (targocil) was validated by sequencing WTA mutants that are resistant to this compound. Some of these resistant mutants were found to have mutations in the first two genes of the pathway (tarO and tarA), effectively shutting down the Wall Teichoic Acid pathway. Mutant strains that were still capable of producing WTAs, were found to have mutations in the tarG gene. Additionally, experiments done with complementing *B. subtilis* tagG and tagH genes into *S. aureus* conferred resistance to the compound 1835F03 (targocil) to *S. aureus*, further supporting the finding of TarG as the target of compound 1835F03 (targocil).

In Vitro Enzyme Inhibition Assays

*S. aureus* TarB, D, F, I, and L were cloned, overexpressed and purified as described previously (S. Brown, Y. H. Zhang, S. Walker, *Chemistry & Biology* 15, 12, Jan. 2008.) Radiometric in vitro assays were run to test the inhibitory effects of targocil on Tar B, D, F, and L, while TarI was assayed for targocil inhibition using an HPLC assay using conditions similar to those previously reported (ibid). See below for exact reaction conditions. Briefly, enzymes were tested at 200 nM and targocil was added to the reactions at 5, 50, or 100 µM. In each case, a reaction with no targocil served as a negative control (active enzymatic reaction) and a reaction with heat-treated enzyme served as a positive control (no enzymatic reaction). Targocil was incubated with all reaction components except the substrates at room temperature. After 10 minutes, substrates were added and the reactions were allowed to proceed for 60 minutes. The reactions were quenched with DMF and the products were imaged/monitored as previously described (ibid). See FIGS. 21a-e for results.

TarD in vitro inhibition assay protocol and data. Each 3 µL reaction contained 50 mM HEPES pH 8, 10 mM MgCl2, 1 mM DTT, 1 µM [14C]-glycerol-3-phosphate, 9 µM glycerol-3-phosphate, 20 µM CTP, 200 nM TarD. The reactions were quenched with 3 µL DMF, and 2 µL of the reaction mixture were combined with 2 µL 2× loading dye (40% glycerol, 0.2% bromophenol blue) and loaded onto a 20% acrylamide/ 0.25M TBE gel as described previously (ibid.). The gel was run at 100V for 40 minutes, dried, and imaged as described previously.

TarI in vitro inhibition assay protocol and data. Each 3 µL reaction contained 50 mM HEPES pH 8, 20 mM MgCl2, 1 mM DTT, 40 µM CTP, 80 µM ribitol-5-phosphate, 200 nM TarI. The reactions were quenched with 30 µL DMF and centrifuged at 16000 g for 20 minutes. The reactions were monitored by HPLC using an anion exchange column, Phenosphere 5µ SAX 250×4.6 mm, 5 µm (Phenomenex), to record the disappearance of the CTP peak and production of a new CDP ribitol peak (Buffer A: 5 mM NH4H2PO4, pH 2.8, Buffer B: 750 mM NH4H2PO4, pH 3.7, isocratic elution 75% B over 20 minutes, UV monitored at 271 nm).

TarF in vitro inhibition assay protocol. Each 3 μL reaction contained 1 μM [14C]-GroP-ManNAc β-(1,4)-GlcNAc-pp-farnesyl, 3 μM [14C]-CDP-glycerol, 20 mM Tris base pH 7.5, 100 mM NaCl, 10 mM MgCl2, 200 nM TarF. The reactions were quenched and imaged as described above for TarB.

TarL in vitro inhibition assay protocol and data. Each 3 μL reaction contained 1 μM [14C] (GroP)2-ManNAc-β-(1,4)-GlcNAc-pp-farnesyl, 50 μM CDP-ribitol, 20 mM Tris base pH 7.5, 100 mM NaCl, 10 mM MgCl2, 200 nM TarL and either 5, 50, or 100 μM targocil. The reactions were quenched and imaged as described above for TarB.

Chemical Compound Characterization

The structure of targocil, (7-chloro-N,N-diethyl-3-(phenylsulfonyl)-[1,2,3]triazolo[1,5-a]quinazolin-5-amine), was verified via $^1$H NMR and mass spectrometry. $^1$H NMR (600 MHz, CDCl$_3$, δ) 8.54 (1H, d, J=9 Hz), 8.21 (2H, d, J=7.8 Hz), 7.99 (1H, d, J=2.4 Hz), 7.84 (1H, dd, J=9, 1.8 Hz), 7.57-7.54 (1H, m), 7.50-7.48 (2H, m), 3.79 (4H, q, J=7.2 Hz), 1.47 (6H, t, J=7.2 Hz); [M+H]$^+$=416.09.

Synthesis of Targocil Analogs

Representative examples for the preparation of WTA biosynthesis inhibitors by the methods previously illustrated in Scheme 1 are provided in the following Examples. All starting materials and reagents are of standard commercial grade, and are used without further purification, or are readily prepared from such materials by routine methods. Those skills in the art of organic synthesis will recognize that starting materials and reaction conditions may be varied to achieve the desired end product.

Example 1

N,N-Diethyl-7,8-dimethoxy-3-(phenylsulfonyl)-[1,2,3]triazolo[1,5-a]quinazolin-5-amine (4-22-7)

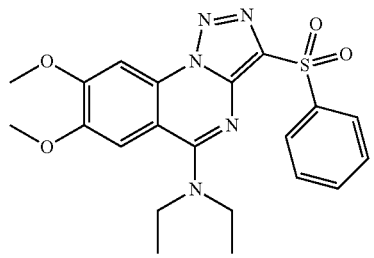 [SMILES: CCN(CC)c1nc2c(S(=O)(=O)c3ccccc3)nnn2c2cc(OC)c(OC)cc12]

Step 1. Synthesis of methyl 2-azido-4,5-dimethoxybenzoate

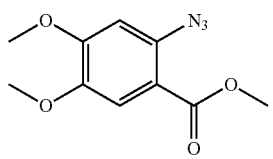

A solution of sodium nitrite (486 mg, 7.1 mmol) in H$_2$O (6 mL) was added to a solution of methyl 2-amino-4,5-dimethoxy benzoate (1.0 g, 4.7 mmol) in 6N—HCl (20 mL) at 0° C. under N$_2$ atmosphere. After stirring for 15 min, the mixture was then added dropwise to a stirred solution of sodium azide (611 mg, 9.4 mmol) and sodium acetate (3.86 g, 47 mmol) in H$_2$O (30 mL) at 0° C. under N$_2$ atmosphere. After the addition was completed, the reaction mixture was warmed to room temperature and stirred for 2 hrs. The resulting precipitate was collected by vacuum filtration, wash with cold water and dried under reduced pressure to yield methyl 2-azido-4,5-dimethoxybenzoate (909 mg, 82%). $^1$H NMR (CDCl$_3$, 600 MHz) δ 7.42 (s, 1H), 6.66 (s, 1H), 3.95 (s, 3H), 3.90 (s, 6H); MS (ES+) m/z 238.2 (M+H)$^+$ Step 2. Synthesis of 7,8-dimethoxy-3-(phenylsulfonyl)-[1,2,3]triazolo[1,5-a]quinazolin-5(4H)-one

Sodium methoxide solution was prepared carefully in situ by dissolving sodium (57 mg, 2.5 mmol) in anhydrous methanol (20 mL) under N$_2$. To this was added phenylsulfonylacetonitrile (199 mg, 1.1 mmol) and the solution was stirred for 20 min at room temperature. Methyl 2-azido-4,5-dimethoxybenzoate (237 mg, 1.0 mmol) was added portionwise and the resulting mixture was stirred overnight at room temperature. After concentrating under reduced pressure, the residue was dissolved in H$_2$O and acidified with 1N—HCl to pH 2. The resulting precipitate was collected by vacuum filtration, wash with cold water and dried under reduced pressure to yield 7,8-dimethoxy-3-(phenylsulfonyl)-[1,2,3]triazolo[1,5-a]quinazolin-5(4H)-one as a tan solid (262 mg, 68%). $^1$H NMR (CDCl$_3$, 600 MHz) δ 9.44 (br s, 1H), 8.12-8.11 (m, 2H), 7.76 (s, 1H), 7.70 (s, 1H), 7.68-7.64 (m, 1H), 7.60-7.57 (m, 2H), 4.12 (s, 3H), 4.03 (s, 3H); MS (ES+) m/z 387.1 (M+H)$^+$ Step 3. Synthesis of 5-chloro-7,8-dimethoxy-3-(phenylsulfonyl)-[1,2,3]triazolo[1,5-a]quinazoline

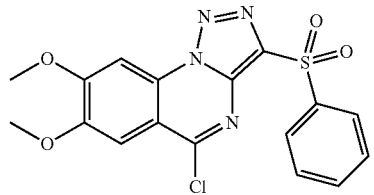 [SMILES: COc1cc2c(Cl)nc3c(S(=O)(=O)c4ccccc4)nnn3c2cc1OC]

A mixture of 7,8-dimethoxy-3-(phenylsulfonyl)-[1,2,3]triazolo[1,5-a]quinazolin-5(4H)-one (262 mg, 0.68 mmol) and tetrabutylammonium chloride (189 mg, 0.68 mmol) in POCl$_3$ (10 mL) was heated at 120° C. for 30 min and then cooled to room temperature. After removal of POCl$_3$ in vacuo, the residue was purified by column chromatography on silica gel eluting with 30% ethyl acetate in hexane to yield 5-chloro-7,8-dimethoxy-3-(phenylsulfonyl)-[1,2,3]triazolo[1,5-a]quinazoline (162 mg, 59%). $^1$H NMR (CDCl$_3$, 600 MHz) δ 8.28-8.26 (m, 2H), 8.04 (s, 1H), 7.61 (s, 1H), 7.60-7.58 (m, 1H); 7.56-7.54 (m, 2H), 4.18 (s, 3H), 4.10 (s, 3H); MS (ES+) m/z 405.0 (M+H)$^+$

Step 4. Synthesis of N,N-Diethyl-7,8-dimethoxy-3-(phenylsulfonyl)-[1,2,3]triazolo[1,5-a]quinazolin-5-amine A mixture of 5-chloro-7,8-dimethoxy-3-(phenylsulfonyl)-[1,2,3]triazolo[1,5-a]quinazoline (25 mg, 0.062 mmol) and diethylamine (32 uL, 0.31 mmol) in DMF (2 mL) was heated at 40° C. for 1.5 hrs. After removal of the solvent, the residue was purified by column chromatography on silica gel eluting with 40% ethyl acetate in hexane to yield the desired product (22 mg, 82%). $^1$H NMR (CDCl$_3$, 600 MHz) δ 8.23 (d, 2H, J=7.2 Hz), 7.93 (s, 1H), 7.55-7.52 (m, 1H), 7.49-7.57 (m, 2H), 7.32 (s, 1H), 4.10 (s, 3H), 3.99 (s, 3H), 3.76 (q, 4H, J=7.2 Hz), 1.46 (t, 6H, J=7.2 Hz); MS (ES+) m/z 442.1 (M+H)$^+$

Example 2

N,N-Diethyl-3-(phenylsulfonyl)-8,9-dihydro-[1,4]dioxino[2.3-g][1,2,3]triazolo[1,5-a]quinazolin-5-amine (4-84-2)

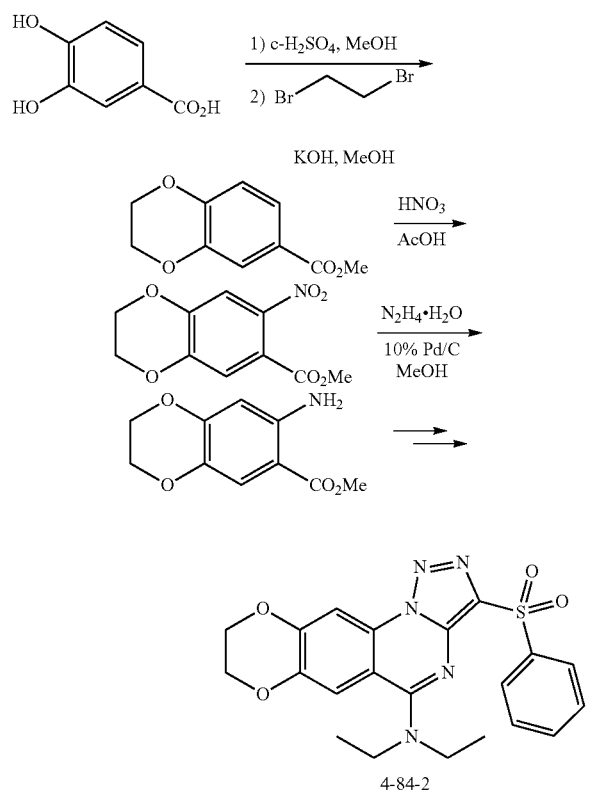

4-84-2

Step 1. Synthesis of methyl 2,3-dihydrobenzo[b][1,4]dioxine-6-carboxylate

A solution of 3,4-dihydroxybenzoic acid (5.0 g, 32 mmol) in methanol (80 mL) containing c-H$_2$SO$_4$ (3 mL) was heated at reflux for 4 hrs and cooled to room temperature. After concentrating under reduced pressure, the residue was dissolved in ethyl acetate and washed successively with water, saturated NaHCO$_3$, and brine. The organic fraction was dried over MgSO$_4$ and concentrated to give 3,4-dihydroxybenzoic acid methyl ester (5.2 g, 96%). $^1$H NMR (DMSO-d$_6$, 600 MHz) δ 9.77 (s, 1H), 9.35 (s, 1H), 7.35 (s, 1H), 7.30 (d, 1H, J=7.8 Hz), 6.79 (d, 1H, J=7.8 Hz), 3.78 (s, 3H).

A mixture of 3,4-dihydroxybenzoic acid methyl ester (5.2 g, 31 mmol), 1,2-dibromoethane (2.9 mL, 34 mmol), and pulverized KOH (3.8 g, 68 mmol) in MeOH was heated at reflux for 30 hrs. After removal of the solvent under reduced pressure, the residue was partitioned between ethyl acetate and water. The ethyl acetate layer was washed with water, dried over MgSO$_4$, concentrated in vacuo and purified by purified by column chromatography on silica gel eluting with 40% ethyl acetate in hexane to yield methyl 2,3-dihydrobenzo[b][1,4]dioxine-6-carboxylate (780 mg, 13%) along with the unreacted starting material (2.6 g). $^1$H NMR (DMSO-d$_6$, 600 MHz) δ 7.45 (d, 1H, J=8.4 Hz), 7.39 (s, 1H), 6.96 (d, 1H, J=8.4 Hz), 4.33-4.28 (m, 4H), 3.80 (s, 3H); MS (ES+) m/z 195.1 (M+H)$^+$

Step 2. Synthesis of methyl 7-nitro-2,3-dihydrobenzo[b][1,4]dioxine-6-carboxylate To a solution of methyl 2,3-dihydrobenzo[b][1,4]dioxine-6-carboxylate (780 mg, 4.0 mmol) in acetic acid (3 mL) was added dropwise conc. HNO$_3$ (4 mL) while keeping the temperature below 20° C. and the resulting reaction mixture was warmed to room temperature. After stirring for 1 hr, the mixture was poured onto ice-water with vigorous stirring. The resulting white precipitate was collected by vacuum filtration and dried under reduced pressure to yield methyl 7-nitro-2,3-dihydrobenzo[b][1,4]dioxine-6-carboxylate (889 mg, 92%). $^1$H NMR (DMSO-d$_6$, 600 MHz) δ 7.64 (s, 1H), 7.30 (s, 1H), 4.41-4.38 (m, 4H), 3.80 (s, 3H); MS (ES+) m/z 240.0 (M+H)$^+$

Step 3. Synthesis of methyl 7-amino-2,3-dihydrobenzo[b][1,4]dioxine-6-carboxylate A solution of hydrazine monohydrate (1.0 mL, 21 mmol) in MeOH (3 mL) was added dropwise to a refluxing suspension of methyl 7-nitro-2,3-dihydrobenzo[b][1,4]dioxine-6-carboxylate (889 mg, 3.7 mmol) and palladium on carbon (10%, 220 mg) in MeOH (25 mL) under N$_2$. After refluxing overnight, the resulting mixture was cooled to room temperature, filtered through celite and the filter cake was washed with MeOH. The combined filtrates were concentrated under reduced pressure and the residue was purified by column chromatography on silica gel eluting with 30% ethyl acetate in hexane to yield methyl 7-amino-2,3-dihydrobenzo[b][1,4]dioxine-6-carboxylate (390 mg, 50%). $^1$H NMR (CDCl$_3$, 600 MHz) δ 7.19 (s, 1H), 6.17 (s, 1H), 4.24-4.22 (m, 2H), 4.17-4.15 (m, 2H), 3.82 (s, 3H); MS (ES+) m/z 210.1 (M+H)$^+$

Step 4. Synthesis of N,N-Diethyl-3-(phenylsulfonyl)-8,9-dihydro-[1,4]dioxino[2.3-g][1,2,3]triazolo[1,5-a]quinazolin-5-amine (4-84-2)

N,N-Diethyl-3-(phenylsulfonyl)-8,9-dihydro-[1,4]dioxino[2.3-g][1,2,3]triazolo[1,5-a]quinazolin-5-amine (4-84-2) was prepared from methyl 7-amino-2,3-dihydrobenzo[b][1,4]dioxine-6-carboxylate similarly as described in Example 1. $^1$H NMR (CDCl$_3$, 600 MHz) δ 8.23-8.21 (m, 2H), 7.99 (s, 1H), 7.55-7.72 (m, 1H), 7.49-7.46 (m, 3H), 4.44-4.43 (m, 2H), 4.38-4.36 (m, 2H), 3.75 (q, 4H, J=7.2 Hz), 1.43 (t, 6H, J=7.2 Hz); MS (ES+) m/z 440.1 (M+H)$^+$ The following compounds were prepared by a procedure similar to that of Example 1.

| ID | Structure | Name | Physical data |
|---|---|---|---|
| 4-22-2 | 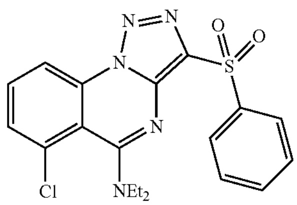 | 6-chloro-N,N-diethyl-3-(phenylsulfonyl)-[1,2,3]triazolo[1,5-α]quinazolin-5-amine | $^1$H NMR (CDCl$_3$, 600 MHz) δ 8.47 (d, 1 H, J = 8.4 Hz), 8.23 (d, 2 H, J = 7.2 Hz), 8.4 (t, 1 H, 8.4 Hz), 7.62 (d, 1 H, 8.4 Hz), 7.58-7.55 (m, 1 H), 7.52-7.49 (m, 2 H), 3.98 (br s, 2 H), 3.44 (br s, 2 H), 1.23 (t, 6 H, J = 7.2 Hz); MS (ES+) m/z 416.1 (M + H)$^+$ |
| 4-22-3 | 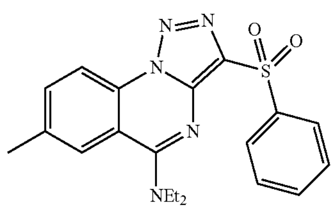 | N,N-diethyl-7-methyl-3-(phenylsulfonyl)-[1,2,3]triazolo[1,5-α]quinazolin-5-amine | $^1$H NMR (CDCl$_3$, 600 MHz) δ 8.45 (d, 1 H, J = 9 Hz), 8.22 (d, 2 H, J = 7.2 Hz), 7.78 (s, 1 H), 7.68 (d, 1 H, J = 9 Hz), 7.53 (d, 1 H, J = 7.2 Hz), 7.49-7.46 (m, 2 H), 3.79 (q, 4 H, J = 7.2 Hz), 2.55 (s, 3 H), 1.46 (t, 6 H, J = 7.2 Hz); MS (ES+) m/z 396.1 (M + H)$^+$ |
| 4-22-5 | 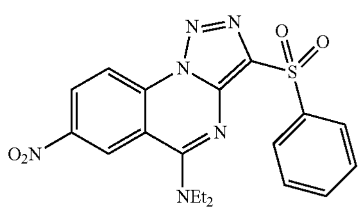 | N,N-diehtyl-7-nitro-3-(phenylsulfonyl)-[1,2,3]triazolo[1,5-α]quinazolin-5-amine | $^1$H NMR (CDCl$_3$, 600 MHz) δ 9.03 (s, 1 H), 8.75-8.71 (m, 2 H), 8.20 (d, 2 H, J = 7.8 Hz), 7.58-7.55 (m, 1 H), 7.52-7.49 (m, 2 H), 3.87 (q, 4 H, J = 7.2 Hz), 1.55 (t, 6 H, J = 7.2 Hz); MS (ES+) m/z 427.1 (M + H)$^+$ |
| 4-22-1 | 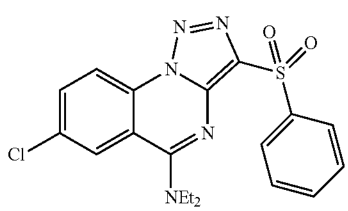 | 7-chloro-N,N-diethyl-3-(phenylsulfonyl)-[1,2,3]triazolo[1,5-α]quinazolin-5-amine | $^1$H NMR (CDCl$_3$, 600 MHz) δ 8.54 (d, 1 H, J = 9 Hz), 8.21 (d, 2 H, J = 7.8 Hz), 7.98 (s, 1 H), 7.84 (d, 1 H, J = 9 Hz), 7.56-7.54 (m, 1 H), 7.50-7.48 (m, 2 H), 3.79 (q, 4 H, J = 7.2 Hz), 1.47 (t, 6 H, J = 7.2 Hz); MS (ES+) m/z 416.1 (M + H)$^+$ |
| 4-22-4 | 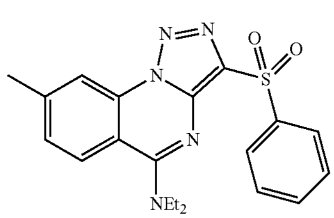 | N,N-diethyl-8-methyl-3-(phenylsulfonyl)-[1,2,3]triazolo[1,5-α]quinazolin-5-amine | $^1$H NMR (CDCl$_3$, 600 MHz) δ 8.39 (s, 1 H), 8.23 (d, 2 H, J = 7.2 Hz), 7.88 (d, 1 H, J = 9 Hz), 7.55-7.53 (m, 1 H), 7.49-7.47 (m, 2 H), 7.39 (d, 1 H, J = 9 Hz), 3.78 (q, 4 H, J = 7.2 Hz), 2.59 (s, 3 H), 1.45 (t, 6 H, J = 7.2 Hz); MS (ES+) m/z 396.1 (M + H)$^+$ |
| 4-22-6 | 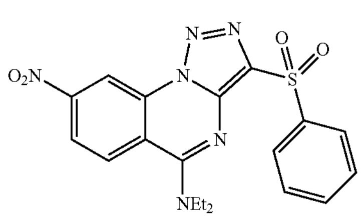 | N,N-diethyl-8-nitro-3-(phenylsulfonyl)-[1,2,3]triazolo[1,5-α]quinazolin-5-amine | $^1$H NMR (CDCl$_3$, 600MHz) δ 9.38 (s, 1 H), 8.40 (d, 1 H, J = 9 Hz), 8.21-8.19 (m, 3 H), 7.58-7.55 (m, 1 H), 7.52-7.49 (m, 2 H), 3.81 (q, 4 H, J = 7.2 Hz), 1.52 (t, 6 H, J = 7.2 Hz); MS (ES+) m/z 427.1 (M + H)$^+$ |

-continued

| ID | Structure | Name | Physical data |
|---|---|---|---|
| 4-24 | 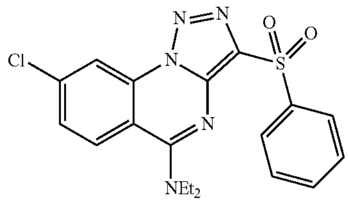 | 8-chlro-N,N-diethyl-3-(phenylsulfonyl)-[1,2,3]triazolo[1,5-α]quinazolin-5-maine | $^1$H NMR (CDCl$_3$, 600 MHz) δ 8.59 (s, 1 H), 8.21 (d, 2 H, J = 7.2 Hz), 7.93 (d, 1 H, J = 9.6 Hz), 7.56-7.54 (m, 2 H), 7.50-7.47 (m, 2 H), 3.78 (q, 4 H, J = 7.2 Hz), 1.46 (t, 6 H, J = 7.2 Hz); MS (ES+) m/z 416.1 (M + H)$^+$ |
| 4-22-8 | 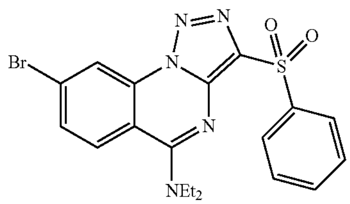 | 8-bromo-N,N-diethyl-3-(phenylsulfonyl)-[1,2,3]triazolo[1,5-α]quinazolin-5-amine | $^1$H NMR (CDCl$_3$, 600 MHz) δ 8.47 (d, 1 H, J = 9 Hz), 8.21 (d, 2 H, J = 7.8 Hz), 8.15 (s, 1 H), 7.97 (d, 1 H, J = 9 Hz), 7.58-7.54 (m, 1 H), 7.50-7.48 (m, 2 H), 3.79 (q, 4 H, J = 7.2 Hz), 1.47 (t, 6 H, J = 7.2 Hz); MS (ES+) m/z 461.1 (M + H)$^+$ |
| 4-20 | 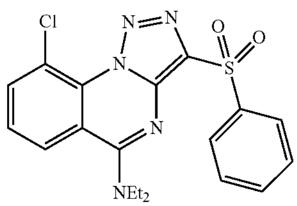 | 9-chloro-N,N-diethyl-3-(phenylsulfonyl)-{1,2,3}triazolo[1,5-α]quinazolin-5-amine | MS (ES+) m/z 416.1 (M + H)$^+$ |
| 4-21-1 | 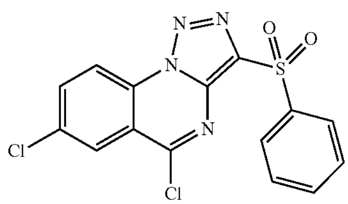 [SMILES: O=S(=O)(c1ccccc1)c1nnn2c1nc(Cl)c1cc(Cl)ccc12] | 5,7-dichloro-3-(phenylsulfonyl)-[1,2,3]triazolo[1,5-α]quinazoline | $^1$H NMR (CDCl$_3$, 600 MHz) δ 8.69 (d, 1 H, J = 9 Hz), 8.41 (s, 1 H), 8.25 (d, 2 H, J = 7.2 Hz), 8.08 (d, 1 H, J = 8.4 Hz), 7.64-7.61 (m, 1 H), 7.57-7.55 (m, 2 H); MS (ES+) m/z 380.0 (M + H)$^+$ |
| 4-18-2 | 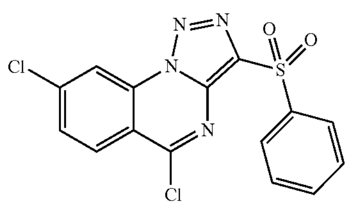 [SMILES: O=S(=O)(c1ccccc1)c1nnn2c1nc(Cl)c1ccc(Cl)cc12] | 5,8-dichloro-3-(phenylsulfonyl)-[1,2,3]triazolo[1,5-α]quinazoline | $^1$H NMR (CDCl$_3$, 600 MHz) δ 8.74 (s, 1 H), 8.36 (d, 1 H, J = 9 Hz), 8.26 (d, 2 H, J = 7.2 Hz), 7.82 (d, 1 H, J = 9 Hz), 7.64-7.61 (m, 1 H), 7.58-7.54 (m, 2 H); MS (ES+) m/z 380.0 (M + H)$^+$ |
| 4-12-3 | 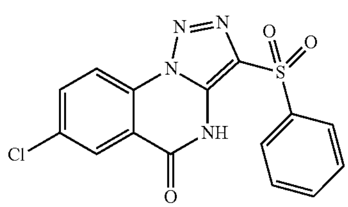 [SMILES: O=c1[nH]c2c(S(=O)(=O)c3ccccc3)nnn2c2ccc(Cl)cc12] | 7-chloro-3-(phenylsulfonyl)-[1,2,3]triazolo[1,5-α]quinazolin-5(4H)-one | $^1$H NMR (DMSO-d$_6$, 600 MHz) δ 12.7 (br s, 1 H), 8.32 (d, 1 H, J = 9 Hz), 8.17-8.16 (m, 3 H), 8.04 (d, 1 H, J = 8.4 Hz), 7.75-7.72 (m, 1 H), 7.68-7.65 (m, 2 H); MS (ES+) m/z 361.0 (M + H)$^+$ |
| 4-84-1 | 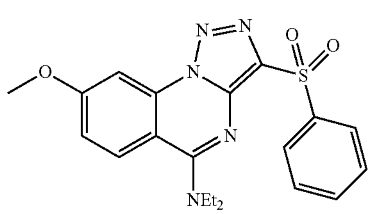 | N,N-diethyl-8-methoxy-3-(phenylsulfonyl)-[1,2,3}trtiazolo[1,5-α]quinazolin-5-amine | $^1$H NMR (CDCl$_3$, 600 MHz) δ 8.23 (d, 2 H, J = 7.2 Hz), 7.93 (s, 1 H), 7.89 (d, 1 H, J = 9 Hz), 7.54-7.52 (m, 1 H), 7.50-7.47 (m, 2 H), 7.12 (d, 1 H, J = 9 Hz), 4.01 (s, 3 H), 3.77 (q, 4 H, J = 7.2 Hz), 1.44 (t, 6 H, J = 7.2 Hz); MS (ES+) m/z 412.1 (M + H)$^+$ |

| ID | Structure | Name | Physical data |
|---|---|---|---|
| 4-84-3 | 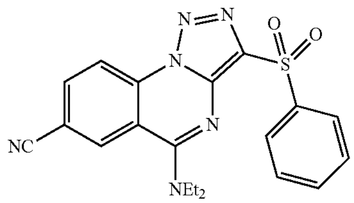 | 5-(diethylamino)-3-(phenylsulfonyl)-[1,2,3]triazolo[1,5-α]quinazoline-7-carbonitrile | ¹H NMR (CDCl₃, 600 MHz) δ 8.67 (d, 1 H, J = 8.4 Hz), 8.30 (s, 1 H), 8.16 (d, 2 H, J = 7.8 Hz), 8.10 (d, 1 H, J = 8.4 Hz), 7.57-7.54 (m, 1 H), 7.50-7.48 (m, 2 H), 3.83 (q, 4H, J = 7.2 Hz), 1.49 (t, 6 H, J = 7.2 Hz); MS (ES+) m/z 407.1 (M + H)⁺ |
| 4-84-4 | 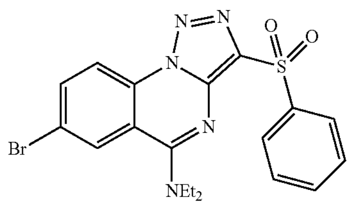 | 7-bromo-N,N-diehtyl-3-(phenylsulfonyl)-[1,2,3]triazolo[1,5-α]quinazolin-5-amine | ¹H NMR (CDCl₃, 600 MHz) δ 8.47 (d, 1 H, J = 9 Hz), 8.21 (d, 2 H, J = 7.8 Hz), 8.15 (s, 1 H), 7.97 (d, 1 H. J = 9 Hz), 7.57-7.54 (m, 1 H), 7.50-7.47 (m, 2 H), 3.79 (q, 4 H, J = 7.2 Hz), 1.47 (t, 6 H, J = 7.2 Hz); MS (ES+) m/z 461.1 (M + H)⁺ |
| 4-84-5 | 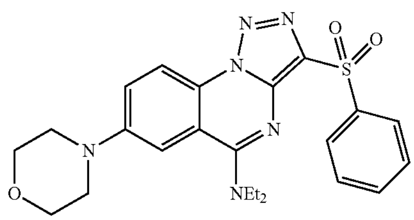 | N,N-diethyl-7-morpholino-3-(phenylsulfonyl)-[1,2,3]triazolo[1,5-α]quinazolin-5-amine | MS (ES+) m/z 467.1 (M + H)⁺ |
| 4-88-1 | 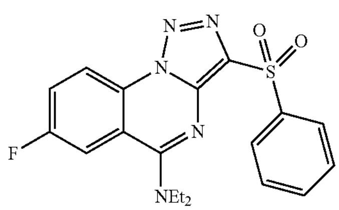 | N,N-diethyl-7-fluoro-3-(phenylsulfonyl)-[1,2,3]triazolo[1,5-α]quinazolin-5-amine | ¹H NMR (CDCl₃, 600 MHz) δ 8.63-8.61 (m, 1 H), 8.23-8.21 (m, 2 H), 7.69-7.62 (m, 2 H), 7.56-7.54 (m, 1 H), 7.50-7.48 (m, 2 H), 3.79 (q, 4 H, J = 7.2 Hz), 1.46 (t, 6 H, J = 7.2 Hz); MS (ES+) m/z 400.1 (M + H)⁺ |
| 4-88-4 | 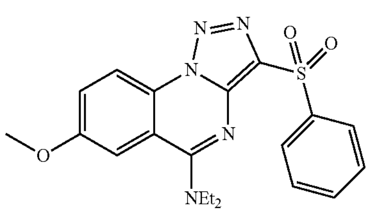 | N,N-diehtyl-7-methozy-3-(phenylsulfonyl)-[1,2,3]triazolo[1,5-α]quinazolin-5-amine | ¹H NMR (CDCl₃, 600 MHz) δ 8.52 (d, 1 H, J = 9 Hz), 8.24-8.22 (m, 2 H), 7.55-7.7.53 (m, 1 H), 7.50-7.46 (m, 3 H), 7.40 (s, 1 H), 3.91 (s, 3 H), 3.78 (q, 4 H, J = 7.2 Hz), 1.46 (t, 6 H, J = 7.2 Hz); MS (ES+) m/z 412.1 (M + H)⁺ |
| 4-82 | 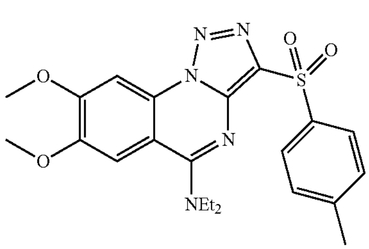 | N,N-diehtyl-7,8-dimethoxy-3-tosyl-[1,2,3]triazolo[1,5-α]quinazolin-5-amine | ¹H NMR (CDCl₃, 600 MHz) δ 8.11 (d, 2 H, J = 8.4 Hz), 7.94 (s, 1 H), 7.32 (s, 1 H), 7.28-7.26 (m, 3 H), 4.10 (s, 3 H), 3.99 (s, 3 H), 3.76 (q, 4 H, J = 7.2 Hz), 2.38 (s, 3 H), 1.46 (t, 6 H, J = 7.2 Hz); MS (ES+) m/z 456.2 (M + H)⁺ |

-continued

| ID | Structure | Name | Physical data |
|---|---|---|---|
| 4-89 | 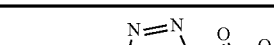 | 3-(4-chlorophenylsulfonyl)-N,N-diehtyl-7,8-dimethoxy-[1,2,3]triazolo[1,5-a]quinazolin-5-amine | $^1$H NMR (CDCl$_3$, 600 MHz) δ 8.18-8.15 (m, 2 H), 7.94 (s, 1 H), 7.46-7.44 (m, 2 H), 7.33 (s, 1 H), 4.11 (s, 3 H), 3.99 (s, 3 H), 3.76 (q, 4 H, J = 7.2 Hz), 1.47 (t, 6 H, J = 7.2 Hz); MS (ES+) m/z 476.1 (M + H)$^+$ |

Production of Targocil Mutants

Targocil-resistant mutants were selected both in liquid culture and on solid media. Mutants were selected on solid media by plating ~5×10$^6$ cfus on TSB agar plates containing targocil at 4×MIC. Colonies that were fully grown after 48 h were passaged four times in the absence of targocil, evaluated for targocil sensitivity and stable mutants were analyzed for the production of WTAs using phage infection.

Mutants prepared in liquid culture were first colony-purified on TSB agar plates. Individual colonies were grown in culture and passaged four times in the absence of targocil. The culture was then colony purified, evaluated for targocil sensitivity and analyzed for the production of WTAs using phage infection.

Corneal Epithelial Invasion Experiment

An overnight culture of S. aureus RN4220 and its isogenic ΔtarO strain were grown with shaking at 37° C. in either 1% DMSO or in the presence of 8×MIC (20 μg/mL) of targocil 1% DMSO. Human corneal epithelial cells (HCEC) were cultured separately in 24-well plates. Prior to incubation with HCEC, the bacteria were washed twice with keratinocyte culture media—serum free (KBM-SFM) including 8×MIC of targocil in 1% DMSO or 1% DMSO. The S. aureus strains (approximately 10$^8$ CFU in 1 mL of KBM-SFM including either 8×MIC of targocil 1% DMSO or 1% DMSO) were then applied to the HCEC monolayers. (The initial inoculum of each group was determined by serial dilution and plate counting.) Following incubation at 37° C. for 1 h, bacteria were removed and the monolayers were washed twice with Hank's balanced salt solution (HBSS), and covered with 1 mL of KBM-SFM containing gentamycin (100 μg/mL) and incubated at 37° C. for 1 h to kill residual extracellular bacteria. The monolayers were washed twice with HBSS, lysed, and homogenized in 1 mL of lysis solution (0.25% trypsin-0.025% Triton X-100). Lysates were serially diluted and plated on brain-heart infusion agar, and colonies were enumerated following overnight incubation at 37° C.

Figure 27B:
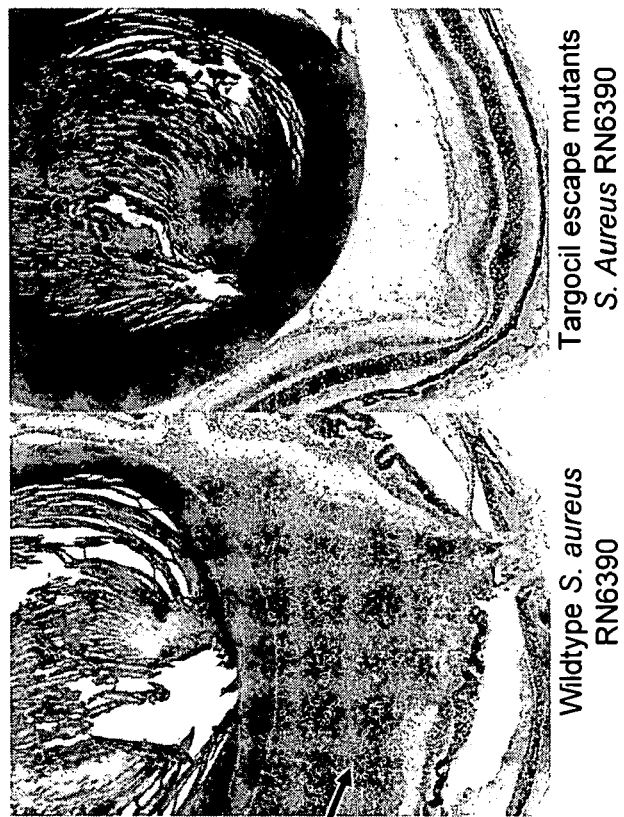
FIG. 27 shows an endophthalmitis model in *S. aureus*. Equivalent inoculums of wildtype *S. aureus* or targocil escape mutants (derived in liquid media prior to injection) were injected into the vitreous of the eye. A) Following injection at two separate time points, electroretinography (ERG) was monitored to determine the severity of infection. In contrast to eyes injected with the wildtype strain, most of the retinal function is not destroyed by inoculation with the targocil escape mutant, and is actually recovered following injection. B) Histopathology slides showing the cross-section of the eye demonstrating colonization in the vitreous by the wildtype, but not by the targocil escape mutants.

The data workup was done by first determining the percentage of internalized bacteria compared to the initial inoculum. This percentage was then normalized to the RN4220 (1% DMSO) control. The error bars represent the standard deviation from six independent samples tested for each group. Student t-test was performed: wildtype vs. tarO mutant P<0.000001; targocil mutant vs. tarO mutant P>0.01. See FIG. 27 for results.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of the formula:

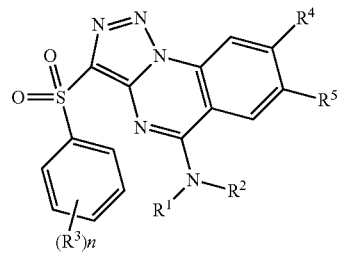

wherein
  $R^1$ and $R^2$ are independently selected from the group consisting of hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^A$; —CO$_2$R$^A$; —C(=O)N(R$^A$)$_2$; or —C(R$^A$)$_3$; wherein each occurrence of R$^A$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;
  wherein $R^1$ and $R^2$ may be taken together with the intervening N atom to form a heterocyclic moiety;
  each occurrence of $R^3$ is independently selected from the group consisting of hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^C$; —C(=O)R$^C$; —CO$_2$R$^C$; —C(=O)N(R$^C$)$_2$; —CN; —SCN; —SR$^C$; —SOR$^A$; —SO$_2$R$^C$; —NO$_2$; —N(R$^C$)$_2$; —NHC(O)R$^C$;

or —C(R$^C$)$_3$; wherein each occurrence of R$^C$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

n is an integer between 1 and 5, inclusive;

R$^4$ is selected from the group consisting of hydrogen; optionally substituted alkenyl; optionally substituted alkynyl; optionally substituted cycloalkyl; optionally substituted cycloalkenyl; optionally substituted cycloalkynyl; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^D$; —C(=O)R$^D$; —CO$_2$R$^D$; —C(=O)N(R$^D$)$_2$; —CN; —SCN; —SR$^D$; —SOR$^A$; —SO$_2$R$^D$; —NO$_2$; —N(R$^D$)$_2$; —NHC(O)R$^D$; or —C(R$^D$)$_3$; wherein each occurrence of R$^D$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy;

R$^5$ is selected from the group consisting of hydrogen; optionally substituted alkenyl, optionally substituted alkynyl, optionally substituted cycloalkyl, optionally substituted cycloalkenyl, optionally substituted cycloalkynyl; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$^E$; —C(=O)R$^E$; —CO$_2$R$^E$; —C(=O)N(R$^E$)$_2$; —CN; —SCN; —SR$^E$; —SOR$^E$; —SO$_2$R$^E$; —NO$_2$; —N(R$^E$)$_2$; —NHC(O)R$^E$; or —C(R$^E$)$_3$; wherein each occurrence of R$^E$ is independently hydrogen; halogen; a protecting group; aliphatic; heteroaliphatic; acyl; aryl moiety; heteroaryl; hydroxy; alkoxy; aryloxy; alkylthioxy; arylthioxy; amino; alkylamino; dialkylamino; heteroaryloxy; or heteroarylthioxy; wherein R$^4$ and R$^5$ may be taken together with the intervening atoms to form a cyclic moiety; and pharmaceutically acceptable salts thereof;

with the provisos that R$^4$ and R$^5$ can not both be hydrogen.

2. The compound of claim 1, wherein n is 1.

3. The compound of claim 1 of the formula:

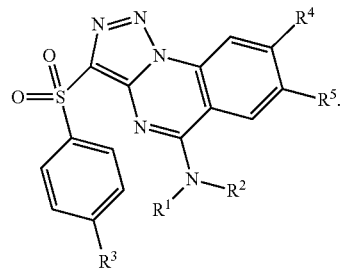

4. The compound of claim 1, wherein R$^3$ is halogen, or cyclic or acyclic, substituted or unsubstituted, branched or unbranched aliphatic.

5. The compound of claim 1, wherein R$^3$ is methyl.

6. The compound of claim 1, wherein R$^3$ is chlorine.

7. The compound of claim 1, wherein R$^4$ is hydrogen.

8. The compound of claim 1, wherein R$^4$ is —OCH$_3$.

9. The compound of claim 1, wherein R$^5$ is hydrogen.

10. The compound of claim 1, wherein R$^5$ is —OCH$_3$.

11. The compound of claim 1, wherein both R$^4$ and R$^5$ are —OCH$_3$.

12. The compound of claim 1, wherein:

both R$^1$ and R$^2$ are C$_{1-6}$ alkyl;

n is 1;

R$^3$ is selected from the group consisting of halogen and C$_{1-6}$ alkyl;

R$^4$ and R$^5$ are independently selected from the list consisting of hydrogen, —CN, —OR$^D$, and heterocyclic; or R$^4$ and R$^5$ may be taken together with the intervening atoms to form a heterocyclic moiety.

13. The compound of claim 1, wherein:

both R$^1$ and R$^2$ are ethyl;

n is 1;

R$^3$ is selected from the group consisting of chloro and methyl;

R$^4$ and R$^5$ are independently selected from the group consisting of hydrogen, —CN, methoxy, and morpholino; or R$^4$ and R$^5$ may be taken together with the intervening atoms to form a 1,4-dioxanyl moiety.

14. The compound of claim 1, wherein the compound is selected from the group consisting of:

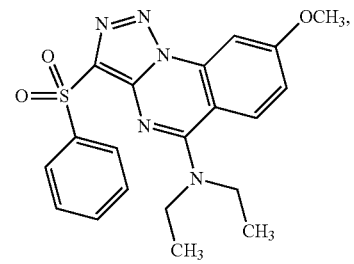

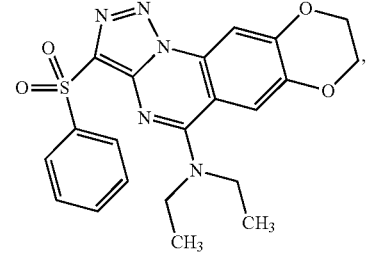

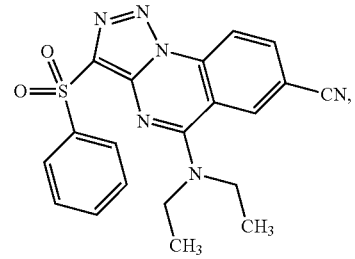

-continued

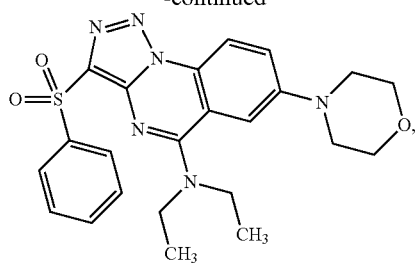

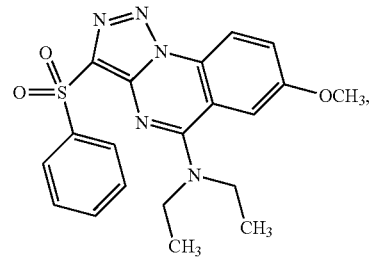

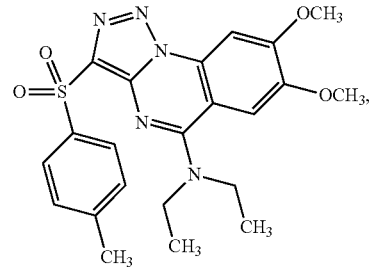

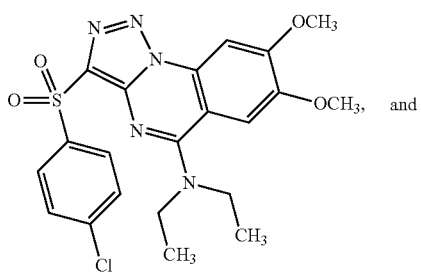

-continued

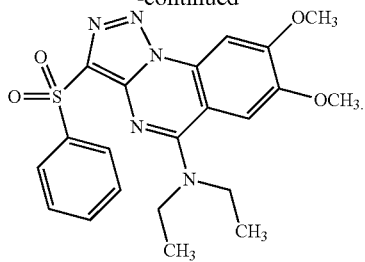

15. A pharmaceutical composition comprising a therapeutically effective amount of compound 1835F03 (targocil)

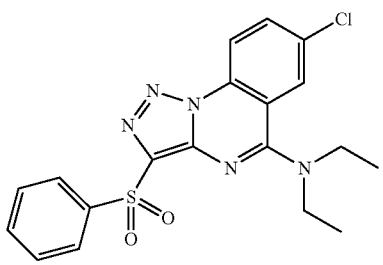

Targocil and a pharmaceutically acceptable excipient.

16. A method of treating bacterial infection in a subject comprising administering to a subject in need of such a treatment a therapeutically effective amount of compound 1835F03 (targocil) or a compound of claim 1.

17. A pharmaceutical composition comprising a therapeutically effective amount of a compound of claim 1 and a pharmaceutically acceptable excipient.

18. A compound of claim 1, wherein both $R^1$ and $R^2$ are independently $C_{1-6}$ alkyl.

19. A compound of claim 1, wherein $R^4$ and $R^5$ are taken together with the intervening atoms to form a five-membered cyclic moiety.

20. A compound of claim 1, wherein $R^4$ and $R^5$ are taken together with the intervening atoms to form a six-membered cyclic moiety.

\* \* \* \* \*

UNITED STATES PATENT AND TRADEMARK OFFICE
CERTIFICATE OF CORRECTION

PATENT NO.         : 8,598,342 B2
APPLICATION NO.    : 12/997429
DATED              : December 3, 2013
INVENTOR(S)        : Suzanne Walker Kahne et al.

Page 1 of 1

It is certified that error appears in the above-identified patent and that said Letters Patent is hereby corrected as shown below:

*In the Claims*

In claim 1, column 60, line 67, please change "-SOR$^A$;" to -- -SOR$^C$; --.

In claim 1, column 61, line 19, please change "-SOR$^A$;" to -- -SOR$^D$; --.

Signed and Sealed this
Sixth Day of May, 2014

Michelle K. Lee
*Deputy Director of the United States Patent and Trademark Office*